US012338448B2

(12) United States Patent
Beissert et al.

(10) Patent No.: US 12,338,448 B2
(45) Date of Patent: Jun. 24, 2025

(54) TRANS-REPLICATING RNA

(71) Applicants: BIONTECH SE, Mainz (DE); TRON-Translationale Onkologie an der Universitätsmedizin der Johannes Gutenberg-Universität Mainz Gemeinnützige GMBH, Mainz (DE)

(72) Inventors: Tim Beissert, Gross-Gerau (DE); Ugur Sahin, Mainz (DE); Mario Perkovic, Frankfurt (DE)

(73) Assignees: TRON-Translationale Onkologie an der Universitatsmedizin der Johannes Gutenberg-Universitat Mainz, Mainz (DE); BIONTECH SE, Mainz (DE)

( * ) Notice: Subject to any disclaimer, the term of this patent is extended or adjusted under 35 U.S.C. 154(b) by 1632 days.

(21) Appl. No.: 16/086,127

(22) PCT Filed: Mar. 13, 2017

(86) PCT No.: PCT/EP2017/055813
§ 371 (c)(1),
(2) Date: Sep. 18, 2018

(87) PCT Pub. No.: WO2017/162461
PCT Pub. Date: Sep. 28, 2017

(65) Prior Publication Data
US 2020/0299724 A1 Sep. 24, 2020

(30) Foreign Application Priority Data
Mar. 21, 2016 (WO) .................. PCT/EP2016/056160

(51) Int. Cl.
C12N 15/86 (2006.01)
C12N 15/00 (2006.01)
(Continued)

(52) U.S. Cl.
CPC ............. *C12N 15/86* (2013.01); *C12N 15/00* (2013.01); *C12N 15/1131* (2013.01);
(Continued)

(58) Field of Classification Search
CPC ...................................... C12N 15/86
See application file for complete search history.

(56) References Cited

U.S. PATENT DOCUMENTS 7,425,337 B2   9/2008  Smith et al.
9,777,043 B2  10/2017  Anderson et al.
2003/0232324 A1  12/2003  Polo et al.

FOREIGN PATENT DOCUMENTS

AU   2001293222 A1   9/2007
CA      2840989 A1   1/2013
(Continued)

OTHER PUBLICATIONS

Grudzien et al., 2004 (RNA, vol. 10, pp. 1479-1487).*
(Continued)

*Primary Examiner* — Mark L Shibuya
(74) *Attorney, Agent, or Firm* — McDonnell Boehnen Hulbert & Bergoff LLP

(57) ABSTRACT

The present invention relates to systems and methods suitable for high-level protein production. In particular, a system comprising two separate RNA molecules is foreseen, each comprising a nucleotide sequence derived from an alphavirus: one RNA molecule comprises a RNA construct for expressing alphavirus replicase, and one RNA molecule comprises a RNA replicon that can be replicated by the replicase in trans. The system of the present invention enables expression of a protein of interest in a cell or organism, but is not associated with undesired virus-particle formation. The present invention is suitable for efficiently and safely producing a protein of interest in a target organ-
(Continued)

ism. Respective methods of protein production in vitro and in vivo as well as medical uses are provided herein. The present invention also provides DNA encoding the RNA molecules of the invention, and cells comprising the RNA molecules of the invention.

19 Claims, 10 Drawing Sheets

(51) Int. Cl.
   *C12N 15/113*   (2010.01)
   *C12N 15/64*    (2006.01)
   *C12N 15/79*    (2006.01)
(52) U.S. Cl.
   CPC .............. *C12N 15/64* (2013.01); *C12N 15/79* (2013.01); *C12N 2770/36141* (2013.01); *C12N 2770/36143* (2013.01)

(56) References Cited

FOREIGN PATENT DOCUMENTS

| CN | 1791678 | 6/2006 |
| RU | 2597974 C2 | 9/2016 |
| WO | WO 2004/085660 | 10/2004 |
| WO | WO 2006/078294 | 7/2006 |
| WO | WO 2008/119827 | 10/2008 |
| WO | WO 2008/156829 | 12/2008 |
| WO | WO 2012/006359 | 1/2012 |
| WO | WO 2012/006376 | 1/2012 |
| WO | WO 2012/051211 | 4/2012 |
| WO | 2013/055905 A1 | 4/2013 |
| WO | 2019/053003 A1 | 3/2019 |

OTHER PUBLICATIONS

International Search Report and Written Opinion mailed May 22, 2017 for International Application No. PCT/EP2017/055813, 13 pages.
Utt et al., "Versatile Trans-Replication Systems for Chikungunya Virus Allow Functional Analysis and Tagging of Every Replicase Protein," PLOS ONE, vol. 11, No. 3, Mar. 10, 2016, p. e0151616, XP055275490.
Wernet et al., "A *Drosophila* Toolkit for the Visualization and Quantification of Viral Replication Launched from Transgenic Genomes," PLOS ONE, vol. 9, No. 11, Nov. 11, 2014, p. e112092, XP055275498.
Diciommo et al., "Rapid, High Level Protein Production Using DNA-based Semliki Forest Virus Vectors," Journal of Biological Chemistry, vol. 273, No. 29, Jul. 17, 1998, pp. 18060-18066.
Spuul et al., "Assembly of Alphavirus Replication Complexes from RNA and protein Components in a Novel trans-Replication System in Mammalian Cells," Journal of Virology, vol. 85, No. 10, May 15, 2011, pp. 4739-4751.
Sanz et al., "Inhibition of host protein synthesis by Sindbis virus: correlation with viral RNA replication and release of nuclear proteins to the cytoplasm," Cellular Microbiology, vol. 17, No. 4, Apr. 19, 2015, pp. 520-541.
Atkins et al., "Therapeutic and prophylactic applications of alphavirus vectors", Expert Reviews in Molecular Medicine, vol. 10:e33 (18 pages) Nov. 2008.
Kim, et al., "Enhancement of protein expression by alphavirus replicons by designing self-replicating subgenomic RNAs," PNAS, vol. 111 (29): 10708-10713; Jul. 2014.
Liljestrom and Garoff, "A new generation of animal cell expression vectors based on the semliki forest virus replicon," Biotechnology Nature, vol. 9: 1356-1361, Dec. 1991.
Merits, et al. "Protelytic processing if Semliki Forest virus-specific non-structural polyprotein by nsP2 protease," Journal of General Virology, vol. 82: 765-773, 2001.
Geall, et al. "Nonviral delivery of self-amplifying RNA vaccines." PNAS, (Sep. 2012) vol. 109, 36: 14604-14609.
Rodriguez-Gascon, et al. "Development of nucleic acid vaccines: use of self-amplifying RNA in lipid hanoparticles." International Journal of Nanomedicine ( 2014) vol. 9: 1833-1843.
Pollard, et al. "Challenges and advances towards the rational design of mRNA vaccines." Trends in Molecular Medicine (2013) vol. 19(12): 1-9.
Schlake, et al. "Developing mRNA-vaccine technologies." RNA Biology (Nov. 2012) vol. 9:11: 1319-1330.
Youn & Chung. "Modified mRNA as an alternative to plasmid DNA (pDNA) for transcript replacement and vaccination therapy." Expert Opin. Biol. Ther. (2015) vol. 15(9):1337-1348.
Zheng Jiping, Hefei—"Regulation of Gene Expression" University of Science and Technology of China Press, p. 153, published on Aug. 31, 2012 (with English machine translation).

\* cited by examiner

TRANS-REPLICATING RNA

REFERENCE TO RELATED APPLICATIONS

This application is a US national stage application under 35 U.S.C. § 371 of International Application No. PCT/EP2017/055813, filed Mar. 13, 2017, which claims priority to International Application No. PCT/EP2016/056160, filed Mar. 21, 2016.

TECHNICAL FIELD OF THE INVENTION

The present invention generally relates to systems and methods suitable for high-level protein production. The present invention contributes a system comprising two separate RNA molecules that are functionally linked: one RNA molecule, the replicase construct, comprises a RNA construct for expressing alphavirus replicase, and a second RNA molecule, the trans-replicon, comprises a RNA sequence that can be replicated by the replicase in trans. The trans-replicon may comprise a gene of interest, e.g. a gene encoding vaccine, for expression. The RNA construct for expressing alphavirus replicase comprises a 5'-cap. It was found that the 5'-cap is crucial for high level expression of the gene of interest in trans. The present invention does not require propagation of virus particles and is suitable for efficiently and safely producing a protein of interest, e.g. a therapeutic protein or an antigenic protein, such as a vaccine, in a target organism, e.g. an animal.

BACKGROUND OF THE INVENTION

The introduction of foreign genetic information encoding one or more polypeptides for prophylactic and therapeutic purposes has been a goal of biomedical research for many years. Prior art approaches share the delivery of a nucleic acid molecule to a target cell or organism, but differ in the type of nucleic acid molecule and/or delivery system: influenced by safety concerns associated with the use of deoxyribonucleic acid (DNA) molecules, ribonucleic acid (RNA) molecules have received growing attention in recent years. Various approaches have been proposed, including administration of single stranded or double-stranded RNA, in the form of naked RNA, or in complexed or packaged form, e.g. in non-viral or viral delivery vehicles. In viruses and in viral delivery vehicles, the genetic information is typically encapsulated by proteins and/or lipids (virus particle). For example, engineered RNA virus particles derived from RNA viruses have been proposed as delivery vehicle for treating plants (WO 2000/053780 A2) or for vaccination of mammals (Tubulekas et al., 1997, Gene, vol. 190, pp. 191-195).

In general, RNA viruses are a diverse group of infectious particles with an RNA genome. RNA viruses can be sub-grouped into single-stranded RNA (ssRNA) and double-stranded RNA (dsRNA) viruses, and the ssRNA viruses can be further generally divided into positive-stranded [(+) stranded] and/or negative-stranded [(−) stranded] viruses. Positive-stranded RNA viruses are prima fade attractive as a delivery system in biomedicine because their RNA may serve directly as template for translation in the host cell.

Alphaviruses are typical representatives of positive-stranded RNA viruses. Alphaviruses replicate in the cytoplasm of infected cells (for review of the alphaviral life cycle see Jose et al., Future Microbiol., 2009, vol. 4, pp. 837-856). The total genome length of many alphaviruses typically ranges between 11,000 and 12,000 nucleotides, and the genome typically has a 5'-cap, and 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together in a second ORF which is found downstream of the first ORF and extends near the 3' terminus of the genome. Typically, the first ORF is larger than the second ORF, the ratio being roughly 2:1.

In cells infected by an alphavirus, only the non-structural proteins are translated from the genomic RNA, while the structural proteins are translatable from a subgenomic transcript, which is an RNA molecule that resembles eukaryotic messenger RNA (mRNA; Gould et al., 2010, Antiviral Res., vol. 87, pp. 111-124). Following infection, i.e. at early stages of the viral life cycle, the (+) stranded genomic RNA directly acts like a messenger RNA for the translation of the non-structural poly-protein (nsP1234). In some alphaviruses, there is an opal stop codon between the coding sequences of nsP3 and nsP4: polyprotein P123, containing nsP1, nsP2, and nsP3, is produced when translation terminates at the opal stop codon, and polyprotein P1234, containing in addition nsP4, is produced upon readthrough of this opal codon (Strauss & Strauss, Microbiol. Rev., 1994, vol. 58, pp. 491-562; Rupp et al., 2015, J. Gen. Virology, vol. 96, pp. 2483-2500). nsP1234 is autoproteolytically cleaved into the fragments nsP123 and nsP4. The polypeptides nsP123 and nsP4 associate to form the (−) strand replicase complex that transcribes (−) stranded RNA, using the (+) stranded genomic RNA as template. Typically at later stages, the nsP123 fragment is completely cleaved into individual proteins nsP1, nsP2, nsP3 and nsP4 (Shirako & Strauss, 1994, J. Virol. Vol. 68, pp. 1874-1885); these proteins assemble to form the (+) strand replicase complex that synthesizes new (+) stranded genomes, using the (−) stranded complement of genomic RNA as template (Kim et al., 2004, Virology, vol. 323, pp. 153-163, Vasiljeva et al., 2003, J. Biol. Chem. Vol. 278, pp. 41636-41645).

Alphavirus structural proteins (core nucleocapsid protein C, envelope protein P62 and envelope protein E1, all constituents of the virus particle) are typically encoded by one single open reading frame under control of a subgenomic promoter (Strauss & Strauss, Microbiol. Rev., 1994, vol. 58, p. 491-562). The subgenomic promoter is recognized by alphaviral non-structural proteins acting in cis. In particular, alphavirus replicase synthesizes a (+) stranded subgenomic transcript using the (−) stranded complement of genomic RNA as template. The (+) stranded subgenomic transcript encodes the alphavirus structural proteins (Kim et al., 2004, Virology, vol. 323, pp. 153-163, Vasiljeva et al., 2003, J. Biol. Chem. Vol. 278, pp. 41636-41645). The subgenomic RNA transcript serves as template for translation of the open reading frame encoding the structural proteins as one poly-protein, and the poly-protein is cleaved to yield the structural proteins. At a late stage of alphavirus infection in a host cell, a packaging signal which is located within the coding sequence of nsP2 ensures selective packaging of genomic RNA into budding virions, packaged by structural proteins (White et al., 1998, J. Virol., vol. 72, pp. 4320-4326).

In infected cells, subgenomic RNA as well as new genomic RNA is provided with a 5'-cap by nsP1 (Pettersson et al. 1980, Eur. J. Biochem. 105, 435-443; Rozanov et al., 1992, J. Gen. Virology, vol. 73, pp. 2129-2134), and provided with a poly adenylate [poly(A)] tail by nsP4 (Rubach et al., Virology, 2009, vol. 384, pp. 201-208). Thus, both subgenomic RNA and genomic RNA resemble messenger RNA (mRNA).

The alphavirus genome comprises four conserved sequence elements (CSEs) which are understood to be important for viral RNA replication in the host cell (Strauss & Strauss, Microbiol. Rev., 1994, vol. 58, pp. 491-562). CSE 1, found at or near the 5' end of the virus genome, is believed to function as a promoter for (+) strand synthesis from (−) strand templates. CSE 2, located downstream of CSE1 but still close to the 5' end of the genome within the coding sequence for nsP1 is thought to act as a promoter for initiation of (−) strand synthesis from a genomic RNA template (note that the subgenomic RNA transcript, which does not comprise CSE 2, does not function as a template for (−) strand synthesis). CSE 3 is located in the junction region between the coding sequence for the non-structural and structural proteins and acts as core promoter for the efficient transcription of the subgenomic transcript. Finally, CSE 4, which is located just upstream of the poly(A) sequence in the 3' untranslated region of the alphavirus genome, is understood to function as a core promoter for initiation of (−) strand synthesis (Jose et al., Future Microbiol., 2009, vol. 4, pp. 837-856). CSE 4 and the poly(A) tail of the alphavirus are understood to function together for efficient (−) strand synthesis (Hardy & Rice, J. Virol., 2005, vol. 79, pp. 4630-4639). In addition to alphavirus proteins, also host cell factors, presumably proteins, may bind to conserved sequence elements (Strauss & Strauss, Microbiol. Rev., 1994, vol. 58, pp. 491-562).

Some features of the genome of a typical alphavirus, Semliki Forest virus (SFV), are illustrated in FIG. 1A.

The hosts of alphaviruses include a wide range of animals, comprising insects, fish and mammals, such as domesticated animals and humans; alphavirus-derived vectors have therefore been considered as a potential vector for delivery of foreign genetic information into a wide range of target organisms. Some prior art approaches of using alphavirus as vectors for delivery of genetic information are reviewed by Strauss & Strauss, Microbiol. Rev., 1994, vol. 58, pp. 491-562 and more recently by Ljungberg and Liljeström, 2015, Expert Rev. Vaccines, vol. 14, pp. 177-94. Already Strauss & Strauss considered alphavirus-based vectors to be particularly advantageous for delivery of genetic information; these authors describe vectors that encode a protein of interest downstream of the subgenomic promoter. A respective nucleic acid molecule (replicon) is schematically depicted in FIG. 1B. It is envisaged that, when a replicon as schematically depicted in FIG. 1B is introduced into a host cell, the encoded replicase is synthesized, forming replication complexes associated with membrane invaginations, which may favor cis-replication. A cis-preferential replication was demonstrated for Rubella virus (Liang and Gillam, 2001, Virology 282, 307-319), a member of the family of Togaviridae with similar genome organization as alphaviruses.

However, replication is not cis-exclusive, trans-replication relying on alphavirus elements on two separate nucleic acid molecules has been described. Alphavirus-derived trans-replication systems comprise two nucleic acid molecules, wherein one nucleic acid molecule encodes a viral replicase and the other nucleic acid molecule is capable of being replicated by said replicase in trans (trans-replication system). Such trans-replication systems require, for transreplication, the presence of both nucleic acid molecules in a single host cell.

Viral RNA vectors have frequently been regarded as disadvantageous because of their potential to propagate in a treated individual by forming propagation competent virus particles. This can be associated with health risks, not only for the treated individual, but also for the general population: for example, some alphaviruses are pathogenic for humans (e.g. Chikungunya virus, Venezuelan equine encephalitis virus (VEEV); the role of alphaviruses in disease of humans and animals is reviewed by Strauss & Strauss, Microbiol. Rev., 1994, vol. 58, pp. 491-562).

In alternative approaches, it was proposed to introduce a non-viral trans-replication system into host cells (Sanz et al., Cellular Microbiol., 2015, vol. 17, pp. 520-541; Spuul et al., J. Virol., 2011, vol. 85, pp. 4739-4751). The trans-replication systems according to these references are based on the introduction of DNA vectors into host cells, wherein the vectors contain the bacteriophage T7 promoter and wherein the host cells are specialized engineered cells expressing the T7 polymerase (Buchholz et al., J. Virol., 1999, vol. 73, pp. 251-259). The DNA constructs used by Spuul et al. encode an internal ribosomal entry site (IRES) element downstream of the T7 promoter; according to that article, the IRES element is implicated in enhancement of expression of the presumably uncapped RNA transcripts synthesized by the T7 polymerase in the cells. Sanz et al. additionally describe the direct use of an RNA replicase construct (encoding nsP1-4) downstream of an IRES; the RNA construct is prepared in vitro in the absence of the cap structure $m^7G$ (5')ppp(5')G. In summary, these two studies show that trans-replication systems are functional either as indirect DNA vectors with a bacteriophage promoter for synthesizing RNA in engineered host cells that express a bacteriophage RNA polymerase, or in the form of direct RNA systems that comprise an IRES for driving translation of the replicase.

In view of safety concerns, the medical and veterinary community is reluctant to administer DNA vectors or self-replicating viral nucleic acids to humans or animals. In addition to that, many prior art approaches for delivery of nucleic acids, particularly RNA, are associated with unsatisfying levels of transgene expression.

Thus, there is a need for safe and efficient methods of delivery of nucleic acid encoding a protein with a therapeutic value, such as a vaccine. As described herein, the aspects and embodiments of the present invention address this need.

SUMMARY OF THE INVENTION

Immunotherapeutic strategies are promising options for the prevention and therapy of e.g. infectious diseases and cancer diseases. The identification of a growing number of pathogen- and tumor-associated antigens led to a broad collection of suitable targets for immunotherapy. The present invention generally embraces agents and methods suitable for efficient immunotherapeutic treatment for the prevention and therapy of diseases.

In a first aspect, the present invention provides a system comprising:
- a RNA construct for expressing alphavirus replicase,
- a RNA replicon that can be replicated by the replicase in trans,
- wherein the RNA construct for expressing alphavirus replicase comprises a 5'-cap for driving translation of the replicase.

In one embodiment, the 5'-cap is a natural 5'-cap or a 5'-cap analog.

In one embodiment, the RNA construct for expressing alphavirus replicase does not comprise an internal ribosomal entry site (IRES) element. Thus, translation of the replicase is not driven by an IRES element.

In one embodiment, the RNA construct for expressing alphavirus replicase comprises an open reading frame (ORF) encoding the replicase. Additionally, a 5'-UTR and/or a 3'-UTR can be present. In a preferred embodiment, the RNA construct for expressing alphavirus replicase comprises
(1) a 5' UTR,
(2) an open reading frame encoding the replicase, and
(3) a 3' UTR.

Preferably, the 5' UTR and/or 3' UTR is heterologous or non-native to the alphavirus from which the replicase is derived.

Preferably, the open reading frame encoding the alphavirus replicase comprises the coding region(s) for non-structural proteins required for RNA replication.

In one embodiment, the RNA construct for expressing alphavirus replicase comprises a 3' poly(A) sequence.

In one embodiment, the RNA construct for expressing alphavirus replicase cannot be replicated by the replicase.

In one embodiment, the RNA replicon comprises:
(1) an alphavirus 5' replication recognition sequence, and
(2) an alphavirus 3' replication recognition sequence.

In one embodiment, the alphavirus 5' replication recognition sequence and the alphavirus 3' replication recognition sequence are capable of directing replication of the RNA replicon in the presence of the replicase. Thus, when the RNA construct for expressing alphavirus replicase and the RNA replicon are present together, these replication recognition sequences direct replication of the RNA.

In one embodiment, the alphavirus 5' replication recognition sequence and the alphavirus 3' replication recognition sequence are native to the alphavirus from which the replicase is derived.

In one embodiment, the RNA replicon comprises a heterologous nucleic acid.

In one embodiment, the RNA replicon comprises an open reading frame encoding a protein of interest.

Preferably, the open reading frame encoding a protein of interest is non-native to the alphavirus from which the replicase is derived. Preferably, the open reading frame encoding a protein of interest does not encode alphavirus structural proteins.

In one embodiment, the RNA replicon comprises a subgenomic promoter.

Preferably, the gene encoding the protein of interest (i.e. the gene of interest) is under control of the subgenomic promoter. This allows that expression of the open reading frame encoding a protein of interest is under the control of the subgenomic promoter.

Preferably, the subgenomic promoter is native to the alphavirus from which the replicase is derived.

Preferably, the subgenomic promoter is a promoter for a structural protein of an alphavirus. This means that the subgenomic promoter is one which is native to an alphavirus and which controls transcription of the gene of one or more structural proteins in said alphavirus.

In one embodiment, the RNA replicon comprises a 3' poly(A) sequence.

In one alternative or additional embodiment, the RNA replicon comprises a 5'-cap.

In one embodiment, the RNA construct for expressing alphavirus replicase and/or the RNA replicon does not comprise an open reading frame encoding an intact alphavirus structural protein.

In one embodiment, the alphavirus is Semliki Forest virus.

In a second aspect, the invention provides a RNA construct for expressing alphavirus replicase comprising a 5'-cap for driving translation of the replicase.

In a third aspect, the invention provides a DNA comprising a nucleic acid sequence encoding the RNA construct for expressing alphavirus replicase according to the first aspect of the invention, a RNA replicon according to the first aspect of the invention, or both. Preferably, the DNA encodes the system according to the first aspect of the invention.

In a fourth aspect, the invention provides a method for producing a protein in a cell comprising the steps of:
(a) obtaining an RNA construct for expressing alphavirus replicase,
(b) obtaining an RNA replicon that can be replicated by the replicase in trans and comprises an open reading frame encoding the protein, and
(c) co-inoculating the RNA construct for expressing alphavirus replicase and the RNA replicon into the cell,
wherein the RNA construct for expressing alphavirus replicase comprises a 5'-cap for driving translation of the replicase.

In various embodiments of the method, the RNA construct for expressing alphavirus replicase and/or the RNA replicon are as defined above for the system of the invention.

In a fifth aspect, the invention provides a cell containing the system of the first aspect. In one embodiment, the cell is inoculated according to the method according to the fourth aspect. In one embodiment, the cell is obtainable by the method of the fourth aspect of the invention. In one embodiment, the cell is part of an organism.

In a sixth aspect, the invention provides a method for producing a protein in a subject comprising the steps of:
(a) obtaining an RNA construct for expressing alphavirus replicase,
(b) obtaining an RNA replicon that can be replicated by the replicase in trans and comprises an open reading frame encoding the protein, and
(c) administering the RNA construct for expressing alphavirus replicase and the RNA replicon to the subject,
wherein the RNA construct for expressing alphavirus replicase comprises a 5'-cap for driving translation of the replicase.

In various embodiments of the method, the RNA construct for expressing alphavirus replicase and/or the RNA replicon are as defined above for the system of the invention.

Symbols and abbreviations: $A_n$: poly(A) tail; C: Cap; SGP: subgenomic promoter (including CSE3); SFV: Semliki Forest virus; CSE: conserved sequence element.

FIG. 1A: The genome of alphaviruses is single stranded RNA of positive sense (ssRNA(+)) that encodes two open reading frames (ORF) for large polyproteins. The ORF at the 5'-end of the genome encodes the non-structural proteins nsP1 to nsP4 (nsP1-4), which are translated and processed to an RNA-dependent RNA-polymerase (replicase); the ORF at the 3'-end encodes the structural proteins-capsid and glycoproteins. The ORF at the 3'-end is under the transcriptional control of a subgenomic promoter (SGP). The alphavirus genome can be referred to as cis-replication system.

FIG. 1B: cis-replicon: By genetic engineering, the structural proteins downstream of the subgenomic promoter (SGP) may be replaced by a gene of interest. A respective construct that has the capability of being replicated by an alphaviral replicase is termed cis-replicon. The cis-replicon is different from the trans-replicon of the present invention (see detailed description).

FIG. 1C: Schematic representation of aspects of the trans-replication system of the present invention. In the trans-replication system the RNA encoding an alphaviral replicase (replicase construct) and the RNA replicon ("transreplicon") are two separate RNA molecules. The RNA replicon preferably encodes a gene of interest. Preferably, the replicase construct resembles a cellular mRNA with one or more, preferably all of: 5'-cap, 5'-UTR, 3'-UTR and a poly(A) tail (replicase encoding mRNA). The replicase construct typically lacks sequence elements required for replication by alphaviral replicase. Sequence elements required for replication by alphaviral replicase are however located on the RNA replicon. In some embodiments the RNA replicon comprises CSE 1, 2 and 4; and an SGP.

Figure 2:
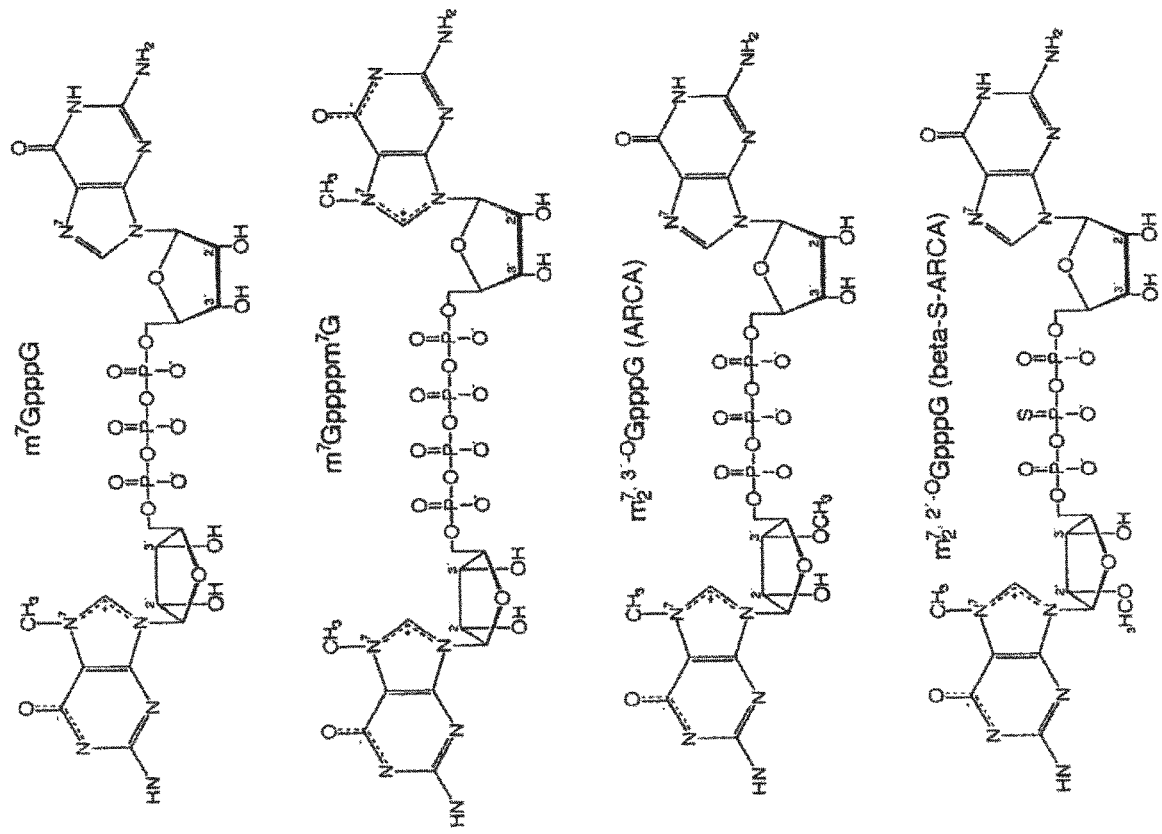

FIG. 2. Structures of cap dinucleotides.

Top: a natural cap dinucleotide, $m^7$GpppG.

Bottom: Phosphorothioate cap analog beta-S-ARCA dinucleotide: There are two diastereomers of beta-S-ARCA due to the stereogenic P center, which are designated D1 and D2 according to their elution characteristics in reverse phase HPLC.

Figure 3:
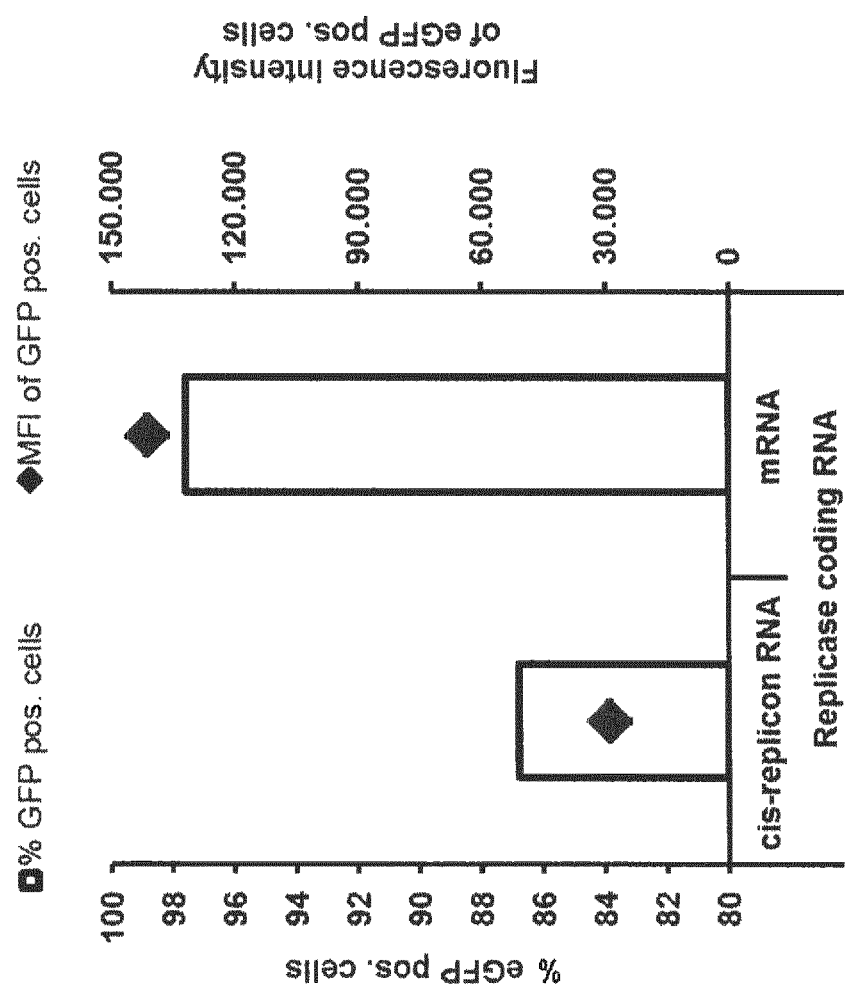

FIG. 3: Efficiency of transgene expression encoded by the replicon is dependent on the molecular environment of the ORF encoding the replicase. eGFP fluorescence intensity measured by FACS following co-delivery of cis-replicon RNA and trans-replicon RNA (left), or co-delivery of replicase coding mRNA and trans-replicon RNA (right) into BHK21 cells (Example 1). Shown is the percentage of eGFP positive cells (bars) and the mean fluorescence intensity (MFI) of eGFP-positive cells (rhombi). mRNA=a replicase construct according to the present invention.

Figure 4:
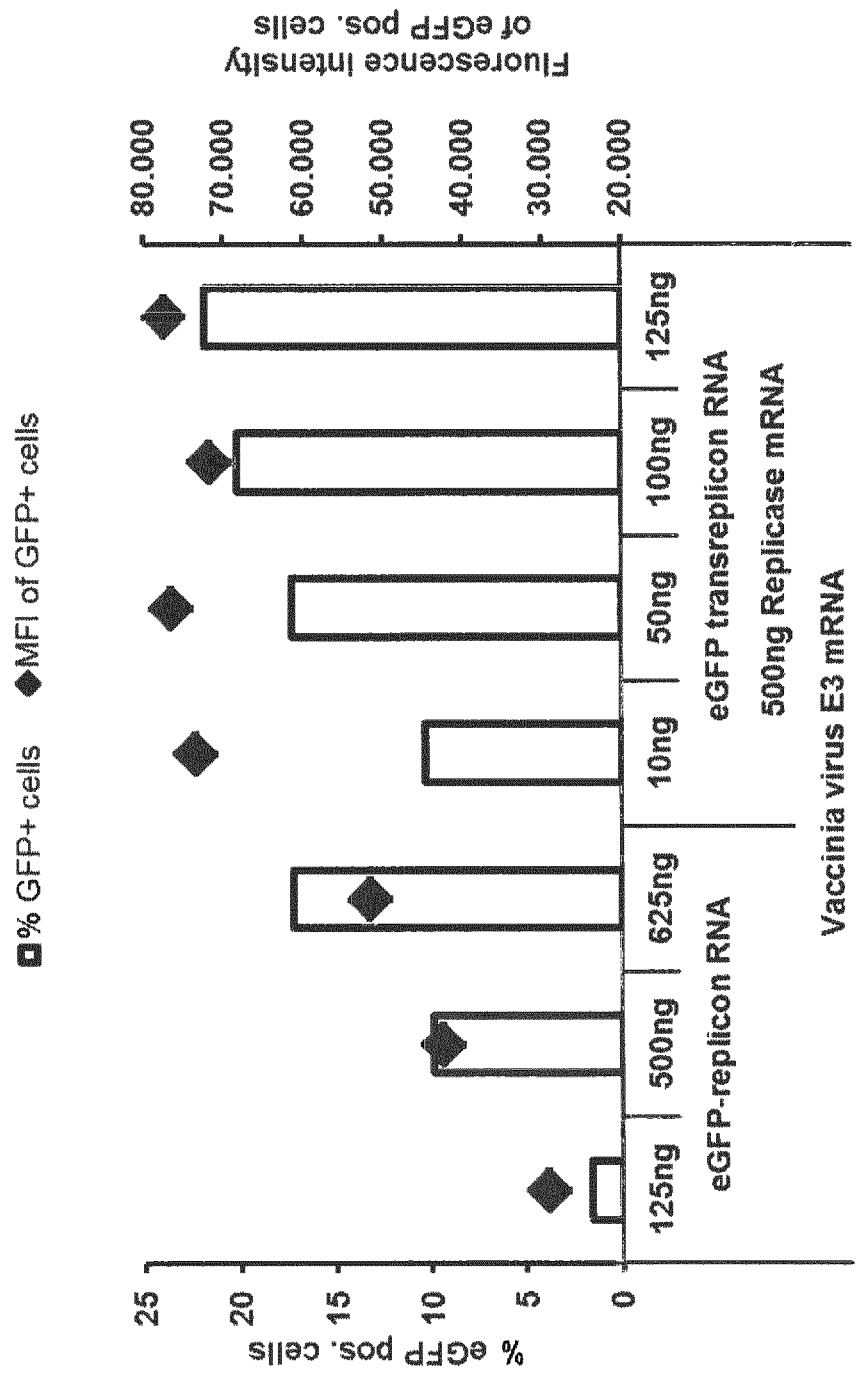

FIG. 4: Gene expression in primary cells confirms efficiency of trans-replication system. eGFP fluorescence intensity measured following delivery of a cis-replication system (eGFP replicon RNA), or co-delivery of a trans-replication system (comprising replicase RNA and trans-replicon RNA) into human foreskin fibroblasts. RNA encoding vaccinia virus protein kinase R (PKR) inhibitor E3 was co-delivered to suppress PKR activation and thereby increase RNA translation (Example 2). Shown is the percentage of eGFP positive cells (bars) and the mean fluorescence intensity (MFI) of eGFP-positive cells (rhombi).

Figure 5A:
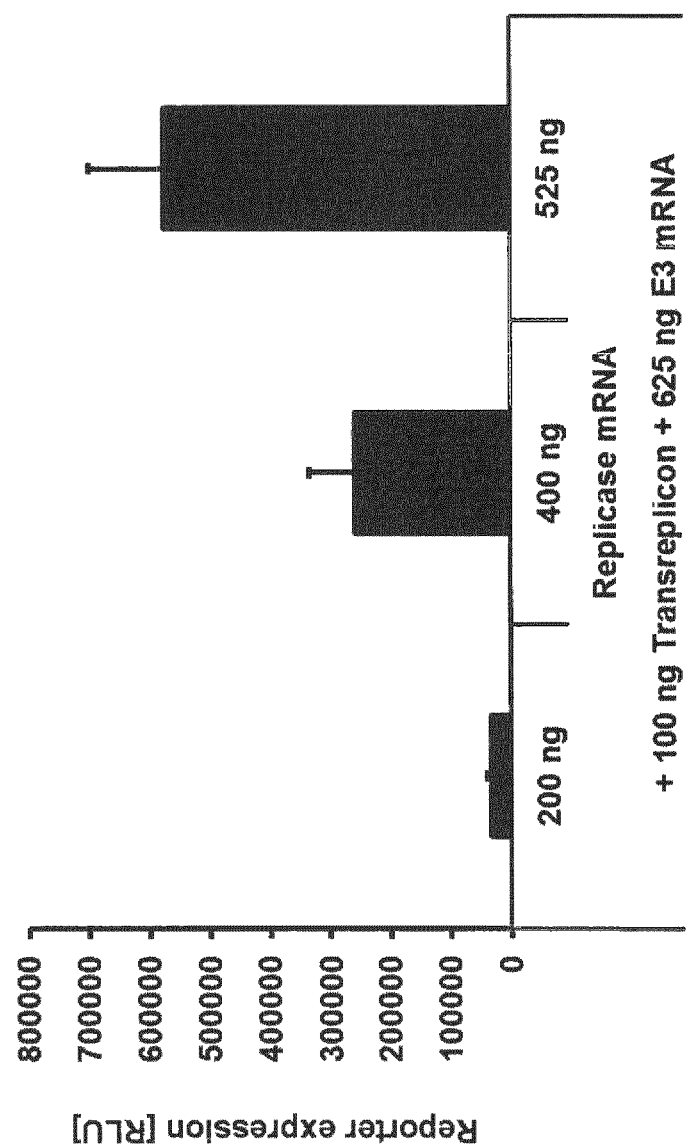
Figure 5:
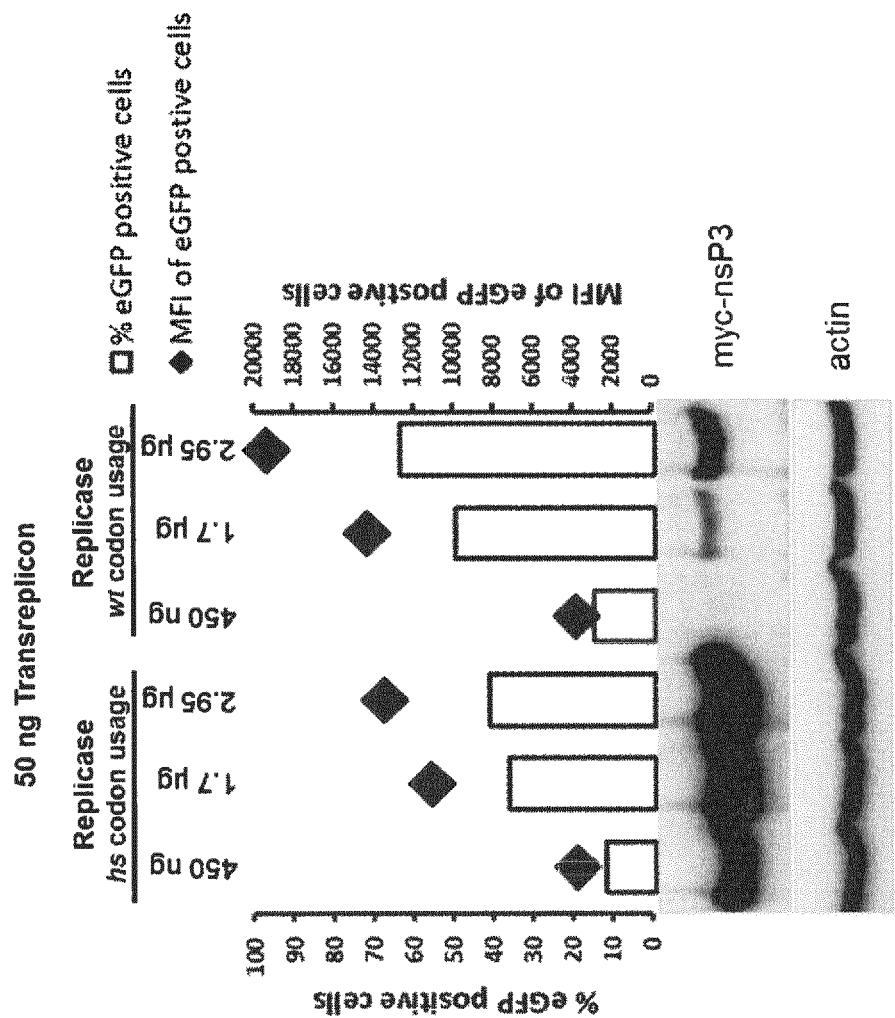

FIG. 5: Influence of amount of replicase RNA and of replicase codon usage.

FIG. 5A: Relative light units [RLU] (secreted NanoLuc), measured after lipofection of primary human foreskin fibroblasts with different amounts of mRNA encoding replicase (Example 3).

FIG. 5B: eGFP fluorescence intensity measured by FACS following co-delivery of replicase RNA and trans-replicon RNA into BHK21 cells (Example 4). Shown is the percentage of eGFP positive cells (bars) and the mean fluorescence intensity (MFI) of eGFP-positive cells (rhombi). As described in Example 4, modifying the codon usage is disadvantageous for transgene expression and for productive replication of trans-replicon (for details see Example 4). hs codon usage: *Homo sapiens*-adapted codon usage; wt codon usage: codon usage of wild type alphavirus.

Bottom part: Western blot indicating levels of myc-nsP3 and actin.

Figure 6:
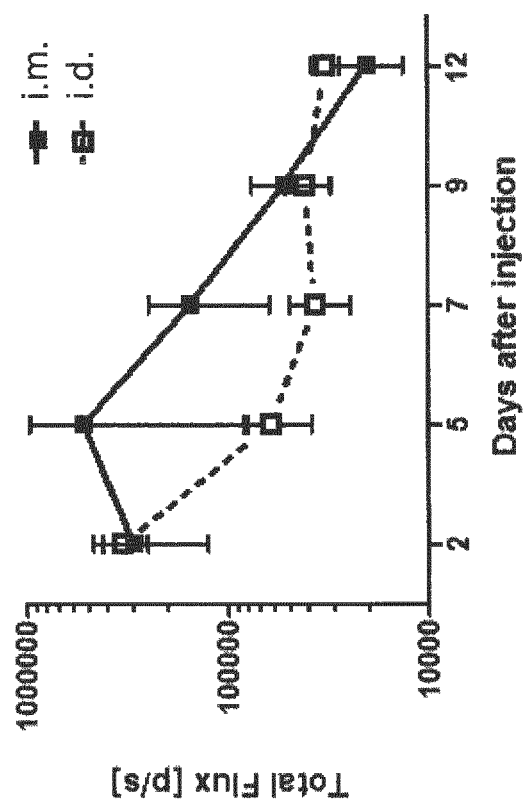

FIG. 6: Efficient in vivo expression of a transgene encoded by the trans-replicon. Bioluminescence imaging (BLI) of mice after intramuscular (i.m.) and intradermal (i.d.) co-injection of a trans-replication system according to the invention, comprising luciferase encoding trans-replicon RNA and a replicase construct in the form of mRNA (Example 5). Luminescence is expressed as photons per second [p/s].

Figure 7:
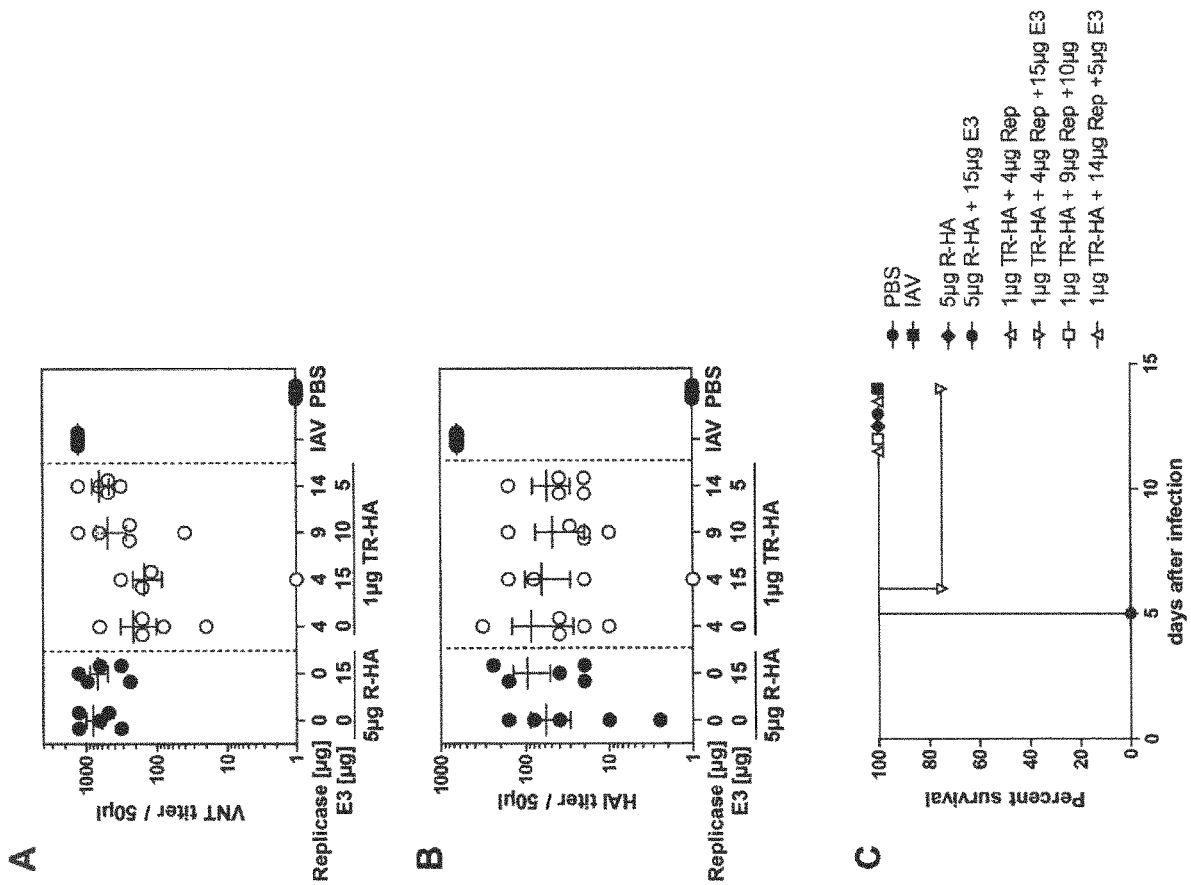

FIG. 7: trans-replicons encoding Influenza HA as protein of interest provide protection from lethal virus infections. As described in Example 6, Balb/C mice were vaccinated intradermally twice (prime-boost) within 3 weeks with either 5 μg cis-replicon encoding Influenza HA (R-HA) or 1 μg trans-replicon (TR-HA). Where indicated, 4 μg to 14 μg mRNA encoding replicase was co-administered with the trans-replicon. Where indicated, different amounts of Vaccinia virus E3 encoding mRNA were co-administered to improve translation.

Positive control: inactivated virus (IAV). Negative control: solvent (PBS buffer).

FIG. 7A: Determination of virus neutralization titer (VNT) on the day before challenge infections with lethal doses of Influenza virus.

FIG. 7B: Hemagglutinin inhibition (HAI) assay of mouse sera.

FIG. 7C: Kaplan-Meier curves showing survival of mice following challenge infections. PBS buffer treated mice died within 5 days.

Figure 8:
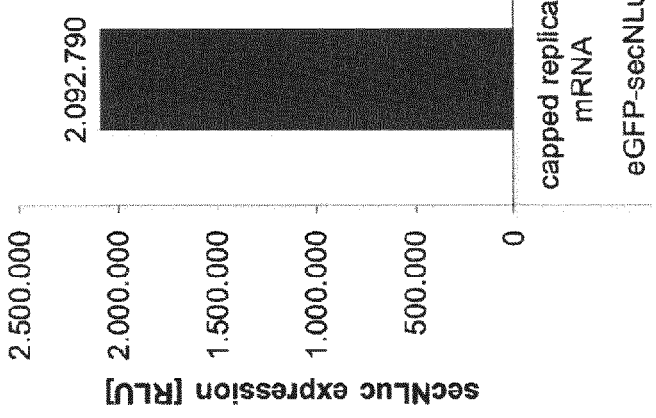
Figure 8:
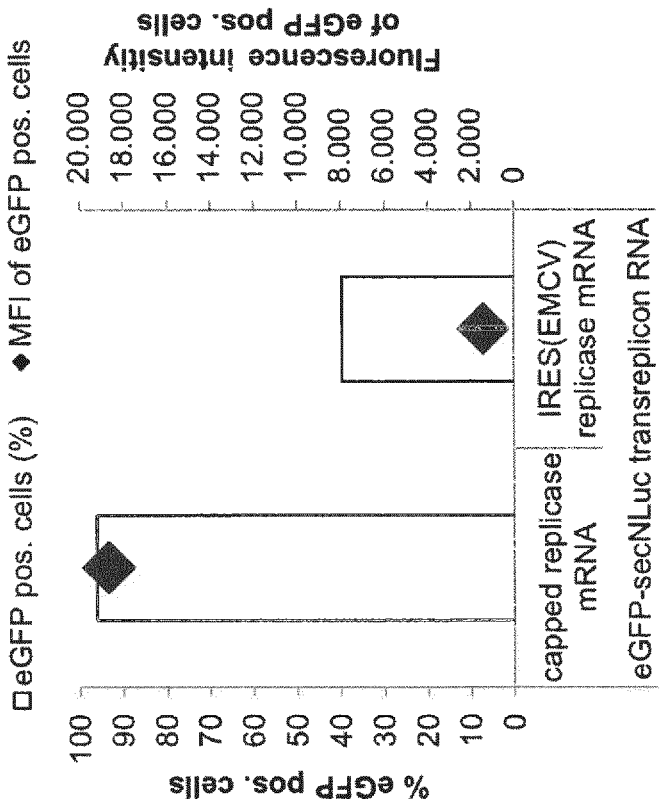
Figure 8:
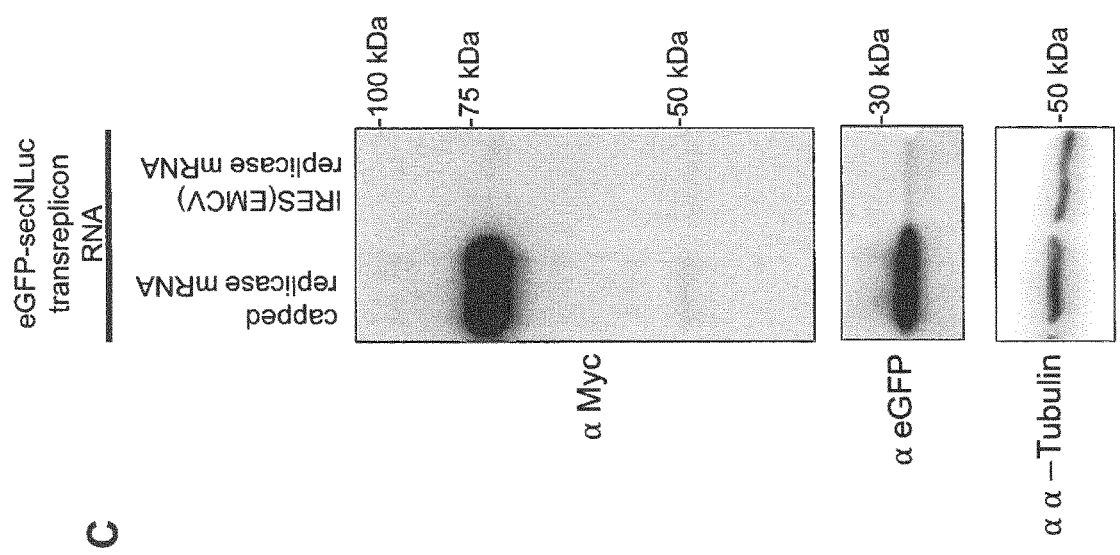

FIG. 8: Influence of the cap. BHK21 cells were electroporated with transreplicon RNA encoding eGFP and secNLuc (secretable luciferase) separated by the self-cleaving peptide P2A (porcine teschovirus-1 2A) together with either beta-S-ARCA(D2) capped replicase mRNA or uncapped mRNA with IRES(EMCV) (internal ribosomal entry site from encephalomyocarditis virus) upstream of the replicase ORF. 24 h after electroporation cells were analysed by FACS for eGFP expression (A), supernatants were analysed for secretion levels of secNLuc by Nano-Glo® Luciferase Assay System (Promega) (B) and the replicase expression was analysed by Western blot (C).

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to disclose and encompass embodiments which combine the explicitly described embodiments with any number of the disclosed and/or preferred elements. Furthermore, any permutations and combinations of all described elements in this application should be considered disclosed by this description unless the context indicates otherwise.

The term "about" means approximately or nearly, and in the context of a numerical value or range set forth herein preferably means+/−10% of the numerical value or range recited or claimed.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Unless expressly specified otherwise, the term "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Indications of relative amounts of a component characterized by a generic term are meant to refer to the total amount of all specific variants or members covered by said generic term. If a certain component defined by a generic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount; more preferably no other variants or members covered by the generic term are present at all.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present invention was not entitled to antedate such disclosure.

Terms such as "reduce" or "inhibit" as used herein means the ability to cause an overall decrease, preferably of 5% or greater, 10% or greater, 20% or greater, more preferably of 50% or greater, and most preferably 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The term "net charge" refers to the charge on a whole object, such as a compound or particle.

An ion having an overall net positive charge is a cation while an ion having an overall net negative charge is an anion. Thus, according to the invention, an anion is an ion with more electrons than protons, giving it a net negative charge; and a cation is an ion with fewer electrons than protons, giving it a net positive charge.

Terms as "charged", "net charge", "negatively charged" or positively charged", with reference to a given compound or particle, refer to the electric net charge of the given compound or particle when dissolved or suspended in water at pH 7.0.

The term "nucleic acid" according to the invention also comprises a chemical derivatization of a nucleic acid on a nucleotide base, on the sugar or on the phosphate, and nucleic acids containing non-natural nucleotides and nucleotide analogs. In some embodiments, the nucleic acid is a deoxyribonucleic acid (DNA) or a ribonucleic acid (RNA).

According to the present invention, the term "RNA" or "RNA molecule" relates to a molecule which comprises ribonucleotide residues and which is preferably entirely or substantially composed of ribonucleotide residues. The term "ribonucleotide" relates to a nucleotide with a hydroxyl group at the 2'-position of a β-D-ribofuranosyl group. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxy nucleotides. These altered RNAs can be referred to as analogs, particularly analogs of naturally occurring RNAs.

According to the invention, RNA may be single-stranded or double-stranded. In some embodiments of the present invention, single-stranded RNA is preferred. The term "single-stranded RNA" generally refers to embodiments wherein no complementary nucleic acid strand (typically no complementary RNA strand; i.e. no complementary RNA molecule) is associated with the RNA molecule. Single-stranded RNA can exist as minus strand [(−) strand] or as plus strand [(+) strand]. The (+) strand is the strand that comprises or encodes genetic information. The genetic information may be for example a polynucleotide sequence encoding a protein. When the (+) strand RNA encodes a protein, the (+) strand may serve directly as template for translation (protein synthesis). The (−) strand is the complement of the (+) strand. In the case of double-stranded RNA, (+) strand and (−) strand are two separate RNA molecules, and both these RNA molecules associate with each other to form a double-stranded RNA ("duplex RNA").

The term "stability" of RNA relates to the "half-life" of RNA. "Half-life" relates to the period of time which is needed to eliminate half of the activity, amount, or number of molecules. In the context of the present invention, the half-life of RNA is indicative for the stability of said RNA. The half-life of RNA may influence the "duration of expression" of the RNA. It can be expected that RNA having a long half-life will be expressed for an extended time period.

"Fragment" or "fragment of a nucleic acid sequence" relates to a part of a nucleic acid sequence, i.e. a sequence which represents the nucleic acid sequence shortened at the 5'- and/or 3'-end(s). Preferably, a fragment of a nucleic acid sequence comprises at least 80%, preferably at least 90%, 95%, 96%, 97%, 98%, or 99% of the nucleotide residues from said nucleic acid sequence. In the present invention those fragments of RNA molecules are preferred which retain RNA stability and/or translational efficiency.

The term "variant" with respect to, for example, nucleic acid and amino acid sequences, according to the invention includes any variants, in particular mutants, viral strains, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code. A species homolog is a nucleic acid or amino acid sequence with a different species of origin from that of a given nucleic acid or amino acid sequence. A virus homolog is a nucleic acid or amino acid sequence with a different virus of origin from that of a given nucleic acid or amino acid sequence.

According to the invention, nucleic acid variants include single or multiple nucleotide deletions, additions, mutations and/or insertions in comparison with the reference nucleic acid. Deletions include removal of one or more nucleotides from the reference nucleic acid. Addition variants comprise 5'- and/or 3'-terminal fusions of one or more nucleotides, such as 1, 2, 3, 5, 10, 20, 30, 50, or more nucleotides. Mutations can include but are not limited to substitutions, wherein at least one nucleotide in the sequence is removed and another nucleotide is inserted in its place (such as transversions and transitions), abasic sites, crosslinked sites, and chemically altered or modified bases. Insertions include the addition of at least one nucleotide into the reference nucleic acid.

Variants of specific nucleic acid sequences preferably have at least one functional property of said specific sequences and preferably are functionally equivalent to said specific sequences, e.g. nucleic acid sequences exhibiting properties identical or similar to those of the specific nucleic acid sequences.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "% identical" is intended to refer, in particular, to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

For example, the BLAST program "BLAST 2 sequences" which is available on the website http://www.ncbi.nlm.nih.gov/blast/bl2seq/wblast2.cgi may be used.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

According to the invention, a "nucleic acid sequence which is derived from a nucleic acid sequence" refers to a nucleic acid which is a variant of the nucleic acid from which it is derived. Preferably, a sequence which is a variant with respect to a specific sequence, when it replaces the specific sequence in an RNA molecule retains RNA stability and/or translational efficiency.

The terms "transcription" and "transcribing" relate to a process during which a nucleic acid molecule with a particular nucleic acid sequence (the "nucleic acid template") is read by an RNA polymerase so that the RNA polymerase produces a single-stranded RNA molecule. During transcription, the genetic information in a nucleic acid template is transcribed. The nucleic acid template may be DNA; however, e.g. in the case of transcription from an alphaviral nucleic acid template, the template is typically RNA. Subsequently, the transcribed RNA may be translated into protein. According to the present invention, the term "transcription" comprises "in vitro transcription", wherein the term "in vitro transcription" relates to a process wherein RNA, in particular mRNA, is in vitro synthesized in a cell-free system. Preferably, cloning vectors are applied for the generation of transcripts. These cloning vectors are generally designated as transcription vectors and are according to the present invention encompassed by the term "vector". According to the present invention, RNA preferably is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

The single-stranded nucleic acid molecule produced during transcription typically has a nucleic acid sequence that is the complementary sequence of the template.

According to the invention, the terms "template" or "nucleic acid template" or "template nucleic acid" generally refer to a nucleic acid sequence that may be replicated or transcribed.

The term "nucleic acid sequence transcribed from a nucleic acid sequence" refers to a nucleic acid sequence, where appropriate as part of a complete RNA molecule, which is a transcription product of a template nucleic acid sequence. Typically, the transcribed nucleic acid sequence is a single-stranded RNA molecule.

"3' end of a nucleic acid" refers according to the invention to that end which has a free hydroxy group. In a diagrammatic representation of double-stranded nucleic acids, in particular DNA, the 3' end is always on the right-hand side. "5' end of a nucleic acid" refers according to the invention to that end which has a free phosphate group. In a diagrammatic representation of double-strand nucleic acids, in particular DNA, the 5' end is always on the left-hand side.

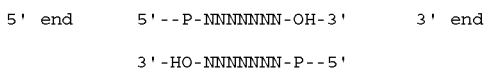

"upstream" describes the relative positioning of a first element of a nucleic acid molecule with respect to a second element of that nucleic acid molecule, wherein both elements are comprised in the same nucleic acid molecule, and wherein the first element is located nearer to the 5' end of the nucleic acid molecule than the second element of that nucleic acid molecule. The second element is then said to be "downstream" of the first element of that nucleic acid molecule. An element that is located "upstream" of a second element can be synonymously referred to as being located "5'" of that second element. For a double-stranded nucleic acid molecule, indications like "upstream" and "downstream" are given with respect to the (+) strand.

According to the invention, "functional linkage" or "functionally linked" relates to a connection within a functional relationship. A nucleic acid is "functionally linked" if it is functionally related to another nucleic acid sequence. For example, a promoter is functionally linked to a coding sequence if it influences transcription of said coding sequence. Functionally linked nucleic acids are typically adjacent to one another, where appropriate separated by further nucleic acid sequences, and, in particular embodiments, are transcribed by RNA polymerase to give a single RNA molecule (common transcript).

In particular embodiments, a nucleic acid is functionally linked according to the invention to expression control sequences which may be homologous or heterologous with respect to the nucleic acid.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3'-untranslated sequences involved in initiating transcription and translation, respectively. More specifically, 5'-untranscribed expression control sequences include a promoter region which encompasses a promoter sequence for transcription control of the functionally linked gene. Expression control sequences may also include enhancer sequences or upstream activator sequences. An expression control sequence of a DNA molecule usually includes 5'-untranscribed and 5'- and 3'-untranslated sequences such as TATA box, capping sequence, CAAT sequence and the like. An expression control sequence of alphaviral RNA may include a subgenomic promoter and/or one or more conserved sequence element(s). A specific expression control sequence according to the present invention is a subgenomic promoter of an alphavirus, as described herein.

The nucleic acid sequences specified herein, in particular transcribable and coding nucleic acid sequences, may be combined with any expression control sequences, in particular promoters, which may be homologous or heterologous to said nucleic acid sequences, with the term "homologous" referring to the fact that a nucleic acid sequence is also functionally linked naturally to the expression control sequence, and the term "heterologous" referring to the fact that a nucleic acid sequence is not naturally functionally linked to the expression control sequence.

A transcribable nucleic acid sequence, in particular a nucleic acid sequence coding for a peptide or protein, and an expression control sequence are "functionally" linked to one another, if they are covalently linked to one another in such a way that transcription or expression of the transcribable and in particular coding nucleic acid sequence is under the control or under the influence of the expression control sequence. If the nucleic acid sequence is to be translated into a functional peptide or protein, induction of an expression control sequence functionally linked to the coding sequence results in transcription of said coding sequence, without causing a frame shift in the coding sequence or the coding sequence being unable to be translated into the desired peptide or protein.

The term "promoter" or "promoter region" refers to a nucleic acid sequence which controls synthesis of a transcript, e.g. a transcript comprising a coding sequence, by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor. A specific promoter according to the present invention is a subgenomic promoter of an alphavirus, as described herein. Other specific promoters are genomic plus-strand or negative-strand promoters of an alphavirus.

The term "core promoter" refers to a nucleic acid sequence that is comprised by the promoter. The core promoter is typically the minimal portion of the promoter required to properly initiate transcription. The core promoter typically includes the transcription start site and a binding site for RNA polymerase.

A "polymerase" generally refers to a molecular entity capable of catalyzing the synthesis of a polymeric molecule from monomeric building blocks. A "RNA polymerase" is a molecular entity capable of catalyzing the synthesis of a RNA molecule from ribonucleotide building blocks. A "DNA polymerase" is a molecular entity capable of catalyzing the synthesis of a DNA molecule from deoxy ribonucleotide building blocks. For the case of DNA polymerases and RNA polymerases, the molecular entity is typically a protein or an assembly or complex of multiple proteins. Typically, a DNA polymerase synthesizes a DNA molecule based on a template nucleic acid, which is typically a DNA molecule. Typically, a RNA polymerase synthesizes a RNA molecule based on a template nucleic acid, which is either a DNA molecule (in that case the RNA polymerase is a DNA-dependent RNA polymerase, DdRP), or is RNA molecule (in that case the RNA polymerase is a RNA-dependent RNA polymerase, RdRP).

A "RNA dependent RNA polymerase" or an "RdRP", is an enzyme that catalyzes the transcription of RNA from an RNA template. In the case of alphaviral RNA-dependent RNA polymerase, sequential synthesis of (−) strand complement of genomic RNA and of (+) strand genomic RNA leads to RNA replication. Alphaviral RNA-dependent RNA polymerase is thus synonymously referred to as "RNA replicase". In nature, RNA-dependent RNA polymerases are typically encoded by all RNA viruses except retroviruses. Typical representatives of viruses encoding a RNA-dependent RNA polymerase are alphaviruses.

According to the present invention, "RNA replication" generally refers to an RNA molecule synthesized based on the nucleotide sequence of a given RNA molecule (template RNA molecule). The RNA molecule that is synthesized may be e.g. identical or complementary to the template RNA molecule. In general, RNA replication may occur via synthesis of a DNA intermediate, or may occur directly by RNA-dependent RNA replication mediated by a RNA-dependent RNA polymerase (RdRP). In the case of alphaviruses, RNA replication does not occur via a DNA intermediate, but is mediated by a RNA-dependent RNA polymerase (RdRP): a template RNA strand (first RNA strand) serves as template for the synthesis of a second RNA strand that is complementary to the first RNA strand or to a part thereof. The second RNA strand may in turn optionally serve as a template for synthesis of a third RNA strand that is complementary to the second RNA strand or to a part thereof. Thereby, the third RNA strand is identical to the first RNA strand or to a part thereof. Thus, RNA-dependent RNA polymerase is capable of directly synthesizing a complementary RNA strand of a template, and of indirectly synthesizing an identical RNA strand (via a complementary intermediate strand).

According to the invention, the term "gene" refers to a particular nucleic acid sequence which is responsible for producing one or more cellular products and/or for achieving one or more intercellular or intracellular functions. More specifically, said term relates to a nucleic acid section (typically DNA; but RNA in the case of RNA viruses) which comprises a nucleic acid coding for a specific protein or a functional or structural RNA molecule.

An "isolated molecule" as used herein, is intended to refer to a molecule which is substantially free of other molecules such as other cellular material. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant techniques.

The term "vector" is used here in its most general meaning and comprises any intermediate vehicles for a nucleic acid which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids, virus genomes, and fractions thereof.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

According to the invention, the term "expression" is used in its most general meaning and comprises production of RNA, or of RNA and protein. It also comprises partial expression of nucleic acids. Furthermore, expression may be transient or stable. With respect to RNA, the term "expression" or "translation" relates to the process in the ribosomes of a cell by which a strand of messenger RNA directs the assembly of a sequence of amino acids to make a peptide or protein.

According to the invention, the term "mRNA" means "messenger-RNA" and relates to a transcript which is typically generated by using a DNA template and encodes a peptide or protein. Typically, mRNA comprises a 5'-UTR, a protein coding region, a 3'-UTR, and a poly(A) sequence. mRNA may be generated by in vitro transcription from a DNA template. The in vitro transcription methodology is known to the skilled person. For example, there is a variety of in vitro transcription kits commercially available. According to the invention, mRNA may be modified by stabilizing modifications and capping.

According to the invention, the terms "poly(A) sequence" or "poly(A) tail" refer to an uninterrupted or interrupted sequence of adenylate residues which is typically located at the 3' end of an RNA molecule. An uninterrupted sequence is characterized by consecutive adenylate residues. In nature, an uninterrupted poly(A) sequence is typical. While a poly(A) sequence is normally not encoded in eukaryotic DNA, but is attached during eukaryotic transcription in the cell nucleus to the free 3' end of the RNA by a template-independent RNA polymerase after transcription, the present invention encompasses poly(A) sequences encoded by DNA.

According to the invention, a nucleic acid such as RNA, e.g. mRNA, may encode a peptide or protein. Accordingly, a transcribable nucleic acid sequence or a transcript thereof may contain an open reading frame (ORF) encoding a peptide or protein.

According to the invention, the term "nucleic acid encoding a peptide or protein" means that the nucleic acid, if present in the appropriate environment, preferably within a cell, can direct the assembly of amino acids to produce the peptide or protein during the process of translation. Preferably, RNA according to the invention is able to interact with the cellular translation machinery allowing translation of the peptide or protein.

According to the invention, the term "peptide" comprises oligo- and polypeptides and refers to substances which comprise two or more, preferably 3 or more, preferably 4 or more, preferably 6 or more, preferably 8 or more, preferably 10 or more, preferably 13 or more, preferably 16 or more, preferably 20 or more, and up to preferably 50, preferably 100 or preferably 150, consecutive amino acids linked to one another via peptide bonds. The term "protein" refers to large peptides, preferably peptides having at least 151 amino acids, but the terms "peptide" and "protein" are used herein usually as synonyms.

The terms "peptide" and "protein" comprise, according to the invention, substances which contain not only amino acid components but also non-amino acid components such as sugars and phosphate structures, and also comprise substances containing bonds such as ester, thioether or disulfide bonds.

According to the invention, the term "alphavirus" is to be understood broadly and includes any virus particle that has characteristics of alphaviruses. Characteristics of alphavirus include the presence of a (+) stranded RNA which encodes genetic information suitable for replication in a host cell, including RNA polymerase activity. Further characteristics of many alphaviruses are described e.g. in Strauss & Strauss, Microbiol. Rev., 1994, vol. 58, pp. 491-562; Gould et al., 2010, Antiviral Res., vol. 87, pp. 111-124; Rupp et al., 2015, J. Gen. Virology, vol. 96, pp. 2483-2500. The term "alphavirus" includes alphavirus found in nature, as well as any variant or derivative thereof. In some embodiments, a variant or derivative is not found in nature.

In one embodiment, the alphavirus is an alphavirus found in nature. Typically, an alphavirus found in nature is infectious to any one or more eukaryotic organisms, such as an animal (including a vertebrate such as a human, and an arthropod such as an insect). In typical embodiments, an alphavirus found in nature is infectious to an animal. Many alphaviruses found in nature are infectious to vertebrates and/or arthropods (Strauss & Strauss, Microbiol. Rev., 1994, vol. 58, pp. 491-562).

An alphavirus found in nature is preferably selected from the group consisting of the following: Barmah Forest virus complex (comprising Barmah Forest virus); Eastern equine encephalitis complex (comprising seven antigenic types of Eastern equine encephalitis virus); Middelburg virus complex (comprising Middelburg virus); Ndumu virus complex (comprising Ndumu virus); Semliki Forest virus complex (comprising Bebaru virus, Chikungunya virus, Mayaro virus and its subtype Una virus, O'Nyong Nyong virus, and its subtype lgbo-Ora virus, Ross River virus and its subtypes Bebaru virus, Getah virus, Sagiyama virus, Semliki Forest virus and its subtype Me Tri virus); Venezuelan equine encephalitis complex (comprising Cabassou virus, Everglades virus, Mosso das Pedras virus, Mucambo virus, Paramana virus, Pixuna virus, Rio Negro virus, Trocara virus and its subtype Bijou Bridge virus, Venezuelan equine encephalitis virus); Western equine encephalitis complex (comprising Aura virus, Babanki virus, Kyzylagach virus, Sindbis virus, Ockelbo virus, Whataroa virus, Buggy Creek virus, Fort Morgan virus, Highlands J virus, Western equine encephalitis virus); and some unclassified viruses including Salmon pancreatic disease virus; Sleeping Disease virus; Southern elephant seal virus; Tonate virus. More preferably, the alphavirus is selected from the group consisting of Semliki Forest virus complex (comprising the virus types as indicated above, including Semliki Forest virus), Western equine encephalitis complex (comprising the virus types as indicated above, including Sindbis virus), Eastern equine encephalitis virus (comprising the virus types as indicated above), Venezuelan equine encephalitis complex (comprising the virus types as indicated above, including Venezuelan equine encephalitis virus).

In a further preferred embodiment, the alphavirus is Semliki Forest virus. In an alternative further preferred embodiment, the alphavirus is Sindbis virus. In an alternative further preferred embodiment, the alphavirus is Venezuelan equine encephalitis virus.

In some embodiments of the present invention, the alphavirus is not an alphavirus found in nature. Typically, an alphavirus not found in nature is a variant or derivative of an alphavirus found in nature, which is distinguished from an alphavirus found in nature by at least one mutation in the nucleotide sequence, i.e. the genomic RNA. The mutation in the nucleotide sequence may be selected from an insertion, a substitution or a deletion of one or more nucleotides, compared to an alphavirus found in nature. A mutation in the nucleotide sequence may or may not be associated with a mutation in a polypeptide or protein encoded by the nucleotide sequence. For example, an alphavirus not found in nature may be an attenuated alphavirus. An attenuated alphavirus not found in nature is an alphavirus that typically has at least one mutation in its nucleotide sequence by which it is distinguished from an alphavirus found in nature, and that is either not infectious at all, or that is infectious but has a lower disease-producing ability or no disease-producing ability at all. As an illustrative example, TC83 is an attenuated alphavirus that is distinguished from the Venezuelan equine encephalitis virus (VEEV) found in nature (MyKinney et al., 1963, Am. J. Trop. Med. Hyg., 1963, vol. 12; pp. 597-603).

The term "found in nature" means "present in nature" and includes known objects as well as objects that have not yet been discovered and/or isolated from nature, but that may be discovered and/or isolated in the future from a natural source.

Members of the alphavirus genus may also be classified based on their relative clinical features in humans: alphaviruses associated primarily with encephalitis, and alphaviruses associated primarily with fever, rash, and polyarthritis.

The term "alphaviral" means found in an alphavirus, or originating from an alphavirus, or derived from an alphavirus, e.g. by genetic engineering.

According to the invention, "SFV" stands for Semliki Forest virus. According to the invention, "SIN" or "SINV" stands for Sindbis virus. According to the invention, "VEE" or "VEEV" stands for Venezuelan equine encephalitis virus.

The term "conserved sequence element" or "CSE" refers to a nucleotide sequence found in alphavirus RNA. These sequence elements are termed "conserved" because orthologs are present in the genome of different alphaviruses, and orthologous CSEs of different alphaviruses preferably share a high percentage of sequence identity and/or a similar secondary or tertiary structure. The term CSE includes CSE 1, CSE 2, CSE 3 and CSE 4 (for details see Jose et al., Future Microbiol., 2009, vol. 4, pp. 837-856).

According to the invention, the term "subgenomic promoter" or "SGP" refers to a nucleic acid sequence upstream (5') of a nucleic acid sequence (e.g. coding sequence), which controls transcription of said nucleic acid sequence by providing a recognition and binding site for RNA polymerase, typically RNA-dependent RNA polymerase. The SGP may include further recognition or binding sites for further factors. A subgenomic promoter is typically a genetic element of a positive strand RNA virus, such as an alphavirus. A subgenomic promoter of alphavirus is a nucleic acid sequence comprised in the viral genomic RNA. The subgenomic promoter is generally characterized in that it allows initiation of the transcription (RNA synthesis) in the presence of an RNA-dependent RNA polymerase, e.g. alphavirus replicase. A RNA (−) strand, i.e. the complement of alphaviral genomic RNA, serves as a template for synthesis of a (+) strand subgenomic RNA molecule, and subgenomic (+) strand synthesis is typically initiated at or near the subgenomic promoter. For illustrative and non-limiting purposes, the typical localization of the SGP as comprised in an example alphavirus genome is illustrated in FIG. 1A. However, the term "subgenomic promoter" as used herein, is not confined to any particular localization in a nucleic acid comprising such subgenomic promoter. In some embodiments, the SGP is identical to CSE 3 or overlaps with CSE 3 or comprises CSE 3.

The term "autologous" is used to describe anything that is derived from the same subject. For example, "autologous cell" refers to a cell derived from the same subject. Introduction of autologous cells into a subject is advantageous because these cells overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues or cells.

The term "heterologous" is used to describe something consisting of multiple different elements. As an example, the introduction of one individual's cell into a different individual constitutes a heterologous transplant. A heterologous gene is a gene derived from a source other than the subject.

The following provides specific and/or preferred variants of the individual features of the invention. The present invention also contemplates as particularly preferred embodiments those embodiments, which are generated by combining two or more of the specific and/or preferred variants described for two or more of the features of the present invention.

System of the Present Invention

In a first aspect, the present invention provides a system comprising:
 a RNA construct for expressing alphavirus replicase,
 a RNA replicon that can be replicated by the replicase in trans,
 wherein the RNA construct for expressing alphavirus replicase comprises a 5'-cap.

The 5'-cap serves the purpose of driving translation of the replicase.

Thus, the present invention provides a system comprising two nucleic acid molecules: a first RNA molecule for expressing replicase (i.e. encoding replicase); and a second RNA molecule (the replicon). The RNA construct for expressing replicase is synonymously referred to herein as "replicase construct".

In the system of the present invention, the role of the replicase is to amplify the replicon in trans. The replicon can therefore be referred to as trans-replicon. If the replicon encodes a gene of interest for expression, the expression levels of the gene of interest and/or the duration of expression may be regulated in trans by modifying the levels of the replicase.

In general, RNA represents an attractive alternative to DNA in order to circumvent the potential safety risks connected with the use of DNA in the therapy of humans and animals. The advantages of a therapeutic use of RNA include transient expression and a non-transforming character, and RNA does not need to enter the nucleus in order to be expressed, thereby minimizing the risk of oncogenesis.

Despite these advantages, the use of RNA for clinical applications has been restricted especially because of instability of RNA, and the associated short half-life of RNA. In the present invention the short half-life of RNA can be compensated by a system that drives replication of RNA in a host cell or an organism. In addition to that, the present invention provides specific RNA modifications, formulations, vehicles and modes of delivery that are advantageous for RNA stability. These will be described below. Indeed, when the RNA of the system of the present invention is introduced into a cell or an animal, efficient expression of the genetic information is achieved.

It is an advantage of the present invention compared to prior art approaches that transcription of a DNA template and transport of a transcript from the nucleus into the cytosol is dispensable. This eliminates the dependence on the proper functioning of a DNA-dependent RNA polymerase and on mRNA transport. Instead, the replicase construct of the present invention is immediately available for translation.

As described herein, the system of the present invention is suitable for efficient production of a desired polypeptide (e.g. transgene) in a host cell or host organism. It is one advantage of the present invention that higher transgene expression can be achieved than in the case of full length replicons suitable for replication in cis. It is a further advantage of the system of the present invention that high-level expression of a gene of interest can be achieved in wild-type primary cells (see Example 2) and in living animals, i.e. in vivo (Examples 5 and 6). This is a significant advantage compared to prior art systems which depend on engineered cell lines expressing a DNA-dependent RNA polymerase of bacteriophage origin, the T7 RNA polymerase (Spuul et al., J. Virol., 2011, vol. 85, pp. 4739-4751; Sanz et al., Cellular Microbial., 2015, vol. 17, pp. 520-541). Mammalian cells do not typically express the T7 RNA polymerase, unless specifically engineered (Buchholz et al., J. Virol., 1999, vol. 73, pp. 251-259). In summary, the RNA-based system of the present invention is advantageous over conventional gene delivery or gene therapy approaches.

The system of the present invention can be readily prepared. For example, the RNA molecules may be transcribed in vitro from a DNA template. In one embodiment, the RNA of the present invention is in vitro transcribed RNA (IVT-RNA). Thus in one embodiment, the system of the present invention comprises IVT-RNA. Preferably, all RNA molecules of the system of the present invention are IVT-RNA. In vitro-transcribed RNA (IVT-RNA) is of particular interest for therapeutic approaches.

The system of the present invention comprises at least two nucleic acid molecules. Thus, it may comprise two or more, three or more, four or more, five or more, six or more, seven or more, eight or more, nine or more, or ten or more nucleic acid molecules. In a preferred embodiment, it contains exactly two nucleic acid molecules, preferably RNA molecules, the replicon and the replicase construct. In alternative preferred embodiments, the system comprises, in addition to the replicase construct, more than one replicon, each preferably encoding at least one protein of interest. In these embodiments, the replicase encoded by the replicase construct can act on each replicon to drive replication and production of subgenomic transcripts, respectively. For example, each replicon may encode a pharmaceutically active peptide or protein. This is advantageous e.g. if vaccination of a subject against several different antigens is desired.

Preferably, the system of the invention is not capable to form virus particles, in particular next-generation virus particles. Preferably, the replicase construct of the present invention is not capable of self-replication in a target cell or target organism.

While aspects and advantages of RNA are described herein, it is, in some embodiments, alternatively possible that the system of the present invention comprises one or more DNA molecules. Any one or more nucleic acid molecules of the system of the present invention may, in some embodiments, be a DNA molecule. It is possible that the replicase construct and/or the replicon are a DNA molecule. In the case of a DNA molecule, a promoter for a DNA-dependent RNA polymerase is preferably present, thereby allowing transcription in an infected or vaccinated host cell or host organism.

Further embodiments and advantages of the system of the present invention are described in the following.

Characterization of the Replicase Construct

Preferably, the RNA construct for expressing alphavirus replicase (replicase construct) comprises an open reading frame (ORF) encoding an alphavirus replicase.

According to the present invention, "replicase" refers to an RNA-dependent RNA polymerase (RdRP). RdRP is an enzyme function. Replicase generally refers to a polypeptide or complex or association of more than one identical and/or non-identical proteins which is capable to catalyze the synthesis of (−) strand RNA based on a (+) strand RNA template, and/or which is capable to catalyze the synthesis of (+) strand RNA based on a (−) strand RNA template. The replicase may additionally have one or more additional functions, such as e.g. a protease (for auto-cleavage), helicase, terminal adenylyltransferase (for poly(A) tail addition), methyltransferase and guanylyltransferase (for providing a nucleic acid with a 5'-cap), nuclear localization sites, triphosphatase (Gould et al., 2010, Antiviral Res., vol. 87, pp. 111-124; Rupp et al., 2015, J. Gen. Virol., vol. 96, pp. 2483-500).

According to the invention, "alphavirus replicase" refers to an RNA replicase from an alphavirus, including an RNA replicase from a naturally occurring alphavirus and an RNA replicase from a variant or derivative of an alphavirus, such as from an attenuated alphavirus. In the context of the present invention, the terms "replicase" and "alphavirus replicase" are used interchangeably, unless the context dictates that any particular replicase is not an alphavirus replicase. The term "replicase" comprises all variants, in particular post-translationally modified variants, conformations, isoforms and homologs of alphavirus replicase, which are expressed by alphavirus-infected cells or which are expressed by cells that have been transfected with a nucleic acid that codes for replicase. Moreover, the term "replicase" comprises all forms of replicase that have been produced and can be produced by recombinant methods. For example, a replicase comprising a tag that facilitates detection and/or purification of the replicase in the laboratory, e.g. a myc-tag, a HA-tag or an oligohistidine tag (His-tag) may be produced by recombinant methods.

Optionally, the replicase is additionally functionally defined by the capacity of binding to any one or more of alphavirus conserved sequence element 1 (CSE1) or complementary sequence thereof, conserved sequence element 2 (CSE2) or complementary sequence thereof, conserved sequence element 3 (CSE3) or complementary sequence thereof, conserved sequence element 4 (CSE 4) or complementary sequence thereof. Preferably, the replicase is capable of binding to CSE 2 [i.e. to the (+) strand] and/or to CSE 4 [i.e. to the (+) strand], or of binding to the complement of CSE 1 [i.e. to the (−) strand] and/or to the complement of CSE 3 [i.e. to the (−) strand].

The origin of the replicase is not limited to any particular alphavirus. In a preferred embodiment, the alphavirus replicase is from Semliki Forest virus, including a naturally occurring Semliki Forest virus and a variant or derivative of Semliki Forest virus, such as an attenuated Semliki Forest virus. In an alternative preferred embodiment, the replicase is from Sindbis virus, including a naturally occurring Sindbis virus and a variant or derivative of Sindbis virus, such as an attenuated Sindbis virus. In an alternative preferred embodiment, the replicase is from Venezuelan equine encephalitis virus (VEEV), including a naturally occurring VEEV and a variant or derivative of VEEV, such as an attenuated VEEV.

Alphavirus replicase typically comprises or consists of alphavirus non-structural proteins (nsP). In this context, "non-structural proteins" refers to any one or more individual non-structural proteins of an alphavirus origin (nsP1, nsP2, nsP3, nsP4), or to a poly-protein comprising the polypeptide sequence of more than one non-structural proteins of alphavirus origin, e.g. nsP1234. In some embodiments, "non-structural protein" refers to nsP123. In other embodiments, "non-structural protein" refers to nsP1234. In other embodiments, "non-structural protein" refers to a complex or association of nsP123 (synonymously P123) and nsP4. In some embodiments, "non-structural protein" refers to a complex or association of nsP1, nsP2, and nsP3. In some embodiments, "non-structural protein" refers to a complex or association of nsP1, nsP2, nsP3 and nsP4. In some embodiments, "non-structural protein" refers to a complex or association of any one or more selected from the group consisting of nsP1, nsP2, nsP3 and nsP4.

Preferably, a "complex or association" is a functional ensemble of a multitude of elements. In the context of the alphavirus replicase, the term "complex or association" describes a multitude of at least two protein molecules, of which at least one is an alphavirus non-structural protein, wherein the complex or association has RNA-dependent RNA polymerase (RdRP) activity. The complex or association can consist of multiple different proteins (heteromultimer) and/or of multiple copies of one particular protein (homomultimer). In the context of a multimer or a multitude, "multi" means more than one, such as two, three, four, five, six, seven, eight, nine, ten, or more than ten.

A complex or association can also comprise proteins from more than one different alphavirus. For example, in a complex or association according to the invention which comprises different alphavirus non-structural proteins, it is not required that all non-structural proteins originate from the same alphavirus. Heterologous complexes or associations are equally comprised in the present invention. Merely for illustrative purposes, a heterologous complex or association may comprise one or more non-structural proteins (e.g. nsP1, nsP2) from a first alphavirus (e.g. Sindbis virus), and one or more non-structural proteins (nsP3, nsP4) from a second alphavirus (e.g. Semliki Forest virus).

The terms "complex" or "association" refer to two or more same or different protein molecules that are in spatial proximity. Proteins of a complex are preferably in direct or indirect physical or physicochemical contact with each other. A complex or association can consist of multiple different proteins (heteromultimer) and/or of multiple copies of one particular protein (homomultimer).

The term "replicase" includes each and every co- or post-translationally modified form, including carbohydrate-modified (such as glycosylated) and lipid-modified forms of the alphavirus non-structural proteins.

The term "replicase" includes each and every functional fragment of an alphavirus replicase. A fragment is functional when it functions as RNA-dependent RNA polymerase (RdRP).

In some embodiments, the replicase is capable of forming membranous replication complexes and/or vacuoles in cells in which the replicase is expressed.

Preferably the replicase construct comprises the coding region(s) for the replicase as defined above. The coding region(s) may consist of one or more open reading frame(s).

In one embodiment, the replicase construct encodes all of alphavirus nsP1, nsP2, nsP3 and nsP4. In one embodiment, the replicase construct encodes alphavirus nsP1, nsP2, nsP3 and nsP4 as one single, optionally cleavable polyprotein: nsP1234, encoded by one single open reading frame. In one embodiment, the replicase construct encodes alphavirus nsP1, nsP2 and nsP3 as one single, optionally cleavable polyprotein: nsP123, encoded by one single open reading frame. In that embodiment, nsP4 may be encoded separately.

Preferably, the replicase construct of the present invention does not comprise an alphavirus subgenomic promoter.

Preferably, the replicase construct is an mRNA molecule. The mRNA molecule preferably comprises neither CSE 1 nor CSE 4. Without wishing to be bound by theory, it is envisaged that such mRNA will not compete with the replicon for binding of replicase, so that the replicon can be replicated very efficiently by the replicase.

The RNA of the replicase construct is preferably not double-stranded, preferably it is single stranded, more preferably (+) strand RNA. The replicase is encoded by an open reading frame on the replicase construct.

In one embodiment, the replicase construct of the present invention is an intron-free RNA, preferably an intron-free mRNA. Preferably, the replicase construct is a naturally intron-free RNA (mRNA). For example, an intron-free RNA (mRNA) is obtainable by synthesis in vitro, e.g. by in vitro transcription. In one embodiment, the replicase construct comprises an open reading frame encoding nsP1234 which does not comprise an intron. In one embodiment, the replicase construct comprises an open reading frame encoding nsP123 which does not comprise an intron. Preferably, the replicase construct does not comprise an intron obtained from the rabbit beta-globin gene (as described in WO 2008/119827 A1).

An "intron" as used herein, is defined as a non-coding section of precursor mRNA (pre-mRNA), that is being removed, i.e. spliced out of the RNA, prior to translation of the coding sequence of the RNA into a polypeptide. Once the introns have been spliced out of a pre-mRNA, the resulting mRNA sequence is ready to be translated into a polypeptide. In other words, the nucleotide sequence of the intron is typically not translated into a protein. An intron-free mRNA is an mRNA containing in consecutive order the codons (base triplets) for translation into a polypeptide. An intron-free mRNA may either be naturally intron-free (i.e. be initially synthesized as intron-free mRNA, e.g. in a cell or in vitro transcription), or can mature into an intron-free mRNA by splicing of an intron-containing pre-mRNA. Naturally intron-free in vitro transcribed RNA is preferred in the present invention.

The replicase construct of the present invention differs from alphaviral genomic RNA at least in that it is not capable of self-replication and/or that it does not comprise an open reading frame under the control of a sub-genomic promoter. When unable to self-replicate, the replicase construct may also be termed "suicide construct".

Preferably, the replicase construct of the present invention is not associated with alphavirus structural proteins. Preferably the replicase construct is not packaged by alphavirus structural proteins. More preferably, the replicase construct is not packaged in a viral particle. Preferably, the replicase construct is not associated with viral proteins (virus protein-free system). A virus protein-free system provides an advantage compared to helper-virus based system of the prior art, e.g. by Bredenbeek et al., supra.

Preferably, the replicase construct lacks at least one conserved sequence element (CSE) that is required for (−) strand synthesis based on a (+) strand template, and/or for (+) strand synthesis based on a (−) strand template. More preferably, the replicase construct does not comprise any conserved sequence elements (CSEs) derived from an alphavirus. In particular, among the four CSEs of alphavirus (Strauss & Strauss, Microbiol. Rev., 1994, vol. 58, pp. 491-562; Jose et al., Future Microbiol., 2009, vol. 4, pp. 837-856), any one or more of the following CSEs are preferably not present on the replicase construct.

CSE 1, believed to function as a promoter for (+) strand synthesis based on a (−) strand template in alphavirus found in nature;

CSE 2, believed to function as a promoter for (−) strand synthesis based on a (+) strand genomic RNA of an alphavirus found in nature;

CSE 3, believed to contribute to efficient transcription of the subgenomic (+) strand RNA in alphavirus found in nature;

CSE 4, believed to function as a core-promoter for initiation of (−) strand synthesis based on a (+) strand genomic RNA in alphavirus found in nature.

In one embodiment, CSE 1, CSE 3 and CSE 4 are not present, and CSE 2 may or may not be present.

Particularly in the absence of any one or more alphaviral CSE, the replicase construct of the present invention resembles typical eukaryotic mRNA much more than it resembles alphaviral genomic RNA.

In one embodiment, the replicase construct of the present invention is an isolated nucleic acid molecule.

Cap

The RNA construct for expressing alphavirus replicase (replicase construct) comprises a 5'-cap. The terms "5'-cap", "cap", "5'-cap structure", "cap structure" are used synonymously to refer to a dinucleotide that is found on the 5' end of some eukaryotic primary transcripts such as precursor messenger RNA. A 5'-cap is a structure wherein a (optionally modified) guanosine is bonded to the first nucleotide of an mRNA molecule via a 5' to 5' triphosphate linkage (or modified triphosphate linkage in the case of certain cap analogs). The terms can refer to a conventional cap or to a cap analog. For illustration, some particular cap dinucleotides (including cap analog dinucleotides) are shown in FIG. 2.

"RNA which comprises a 5'-cap" or "RNA which is provided with a 5'-cap" or "RNA which is modified with a 5'-cap" or "capped RNA" refers to RNA which comprises a 5'-cap. For example, providing an RNA with a 5'-cap may be achieved by in vitro transcription of a DNA template in presence of said 5'-cap, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus. In capped RNA, the 3' position of the first base of a (capped) RNA molecule is linked to the 5' position of the subsequent base of the RNA molecule ("second base") via a phosphodiester bond. For illustration, in FIG. 1, the position of the cap in nucleic acid molecules according to the present invention is symbolized by the letter C.

The term "conventional 5'-cap" refers to a naturally occurring 5'-cap, preferably to the 7-methylguanosine cap. In the 7-methylguanosine cap, the guanosine of the cap is a modified guanosine wherein the modification consists of a methylation at the 7-position (top of FIG. 2).

In the context of the present invention, the term "5'-cap analog" refers to a molecular structure that resembles a conventional 5'-cap, but is modified to possess the ability to stabilize RNA if attached thereto, preferably in vivo and/or in a cell. A cap analog is not a conventional 5'-cap.

The present invention is distinguished from prior art trans-replication systems in that translation of the replicase is driven by a 5'-cap on the replicase construct. The present inventors found that specifically the 5'-cap on the replicase construct has a very positive influence, not only on expression of the replicase, but also on performance of the system as a whole: very efficient production of the gene of interest encoded in trans can be achieved (see examples). In one embodiment, the replicase construct of the present invention does not comprise an internal ribosomal entry site (IRES) element.

In general, an internal ribosome entry site, abbreviated IRES, is a nucleotide sequence that allows for translation initiation from a messenger RNA (mRNA) from a position different from the 5' end of the mRNA sequence, such as e.g. from a position in the middle of a mRNA sequence. The terms IRES and IRES element are used interchangeably herein. IRES elements are found in eukaryotes, as well as in viruses capable of infecting eukaryotes. However, the mechanism of viral IRES function to date is better characterized than the mechanism of eukaryotic IRES function (Lopez-Lastra et al., 2005, Biol. Res., vol. 38, pp. 121-146). It has been suggested to use an IRES for driving expression of an alphavirus replicase in eukaryotic cells (e.g. Sanz et al., Cellular Microbiol., 2015, vol. 17, pp. 520-541). The present inventors show that in various embodiments efficient gene expression of a gene encoded on a trans-replicon can be achieved when the replicase construct does not comprise an IRES (see Examples 1 to 6). Thus, in one embodiment, the RNA construct for expressing alphavirus replicase (replicase construct) does not comprise an internal ribosomal entry site (IRES) element. Preferably, translation of the replicase is not driven by an IRES element. It is known that the levels of translated protein encoded in an open reading frame downstream of an IRES vary widely and depend on the type and sequence of the particular IRES and on details of the experimental setup (reviewed in Balvay et al., 2009, Biochim. Biophys. Acta, vol. 1789, pp. 542-557). In the case of gene expression from IRES-containing RNA in the prior art, it was observed that gene expression is less efficient from larger trans-replicons, compared to a short trans-replicon (Spuul et al., J. Viral., 2011, vol. 85, pp. 4739-4751) and that the size of membranous replication complexes typical for alphavirus replicase depends on the length of the trans-replicon (Kallio et al., 2013, J. Virol., vol. 87, pp. 9125-9134). IRES-containing RNAs were also transcribed in vitro and transfected into cells together with trans-replicons (Sanz et al., Cellular Microbiol., 2015, vol. 17, pp. 520-541). This study suggested that the use of in vitro transcribed IRES-containing mRNA is functional to express replicase in a cell, and to mediate replication of a replicon in trans.

The approach of the present invention is markedly different from the prior art: Spuul et al., supra, presumed that their RNA (produced in situ in transfected cells) is uncapped. Spuul et al. did not foresee the incorporation of a cap into the uncapped RNA: they chose an alternative approach and incorporated an internal ribosomal entry site (IRES) element downstream of a T7 promoter; according to that reference, the IRES element is implicated in enhancement of expression of the presumably uncapped RNA. The replicase construct of the present invention also differs from the IRES-containing uncapped in vitro transcribed RNA encoding nsP1-4, described by Sanz et al., supra.

The substitution of the IRES (as used by Sanz et al., supra, and Spuul et al., supra) by a 5'-cap in the present invention is a particular modification of an RNA molecule that does not affect the sequence of the polypeptide that is encoded by the RNA molecule (non-polypeptide-sequence modifying modification).

In principle, any coding RNA is amenable to non-polypeptide-sequence modifying modifications. In modern molecular biology, possible effects of non-polypeptide-sequence modifying modifications e.g. on efficiency of gene expression, have been studied in several systems. However, no generally applicable rules have been established as to what type of non-polypeptide-sequence modifying modification should be selected in order to achieve efficient gene expression, e.g. improved gene expression compared to a non-modified sequence. Therefore, the selection of an appropriate non-polypeptide-sequence modifying modification for any particular coding nucleic acid and/or any particular expression system is a challenging task. In the art, a variety of different non-polypeptide-sequence modifying modifications have been described. For example, for eukaryotic messenger RNAs, non-polypeptide-sequence modifying modifications that have been studied include the selection of particular untranslated regions (UTRs, as described e.g. in WO 2013/143699 A1, WO 2013/143698 A1; Holtkamp et al., Blood, 2006, vol. 108, pp. 4009-4017), the introduction of intron, e.g. the rabbit beta-globin intron II sequence (e.g. Li et al., J. Exp. Med., 1998, vol. 188, pp. 681-688), or silent modification of the coding sequence, e.g. by adaptation to the preferential codon usage of the host cell or host organism without altering the encoded polypeptide sequence (silent modification, generally described e.g. in WO 2003/085114 A1). To the knowledge of the present inventors, no systematic comparative studies on the influence of various non-polypeptide-sequence modifying modifications in alphavirus-based expression systems are presently available.

In the research conducted to arrive at the present invention, various approaches involving e.g. non-polypeptide-sequence modifying modifications were diligently examined, and as a result, it was surprisingly found that specifically the substitution of an IRES by a 5'-cap on the replicase construct has a beneficial effect in trans, i.e. a beneficial effect at the level of the replicon in trans: production of the protein of interest encoded by the replicon according to the present invention is efficient when a cap is present on the replicase construct. This is remarkable, particularly since an alternative non-polypeptide-sequence modifying modification, i.e. adaptation of modification of the coding sequence, failed to improve the performance of the system of the present invention: in contrast, the efficiency of production of the protein of interest encoded by the replicon was even reduced. This is illustrated in Example 4. Thus, for the case of a trans-replication system based on alphavirus RNA elements, inclusion of a 5'-cap on the replicase construct is a particularly advantageous non-polypeptide-sequence modifying modification. The findings of the present invention are also surprising in view of WO 2008/119827 A1, which describes that a codon-adapted Semliki Forest replicase is expressed in transfected BHK-21 host cells, and which concludes that codon-optimized SFV replicase is highly active and is capable to enhance reporter gene expression in trans. Thus, WO 2008/119827 A1 points in a direction different from the present invention, suggesting that that an alternative non-polypeptide-sequence modifying modification, i.e. introduction of an intron into the coding sequence of the replicase, is helpful for efficient replicase expression.

In eukaryotic mRNA, the presence of a 5'-cap is thought to play a role inter alia in regulation of nuclear export of mRNA and in processing, particularly promotion of 5' proximal intron excision (Konarska et al., 2014, Cell, vol. 38, pp. 731-736). The replicase construct of the present invention typically neither needs to be exported from the nucleus, nor processed. Nevertheless, it was surprisingly found that the presence of a 5'-cap on the replicase construct is advantageous.

For the case of eukaryotic mRNA, the 5'-cap has also been generally described to be involved in efficient translation of mRNA: in general, in eukaryotes, translation is initiated only at the 5' end of a messenger RNA (mRNA) molecule, unless an IRES is present. Eukaryotic cells are capable of providing an RNA with a 5'-cap during transcription in the nucleus: newly synthesized mRNAs are usually modified with a 5'-cap structure, e.g. when the transcript reaches a length of 20 to 30 nucleotides. First, the 5' terminal nucleotide pppN (ppp representing triphosphate; N representing any nucleoside) is converted in the cell to 5' GpppN by a capping enzyme having RNA 5'-triphosphatase and guanylyltransferase activities. The GpppN may subsequently be methylated in the cell by a second enzyme with (guanine-7)-methyltransferase activity to form the mono-methylated m$^7$GpppN cap. In one embodiment, the 5'-cap used in the present invention is a natural 5'-cap.

In the present invention, a natural 5'-cap dinucleotide is typically selected from the group consisting of a non-methylated cap dinucleotide (G(5')ppp(5')N; also termed GpppN) and a methylated cap dinucleotide ((m$^7$G(5')ppp(5')N; also termed m$^7$GpppN). m$^7$GpppN (wherein N is G) is represented by the following formula:

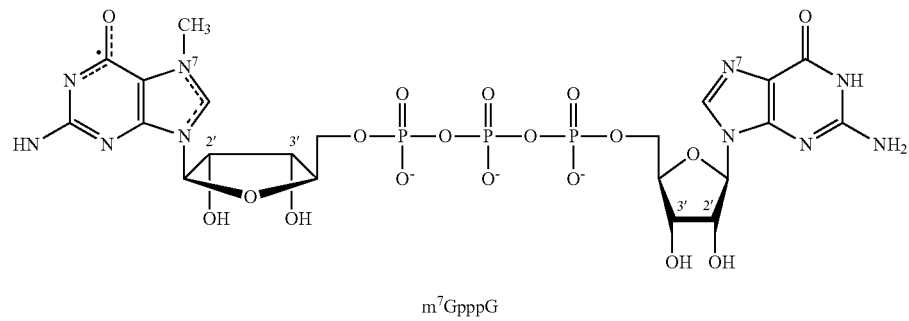

m$^7$GpppG

The replicase construct of the present invention does not depend on a capping machinery in a host cell. It is envisaged that, when transfected into a host cell, the replicase construct of the present invention does typically not localize to the cell nucleus, i.e. the site where capping would otherwise occur in typical eukaryotic cells.

Without wishing to be bound by theory, and in analogy to the IRES on prior art constructs, it may be envisaged that the 5'-cap on the replicase construct is helpful for triggering initiation of translation of the replicase. It may be envisaged that the eukaryotic translation initiation factor eIF4E is involved in associating capped mRNA according to the present invention with the ribosome. It was surprisingly found by the inventors of the present invention that the presence of a 5'-cap significantly increases the performance. The replicase construct of the present invention thus comprises a 5'-cap.

Presence of the 5'-cap also provides unexpected synergistic effects in the trans-replication system of the present invention: as shown in the examples, capped replicase constructs trigger production of a protein of interest more efficiently when the capped replicase construct is provided in trans with respect to the replicon RNA (see e.g. Example 1). Thus, the synergistic effect of a 5'-cap and of replication in trans, i.e. superior to replication in cis, is demonstrated herein.

The capped RNA of the present invention can be prepared in vitro, and therefore, does not depend on a capping machinery in a host cell. The most frequently used method to make capped RNAs in vitro is to transcribe a DNA template with either a bacterial or bacteriophage RNA polymerase in the presence of all four ribonucleoside triphosphates and a cap dinucleotide such as $m^7G(5')ppp(5')G$ (also called $m^7GpppG$). The RNA polymerase initiates transcription with a nucleophilic attack by the 3'-OH of the guanosine moiety of $m^7GpppG$ on the α-phosphate of the next templated nucleoside triphosphate (pppN), resulting in the intermediate $m^7GpppGpN$ (wherein N is the second base of the RNA molecule). The formation of the competing GTP-initiated product pppGpN is suppressed by setting the molar ratio of cap to GTP between 5 and 10 during in vitro transcription.

expression constructs which preferably do not contain any modified nucleotides, and which comprise a natural cap, $(m^7G(5')ppp(5')G$; also called $m^7GpppG$, that is optionally added by the commercially available ScriptCap m7G Capping System (Epicentre Biotechnologies).

For messenger RNA, some cap analogs (synthetic caps) have been generally described to date, and they can all be used in the context of the present invention. Preferably, a cap analog is used that can only be incorporated into an RNA chain in one orientation. Pasquinelli et al. (1995, RNA J., vol., 1, pp. 957-967) demonstrated that during in vitro transcription, bacteriophage RNA polymerases use the 7-methylguanosine unit for initiation of transcription, whereby around 40-50% of the transcripts with cap possess the cap dinucleotide in a reverse orientation (i.e., the initial reaction product is $Gpppm^7GpN$). Compared to the RNAs with a correct cap, RNAs with a reverse cap are not functional with respect to translation of the encoded proteins. Thus, it is desirable to incorporate the cap in the correct orientation, i.e., resulting in an RNA with a structure essentially corresponding to $m^7GpppGpN$ etc. It has been shown that the reverse integration of the cap-dinucleotide is inhibited by the substitution of either the 2'- or the 3'-OH group of the methylated guanosine unit (Stepinski et al., 2001; RNA J., vol. 7, pp. 1486-1495; Peng et al., 2002; Org. Lett., vol. 24, pp. 161-164). RNAs which are synthesized in presence of such "anti reverse cap analogs" are translated more efficiently than RNAs which are in vitro transcribed in presence of the conventional 5'-cap $m^7GpppG$. To that end, one cap analog in which the 3' OH group of the methylated guanosine unit is replaced by $OCH_3$ is described e.g. by Holtkamp et al., 2006, Blood, vol. 108, pp. 4009-4017 (7-methyl(3'-O-methyl)GpppG; anti-reverse cap analog (ARCA)). ARCA is a suitable cap dinucleotide according to the present invention.

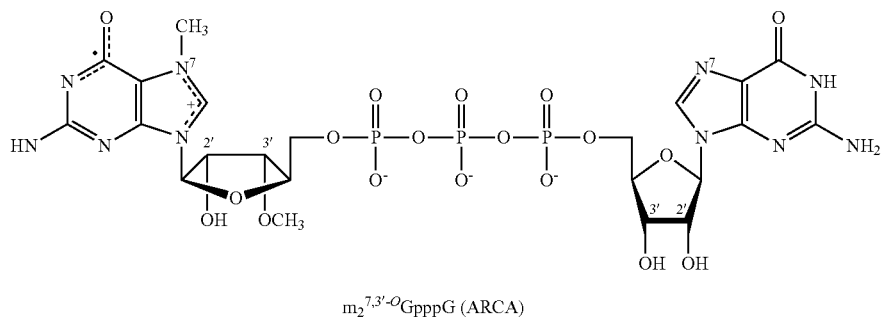

$m_2^{7,3'-O}GpppG$ (ARCA)

In preferred embodiments of the present invention, the 5'-cap is a 5'-cap analog. These embodiments are particularly suitable if the RNA is obtained by in vitro transcription, e.g. is an in vitro transcribed RNA (IVT-RNA). Cap analogs have been initially described to facilitate large scale synthesis of RNA transcripts by means of in vitro transcription.

In contrast to previously described engineered alphavirus replication systems (e.g. WO 2008/119827 A1, WO 2012/006376 A2), the replicase construct of the present invention preferably comprises a cap analog. Thus, translation of the replicase of the system of the present invention is preferably driven by a cap analog. Ideally, a cap analog is selected that is associated with higher translation efficiency and/or increased resistance to in vivo degradation and/or increased resistance to in vitro degradation. The present invention thus provides an approach which markedly differs from the prior art (WO 2012/006376 A2), which describes alphaviral In a preferred embodiment of the present invention, the RNA of the present invention is essentially not susceptible to decapping. This is important because, in general, the amount of protein produced from synthetic mRNAs introduced into cultured mammalian cells is limited by the natural degradation of mRNA. One in vivo pathway for mRNA degradation begins with the removal of the mRNA cap. This removal is catalyzed by a heterodimeric pyrophosphatase, which contains a regulatory subunit (Dcp1) and a catalytic subunit (Dcp2). The catalytic subunit cleaves between the α and β phosphate groups of the triphosphate bridge. In the present invention, a cap analog may be selected or present that is not susceptible, or less susceptible, to that type of cleavage. A suitable cap analog for this purpose may be selected from a cap dinucleotide according to formula (I):

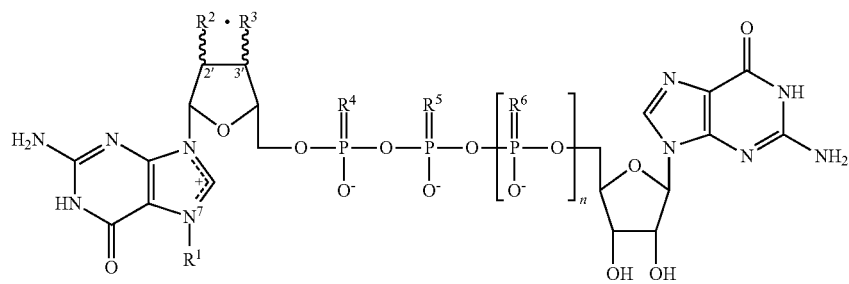

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the hydrogen atom at position 4' of the ring to which $R^2$ is attached to form —O—$CH_2$— or —$CH_2$—O—, $R^5$ is selected from the group consisting of S, Se, and $BH_3$, $R^4$ and $R^6$ are independently selected from the group consisting of O, S, Se, and $BH_3$, and n is 1, 2, or 3.

Preferred embodiments for $R^1$, $R^2$, $R^3$, $R^4$, $R^5$, $R^6$ are disclosed in WO 2011/015347 A1 and may be selected accordingly in the present invention. In one embodiment of the present invention, $R^1$ is methyl and $R^2$ and $R^3$ are independently hydroxy or methoxy.

For example, in a preferred embodiment of the present invention, the RNA of the present invention comprises a phosphorothioate-cap-analog. Phosphorothioate-cap-analogs are specific cap analogs in which one of the three non-bridging O atoms in the triphosphate chain is replaced with an S atom, i.e. one of $R^4$, $R^5$ or $R^6$ in Formula (I) is S. Phosphorothioate-cap-analogs have been described by J. Kowalska et al., 2008, RNA, vol. 14, pp. 1119-1131, as a solution to the undesired decapping process, and thus to increase the stability of RNA in vivo. In particular, the substitution of an oxygen atom for a sulphur atom at the beta-phosphate group of the 5'-cap results in stabilization against Dcp2. In that embodiment, which is preferred in the present invention, $R^5$ in Formula (I) is S; and $R^4$ and $R^6$ are O.

In a further preferred embodiment of the present invention, the RNA of the present invention comprises a phosphorothioate-cap-analog wherein the phosphorothioate modification of the RNA 5'-cap is combined with an "anti-reverse cap analog" (ARCA) modification. Respective ARCA-phosphorothioate-cap-analogs are described in WO 2008/157688 A2, and they can all be used in the RNA of the present invention. In that embodiment, at least one of $R^2$ or $R^3$ in Formula (I) is not OH, preferably one among $R^2$ and $R^3$ is methoxy (OCH3), and the other one among $R^2$ and $R^3$ is preferably OH. In a preferred embodiment, an oxygen atom is substituted for a sulphur atom at the beta-phosphate group (so that $R^5$ in Formula (I) is S; and $R^4$ and $R^6$ are O). It is believed that the phosphorothioate modification of the ARCA ensures that the α, β, and γ phosphate and phosphorothioate groups are precisely positioned within the active sites of cap-binding proteins in both the translational and decapping machinery. At least some of these analogs are essentially resistant to pyrophosphatase Dcp1/Dcp2. Phosphorothioate-modified ARCAs were described to have a much higher affinity for eIF4E than the corresponding ARCAs lacking a phosphorothioate group.

A respective cap analog that is particularly preferred in the present invention, i.e., $m_2^{7,2'-O}Gpp_sPG$, is termed beta-S-ARCA (WO 2008/157688 A2; Kuhn et al., Gene Ther., 2010, vol. 17, pp. 961-971). Thus, in one embodiment of the present invention, the replicase construct of the present invention is modified with beta-S-ARCA. beta-S-ARCA is represented by the following structure:

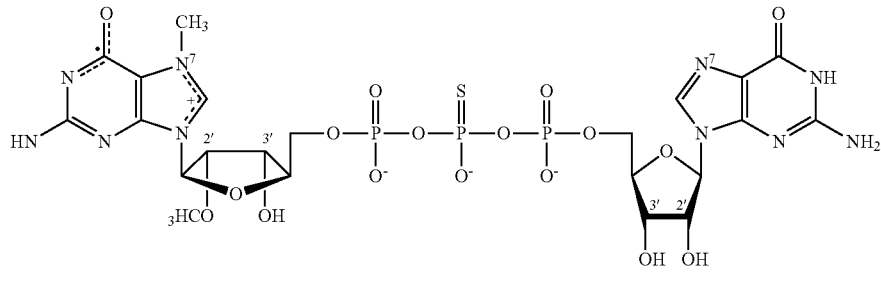

$m_2^{7,2'-O}GpppG$ (beta-S-ARCA)

In general, the replacement of an oxygen atom for a sulphur atom at a bridging phosphate results in phosphorothioate diastereomers which are designated D1 and D2, based on their elution pattern in HPLC. Briefly, the D1 diastereomer of beta-S-ARCA" or "beta-S-ARCA(D1)" is the diastereomer of beta-S-ARCA which elutes first on an HPLC column compared to the D2 diastereomer of beta-S-ARCA (beta-S-ARCA(D2)) and thus exhibits a shorter retention time. Determination of the stereochemical configuration by HPLC is described in WO 2011/015347 A1.

In a first particularly preferred embodiment of the present invention, the replicase construct of the present invention is modified with the beta-S-ARCA(D2) diastereomer. The two diastereomers of beta-S-ARCA differ in sensitivity against nucleases. It has been shown that RNA carrying the D2 diastereomer of beta-S-ARCA is almost fully resistant against Dcp2 cleavage (only 6% cleavage compared to RNA which has been synthesized in presence of the unmodified ARCA 5'-cap), whereas RNA with the beta-S-ARCA(D1) 5'-cap exhibits an intermediary sensitivity to Dcp2 cleavage (71% cleavage). It has further been shown that the increased stability against Dcp2 cleavage correlates with increased protein expression in mammalian cells. In particular, it has been shown that RNAs carrying the beta-S-ARCA(D2) cap are more efficiently translated in cells than RNAs carrying the beta-S-ARCA(D1) cap. Therefore, in one embodiment of the present invention, the replicase construct of the present invention is modified with a cap analog according to Formula (I), characterized by a stereochemical configuration at the P atom comprising the substituent $R^5$ in Formula (I) that corresponds to that at the $P_\beta$ atom of the D2 diastereomer of beta-S-ARCA. In that embodiment, $R^5$ in Formula (I) is S; and $R^4$ and $R^6$ are O. Additionally, at least one of $R^2$ or $R^3$ in Formula (I) is preferably not OH, preferably one among $R^2$ and $R^3$ is methoxy (OCH3), and the other one among $R^2$ and $R^3$ is preferably OH.

In a second particularly preferred embodiment, the replicase construct of the present invention is modified with the beta-S-ARCA(D1) diastereomer. This embodiment is particularly suitable for transfer of capped RNA into immature antigen presenting cells, such as for vaccination purposes. It has been demonstrated that the beta-S-ARCA(D1) diastereomer, upon transfer of respectively capped RNA into immature antigen presenting cells, is particularly suitable for increasing the stability of the RNA, increasing translation efficiency of the RNA, prolonging translation of the RNA, increasing total protein expression of the RNA, and/or increasing the immune response against an antigen or antigen peptide encoded by said RNA (Kuhn et al., 2010, Gene Ther., vol. 17, pp. 961-971). Therefore, in an alternative embodiment of the present invention, the replicase construct of the present invention is modified with a cap analog according to Formula (I), characterized by a stereochemical configuration at the P atom comprising the substituent $R^5$ in Formula (I) that corresponds to that at the $P_\beta$ atom of the D1 diastereomer of beta-S-ARCA. Respective cap analogs and embodiments thereof are described in WO 2011/015347 A1 and Kuhn et al., 2010, Gene Ther., vol. 17, pp. 961-971. Any cap analog described in WO 2011/015347 A1, wherein the stereochemical configuration at the P atom comprising the substituent $R^5$ corresponds to that at the $P_\beta$ atom of the D1 diastereomer of beta-S-ARCA, may be used in the present invention. Preferably, $R^5$ in Formula (I) is S; and $R^4$ and $R^6$ are O. Additionally, at least one of $R^2$ or $R^3$ in Formula (I) is preferably not OH, preferably one among $R^2$ and $R^3$ is methoxy (OCH3), and the other one among $R^2$ and $R^3$ is preferably OH.

In one embodiment, the replicase construct of the present invention is modified with a 5'-cap structure according to Formula (I) wherein any one phosphate group is replaced by a boranophosphate group or a phosphoroselenoate group. Such caps have increased stability both in vitro and in vivo. Optionally, the respective compound has a 2'-O— or 3'-O-alkyl group (wherein alkyl is preferably methyl); respective cap analogs are termed $BH_3$-ARCAs or Se-ARCAs. Compounds that are particularly suitable for capping of mRNA include the β-$BH_3$-ARCAs and β-Se-ARCAs, as described in WO 2009/149253 A2. For these compounds, a stereochemical configuration at the P atom comprising the substituent $R^5$ in Formula (I) that corresponds to that at the $P_\beta$ atom of the D1 diastereomer of beta-S-ARCA is preferred.

UTR

The term "untranslated region" or "UTR" relates to a region which is transcribed but is not translated into an amino acid sequence, or to the corresponding region in an RNA molecule, such as an mRNA molecule. A 3'-UTR, if present, is located at the 3' end of a gene, downstream of the termination codon of a protein-encoding region, but the term "3'-UTR" does preferably not include the poly(A) tail. Thus, the 3'-UTR is upstream of the poly(A) tail (if present), e.g. directly adjacent to the poly(A) tail.

A 5'-UTR, if present, is located at the 5' end of a gene, upstream of the start codon of a protein-encoding region. A 5'-UTR is downstream of the 5'-cap (if present), e.g. directly adjacent to the 5'-cap.

5'- and/or 3'-untranslated regions may, according to the invention, be functionally linked to an open reading frame, so as for these regions to be associated with the open reading frame in such a way that the stability and/or translation efficiency of the RNA comprising said open reading frame are increased.

An untranslated region (UTR) can be present 5' (upstream) of the open reading frame encoding the replicase (5'-UTR) and/or 3' (downstream) of the open reading frame encoding the replicase (3'-UTR). In a preferred embodiment, the RNA construct for expressing alphavirus replicase (replicase construct) comprises (1) a 5' UTR,
(2) an open reading frame encoding the replicase, and
(3) a 3' UTR.

Specifically in an embodiment of the replicase construct of the present invention, the term "3'-UTR" relates to a region which is located 3' of the coding region for replicase, and the term "5'-UTR" relates to a region which is located 5' of the coding region for replicase.

UTRs are implicated in stability and translation efficiency of RNA, a prerequisite for an effective immune response using RNA-based vaccines. Both can be improved, besides structural modifications concerning the 5'-cap and/or the 3' poly(A)-tail as described herein, by selecting specific 5' and/or 3' untranslated regions (UTRs). Sequence elements within the UTRs are generally understood to influence translational efficiency (mainly 5'-UTR) and RNA stability (mainly 3'-UTR). It is preferable that a 5'-UTR is present that is active in order to increase the translation efficiency and/or stability of a nucleic acid sequence. Independently or additionally, it is preferable that a 3'-UTR is present that is active in order to increase the translation efficiency and/or stability of a nucleic acid sequence.

The term "nucleic acid sequence which is active in order to increase the translation efficiency and/or stability of a nucleic acid sequence", with reference to a first nucleic acid sequence (e.g. a UTR), means that the first nucleic acid sequence is capable of modifying, in a common transcript with the second nucleic acid sequence, the translation efficiency and/or stability of said second nucleic acid sequence in such a way that said translation efficiency and/or stability is increased in comparison with the translation efficiency and/or stability of said second nucleic acid sequence in the absence of said first nucleic acid sequence. In this context, the term "translation efficiency" relates to the amount of translation product provided by an RNA molecule within a particular period of time, and the term "stability" relates to the half-life of an RNA molecule.

Preferably, the replicase construct comprises a 5'-UTR and/or a 3'-UTR which is heterologous or non-native to the alphavirus from which the replicase is derived. This allows the untranslated regions to be designed according to the desired translation efficiency and RNA stability. Thus, heterologous or non-native UTRs allow for a high degree of flexibility, and this flexibility is advantageous compared to native alphaviral UTRs. In particular, while it is known that alphaviral (native) RNA also comprises a 5' UTR and/or a 3' UTR, alphaviral UTRs fulfil a dual function, i.e. (i) to drive RNA replication as well as (ii) to drive translation. While alphaviral UTRs were reported to be inefficient for translation (Berben-Bloemheuvel et al., 1992, Eur. J. Biochem., vol. 208, pp. 581-587), they cannot readily be replaced by more efficient UTRs because of their dual function. In the present invention, however, the 5'-UTR and/or 3'-UTR of the replicase construct can be selected independent of their potential influence on RNA replication.

Preferably, the replicase construct comprises a 5'-UTR and/or a 3'-UTR that is not of virus origin; particularly not of alphavirus origin. In one embodiment, the RNA comprises a 5'-UTR derived from a eukaryotic 5'-UTR and/or a 3'-UTR derived from a eukaryotic 3'-UTR.

A 5'-UTR according to the present invention can comprise any combination of more than one nucleic acid sequence, optionally separated by a linker. A 3'-UTR according to the present invention can comprise any combination of more than one nucleic acid sequence, optionally separated by a linker.

The term "linker" according to the invention relates to a nucleic acid sequence added between two nucleic acid sequences to connect said two nucleic acid sequences. There is no particular limitation regarding the linker sequence.

A 3'-UTR typically has a length of 200 to 2000 nucleotides, e.g. 500 to 1500 nucleotides. The 3'-untranslated regions of immunoglobulin mRNAs are relatively short (fewer than about 300 nucleotides), while the 3'-untranslated regions of other genes are relatively long. For example, the 3'-untranslated region of tPA is about 800 nucleotides in length, that of factor VIII is about 1800 nucleotides in length and that of erythropoietin is about 560 nucleotides in length.

The 3'-untranslated regions of mammalian mRNA typically have a homology region known as the AAUAAA hexanucleotide sequence. This sequence is presumably the poly(A) attachment signal and is frequently located from 10 to 30 bases upstream of the poly(A) attachment site.

3'-untranslated regions may contain one or more inverted repeats which can fold to give stem-loop structures which act as barriers for exoribonucleases or interact with proteins known to increase RNA stability (e.g. RNA-binding proteins).

The human beta-globin 3'-UTR, particularly two consecutive identical copies of the human beta-globin 3'-UTR, contributes to high transcript stability and translational efficiency (Holtkamp et al., 2006, Blood, vol. 108, pp. 4009-4017). Thus, embodiment, the replicase construct of the present invention comprises two consecutive identical copies of the human beta-globin 3'-UTR. Thus, it comprises in the 5' →3' direction: (a) optionally a 5'-UTR; (b) an open reading frame encoding a replicase; (c) a 3'-UTR; said 3'-UTR comprising two consecutive identical copies of the human beta-globin 3'-UTR, a fragment thereof, or a variant of the human beta-globin 3'-UTR or fragment thereof.

In one embodiment, the replicase construct of the present invention comprises a 3'-UTR which is active in order to increase the translation efficiency and/or stability of the replicase construct, but which is not the human beta-globin 3'-UTR, a fragment thereof, or a variant of the human beta-globin 3'-UTR or fragment thereof.

In one embodiment, the replicase construct of the present invention comprises a 5'-UTR which is active in order to increase the translation efficiency and/or stability of the replicase construct.

UTR-containing RNA according to the invention can be prepared e.g. by in vitro transcription. This may be achieved by genetically modifying expression of nucleic acid molecules of the invention (e.g. DNA) in such a way that they allow transcription of RNA with 5'-UTRs and/or 3'-UTRs.

Poly (A) Sequence

In one embodiment, the RNA construct for expressing alphavirus replicase (replicase construct) comprises a 3' poly(A) sequence.

In alphaviruses, a 3' poly(A) sequence of at least 11 consecutive adenylate residues, or at least 25 consecutive adenylate residues, is thought to be important for efficient synthesis of the minus strand. In particular, in alphaviruses, a 3' poly(A) sequence of at least 25 consecutive adenylate residues is understood to function together with conserved sequence element 4 (CSE 4) to promote synthesis of the (−) strand (Hardy & Rice, J. Virol., 2005, vol. 79, pp. 4630-4639). In the present invention, however, (−) strand synthesis of the replicase construct is typically not desired, and the poly(A) sequence serves primarily the functions of influencing RNA stability and protein translation in transfected eukaryotic cells. Indeed, it has been demonstrated that a 3' poly(A) sequence of about 120 A nucleotides has a beneficial influence on the levels of RNA in transfected eukaryotic cells, as well as on the levels of protein that is translated from an open reading frame that is present upstream (5') of the 3' poly(A) sequence (Holtkamp et al., 2006, Blood, vol. 108, pp. 4009-4017). According to the invention, in one embodiment, a poly(A) sequence comprises or essentially consists of or consists of at least 20, preferably at least 26, preferably at least 40, preferably at least 80, preferably at least 100 and preferably up to 500, preferably up to 400, preferably up to 300, preferably up to 200, and in particular up to 150, A nucleotides, and in particular about 120 A nucleotides. In this context "essentially consists of" means that most nucleotides in the poly(A) sequence, typically at least 50%, and preferably at least 75% by number of nucleotides in the "poly(A) sequence", are A nucleotides, but permits that remaining nucleotides are nucleotides other than A nucleotides, such as U nucleotides (uridylate), G nucleotides (guanylate), C nucleotides (cytidylate). In this context "consists of" means that all nucleotides in the poly(A) sequence, i.e. 100% by number of nucleotides in the poly(A) sequence, are A nucleotides. The term "A nucleotide" or "A" refers to adenylate.

The present invention provides for a 3' poly(A) sequence to be attached during RNA transcription, i.e. during preparation of in vitro transcribed RNA, based on a DNA template comprising repeated dT nucleotides (deoxythymidylate) in the strand complementary to the coding strand. The DNA sequence encoding a poly(A) sequence (coding strand) is referred to as poly(A) cassette.

In a preferred embodiment of the present invention, the 3' poly(A) cassette present in the coding strand of DNA essentially consists of dA nucleotides, but is interrupted by a random sequence having an equal distribution of the four nucleotides (dA, dC, dG, dT). Such random sequence may be 5 to 50, preferably 10 to 30, more preferably 10 to 20 nucleotides in length. Such a cassette is disclosed in WO 2016/005004 A1. Any poly(A) cassette disclosed in WO 2016/005004 A1 may be used in the present invention. A poly(A) cassette that essentially consists of dA nucleotides, but is interrupted by a random sequence having an equal distribution of the four nucleotides (dA, dC, dG, dT) and having a length of e.g. 5 to 50 nucleotides shows, on DNA level, constant propagation of plasmid DNA in E. coli and is still associated, on RNA level, with the beneficial properties with respect to supporting RNA stability and translational efficiency.

Consequently, in a preferred embodiment of the present invention, the 3' poly(A) sequence contained in an RNA molecule described herein essentially consists of A nucleotides, but is interrupted by a random sequence having an equal distribution of the four nucleotides (A, C, G, U). Such random sequence may be 5 to 50, preferably 10 to 30, more preferably 10 to 20 nucleotides in length.

Codon Usage

In general, the degeneracy of the genetic code will allow the substitution of certain codons (base triplets) that are present in an RNA sequence by other codons (base triplets), while maintaining the same coding capacity. In some embodiments of the present invention, at least one codon of an open reading frame comprised by a RNA molecule differs from the respective codon in the respective open reading frame in the species from which the open reading frame originates. In that embodiment, the coding sequence of the open reading frame is said to be "adapted".

For example, when the coding sequence of an open reading frame is adapted, frequently used codons may be selected: WO 2009/024567 A1 describes the adaptation of a coding sequence of a nucleic acid molecule, involving the substitution of rare codons by more frequently used codons. Since the frequency of codon usage depends on the host cell or host organism, that type of adaptation is suitable to fit a nucleic acid sequence to expression in a particular host cell or host organism. Generally speaking, more frequently used codons are typically translated more efficiently in a host cell or host organism, although adaptation of all codons of an open reading frame is not always required.

For example, when the coding sequence of an open reading frame is adapted, the content of G (guanylate) residues and C (cytidylate) residues may be altered by selecting codons with the highest GC-rich content for each amino acid. RNA molecules with GC-rich open reading frames were reported to have the potential to reduce immune activation and to improve translation and half-life of RNA (Thess et al., 2015, Mol. Ther. 23, 1457-1465).

The open reading frame encoding the replicase according to the present invention may be adapted respectively.

Characterization of the Replicon

The system of the present invention comprises a replicon. A nucleic acid construct that is capable of being replicated by a replicase, preferably an alphaviral replicase, is termed replicon. Typically, the replicon according to the present invention is an RNA molecule.

According to the invention, the term "replicon" defines a RNA molecule that can be replicated by RNA-dependent RNA polymerase, yielding—without DNA intermediate—one or multiple identical or essentially identical copies of the RNA replicon. "Without DNA intermediate" means that no deoxyribonucleic acid (DNA) copy or complement of the replicon is formed in the process of forming the copies of the RNA replicon, and/or that no deoxyribonucleic acid (DNA) molecule is used as a template in the process of forming the copies of the RNA replicon, or complement thereof.

According to the invention, the term "can be replicated" generally describes that one or more identical or essentially identical copies of a nucleic acid can be prepared. When used together with the term "replicase", such as in "can be replicated by a replicase", the term "can be replicated" describes functional characteristics of the replicon with respect to a replicase. These functional characteristics comprise at least one of (i) the replicase is capable of recognizing the replicon and (ii) the replicase is capable of acting as RNA-dependent RNA polymerase (RdRP). Preferably, the replicase is capable of both (i) recognizing the replicon and (ii) acting as RNA-dependent RNA polymerase. The RNA-dependent RNA polymerase may use the replicon, complement thereof or a part of any thereof as template.

The expression "capable of recognizing" describes that the replicase is capable of physically associating with the replicon, and preferably, that the replicase is capable of binding to the replicon, typically non-covalently. The term "binding" can mean that the replicase has the capacity of binding to any one or more of a conserved sequence element 1 (CSE 1) or complementary sequence thereof (if comprised by the replicon), conserved sequence element 2 (CSE 2) or complementary sequence thereof (if comprised by the replicon), conserved sequence element 3 (CSE 3) or complementary sequence thereof (if comprised by the replicon), conserved sequence element 4 (CSE 4) or complementary sequence thereof (if comprised by the replicon). Preferably, the replicase is capable of binding to CSE 2 [i.e. to the (+) strand] and/or to CSE 4 [i.e. to the (+) strand], or of binding to the complement of CSE 1 [i.e. to the (−) strand] and/or to the complement of CSE 3 [i.e. to the (−) strand].

The expression "capable of acting as RdRP" includes the meaning that the replicase is capable to catalyze the synthesis of the (−) strand complement of alphaviral genomic (+) strand RNA, wherein the (+) strand RNA has template function, and/or that the replicase is capable to catalyze the synthesis of (+) strand alphaviral genomic RNA, wherein the (−) strand RNA has template function. In general, the expression "capable of acting as RdRP" can also include that the replicase is capable to catalyze the synthesis of a (+) strand subgenomic transcript wherein a (−) strand RNA has template function, and wherein synthesis of the (+) strand subgenomic transcript is typically initiated at an alphavirus subgenomic promoter.

The expressions "capable of binding" and "capable of acting as a RdRP" refer to the capability at normal physiological conditions. In particular, the expressions refer to the conditions inside a cell, which expresses alphavirus replicase or which has been transfected with a nucleic acid that codes for alphavirus replicase. The cell is preferably a eukaryotic cell. The capability of binding and/or the capability of acting as RdRP can be experimentally tested, e.g. in a cell-free in vitro system or in a eukaryotic cell. Optionally, said eukaryotic cell is a cell from a species to which the particular alphavirus that represents the origin of the replicase is infectious. For example, when the alphavirus replicase from a particular alphavirus is used that is infectious to humans, the normal physiological conditions are conditions in a human cell. More preferably, the eukaryotic cell (in one example human cell) is from the same tissue or organ to which the particular alphavirus that represents the origin of the replicase is infectious.

In view of these functional characteristics, the replicon of the present invention and the replicase construct of the present invention form a functional pair. The alphavirus replicase can be any alphavirus replicase according to the invention, and the nucleotide sequence of the replicon RNA is not particularly limited, as long as the replicon can be replicated by the alphavirus replicase in trans.

When the system of the present invention is introduced into a cell, preferably a eukaryotic cell, the replicase encoded on the replicase construct can be translated, thereby generating a replicase enzyme. After translation, the replicase is capable of replicating the RNA replicon in trans. Thus, the present invention provides a system for replicating RNA in trans. Consequently, the system of the present invention is a trans-replication system. The replicon according to the present invention is thus a trans-replicon.

Herein, trans (e.g. in the context of trans-acting, trans-regulatory), in general, means "acting from a different molecule" (i.e., intermolecular). It is the opposite of cis (e.g. in the context of cis-acting, cis-regulatory), which, in general, means "acting from the same molecule" (i.e., intramolecular). In the context of RNA synthesis (including transcription and RNA replication), a trans-acting element includes a nucleic acid sequence that contains a gene encoding an enzyme capable of RNA synthesis (replicase). The replicase functions in the synthesis of a second nucleic acid molecule, i.e. a different molecule. Both the trans-acting RNA and the protein that it encodes are said to "act in trans" on the target gene. In the context of the present invention, the trans-acting RNA encodes an alphaviral RNA polymerase. The alphaviral RNA polymerase is capable of replicating RNA and is therefore termed replicase. The replicase acts in trans on a second RNA molecule (the replicon). The replicon that can be replicated by the replicase in trans according to the present invention is synonymously referred to herein as "trans-replicon" or as "replicon according to the present invention".

The fact that alphaviral replicase is generally able to recognize and replicate a template RNA in trans was initially discovered in the 1980s, but the potential of trans-replication for biomedical applications was not recognized, inter alia because trans-replicated RNA was considered to inhibit efficient replication: it was discovered in the case of defective interfering (DI) RNA that co-replicates with alphaviral genomes in infected cells (Barrett et al., 1984, J. Gen. Virol., vol. 65 (Pt 8), pp. 1273-1283; Lehtovaara et al., 1981, Proc. Natl. Acad. Sci. U.S.A, vol. 78, pp. 5353-5357; Pettersson, 1981, Proc. Natl. Acad. Sci. U.S.A, vol. 78, pp. 115-119). DI RNAs are trans-replicons that may occur quasi-naturally during infections of cell lines with high virus load. DI elements co-replicate so efficiently that they reduce the virulence of the parental virus and thereby act as inhibitory parasitic RNA (Barrett et al., 1984, J. Gen. Virol., vol. 65 (Pt 11), pp. 1909-1920). Although the potential for biomedical applications was not recognized, the phenomenon of trans-replication was used in several basic studies aiming to elucidate mechanisms of replication, without requiring to express the replicase from the same molecule in cis; further, the separation of replicase and replicon also allows functional studies involving mutants of viral proteins, even if respective mutants were loss-of-function mutants (Lemm et al., 1994, EMBO J., vol. 13, pp. 2925-2934). These loss-of function studies and DI RNA did not suggest that trans-activation systems based on alphaviral elements may eventually become available to suit therapeutic purposes. A more recent approach for in vivo delivery of RNA to a vertebrate suggests a cis-replication system comprising a self-replicating RNA molecule (WO 2012/006376 A2).

Contrary to suggestions in the prior art, the trans-replication system of the present invention is very suitable for gene expression: it is associated with high expression levels, high antigen titer, and a satisfying degree of survival of vaccinated animals can be achieved even when the level of antigen-encoding RNA is relatively low. In particular, administration of 1 μg trans-replicon-RNA of the system of the present invention can cause virus neutralization titer and HA titer comparable to administration of 5 μg cis-replicon (see Example 6 and FIG. 7). This represents a significant contribution to the art, particularly an advancement of the field of animal vaccination, since the overall amount of vaccine-encoding nucleic acid can be reduced. This saves costs and time for production and is important at least for the following reasons:

First and foremost, the versatility of the system of the present invention—comprising two separate RNA molecules—allows that replicon and replicase construct can be designed and/or prepared at different times and/or at different sites. In one embodiment, the replicase construct is prepared at a first point in time, and the replicon is prepared at a later point in time. For example, following its preparation, the replicase construct may be stored for use at a later point in time. The present invention provides increased flexibility compared to cis-replicons: when a new pathogen emerges, the system of the present invention may be designed for vaccination, by cloning into the replicon a nucleic acid encoding a polypeptide that elicits an immune response against the new pathogen. A previously prepared replicase construct may be recovered from storage. Thus, it is not required that, at the time the replicase construct is designed and prepared, the nature of a particular pathogen, or of the antigen(s) of a particular pathogen, is known. Consequently, it is not required that, at the time the replicase construct is designed and prepared, a replicon encoding a polypeptide that elicits an immune response against a particular new pathogen is available. In other words, the replicase construct can be designed and prepared independently of any particular replicon. This allows to rapidly react to the emergence of new pathogens, or to pathogens characterized by expression of at least one new antigen, because preparation of the replicon devoid of replicase requires less effort and resources than the preparation of cis-replicons. History tells that a system allowing for rapid reaction to pathogens is needed: this is illustrated e.g. by the occurrence of pathogens causing severe acute respiratory syndrome (SARS), Ebola and various influenza virus subtypes in recent years.

Second, in the case of animal vaccination, the cost of a vaccine is key to its success in the veterinary and farming community. Since the replicon of the present invention can be replicated in the presence of functional alphavirus non-structural protein, e.g. in a cell of a vaccinated animal, high levels of expression of a gene of interest may be achieved even if relatively low amounts replicon RNA are administered. The low amounts of replicon RNA positively influence the costs of vaccine per subject.

Third, the trans-replicon according to the present invention is typically a shorter nucleic acid molecule than a typical cis-replicon. This enables faster cloning of a replicon encoding a protein of interest, e.g. an immunogenic polypeptide, and provides higher yields of the protein of interest (see e.g. Example 1).

In a preferred embodiment, the replicon can be replicated by an alphavirus replicase from Semliki Forest virus, including a naturally occurring Semliki Forest virus and a variant or derivative of Semliki Forest virus, such as an attenuated Semliki Forest virus. In an alternative preferred embodiment, the replicon can be replicated by an alphavirus replicase from Sindbis virus, including a naturally occurring Sindbis virus and a variant or derivative of Sindbis virus, such as an attenuated Sindbis virus. In an alternative preferred embodiment, the replicon can be replicated by an alphavirus replicase from Venezuelan equine encephalitis virus (VEEV), including a naturally occurring VEEV and a variant or derivative of VEEV, such as an attenuated VEEV.

The RNA replicon according to the present invention is preferably a single stranded RNA molecule. In general, single-stranded coding nucleic acid molecules comprise twice as much genetic information per weight unit (e.g. µg) of nucleic acid material. Thus, the single-stranded nature represents a further advantage compared to the double-stranded prior art DNA vectors employed e.g. by Spuul et al., supra. The replicon according to the present invention is typically a (+) stranded RNA molecule.

In one embodiment, the RNA replicon is an isolated nucleic acid molecule.

The trans-replication system of the present invention is suitable for inoculation of a host cell, and for expression of a gene of interest in a host cell (see e.g. Examples 1-3). In some experimental examples of the present invention, the trans-replicon RNA comprises as gene of interest a gene encoding a reporter protein (e.g. fluorescent protein, such as GFP or eGFP), which allows to readily determine efficiency of expression of the respective gene of interest. As shown in Example 2, the trans-replication system—comprising two RNAs—is associated with significantly better efficiency of expression of a gene of interest, compared to cis-replication (eGFP replicon RNA).

The trans-replication system of the present invention is suitable for efficient expression of a gene of interest in a human or animal, e.g. for expression at high levels. In particular, Example 5 demonstrates that a reporter protein can be efficiently produced, and Example 6 demonstrates that a therapeutic effect, protection from pathogenic infection, can be achieved in animals treated by the system of the present invention.

Without wishing to be bound by any particular theory, it is conceivable that the e.g. about 7400 nucleotides that encode the replicase in typical alphaviruses found in nature impose a burden on a cell, since amplification of the full-length replicon would be required. It is conceivable that a major part of this burden is eliminated when a non-replicative replicase construct, e.g. in the form of mRNA, is used for replicase expression. This allows to use a trans-replicon for RNA amplification and transgene expression. If the replicase construct is not replicated in the cell (i.e. the only foreign construct that is replicated is the trans-replicon of the present invention), waste of cellular energy and resources (nucleotides etc.) is avoided, which might explain superior expression levels. Furthermore, shorter replicon RNA likely requires less time for RNA synthesis. It is therefore conceivable that the saving of time, cellular energy and/or resources contributes to replication at higher levels.

Conserved Sequence Elements

In one embodiment, the replicon is or comprises alphaviral genomic RNA or is derived from alphaviral genomic RNA. In one embodiment, the replicon according to the present invention comprises one or more of the conserved sequence elements (CSEs) (Strauss & Strauss, Microbiol. Rev., 1994, vol. 58, pp. 491-562). In particular, the replicon may comprise one or more of the conserved sequence elements (CSEs) of an alphavirus found in nature or of a variant or derivative thereof:

CSE 1, believed to function as a promoter for (+) strand synthesis from (−) strand templates. If present, the CSE 1 is typically located at or near the 5' end of the replicon RNA.

CSE 2, believed to act as a promoter or enhancer for (−) strand synthesis from a genomic (+) strand RNA template. If present, CSE 2 is typically located downstream of CSE 1, but upstream of CSE 3.

CSE 3, believed to contribute to efficient transcription of the subgenomic RNA; If present, the CSE 3 is typically located upstream of the coding sequence for the gene of interest (if any), but downstream of CSE 2.

CSE 4, believed to function as a core promoter for initiation of (−) strand synthesis. If present, the CSE 4 is typically located downstream of the coding sequence for the gene of interest (if any). At any rate, CSE 4 is typically present downstream of CSE 3. Details of the sequence of CSE 4 (also termed 3' CSE) in various alphaviruses have been described by Hardy & Rice, J. Virol., 2005, vol. 79, pp. 4630-4639, and in the present invention, the sequence of a CSE 4 may for example be selected according to the teaching of that document.

In one embodiment, the RNA replicon according to the present invention comprises:
(1) an alphavirus 5' replication recognition sequence, and
(2) an alphavirus 3' replication recognition sequence In one embodiment, the alphavirus 5' replication recognition sequence comprises alphavirus CSE 1 and/or CSE 2. In a naturally occurring alphavirus, CSE 1 and/or CSE 2 are typically comprised in the 5' replication recognition sequence.

In one embodiment, the alphavirus 3' replication recognition sequence comprises alphavirus CSE 4. In a naturally occurring alphavirus, CSE 4 is typically comprised in the 3' replication recognition sequence.

In one embodiment, the alphavirus 5' replication recognition sequence and the alphavirus 3' replication recognition sequence are capable of directing replication of the RNA replicon according to the present invention in the presence of the replicase. Thus, when present alone or preferably together, these recognition sequences direct replication of the RNA replicon in the presence of the replicase. Without wishing to be bound by any particular theory, it is understood that alphavirus conserved sequence elements (CSEs) 1, 2 and 4 are (comprised in) recognition sequences that direct replication of the RNA replicon in the presence of the replicase. Thus, in this embodiment, the replicon will typically comprise CSEs 1, 2 and 4.

It is preferable that the replicase that is encoded by the replicase construct is an alphavirus replicase that is capable of recognizing both the alphavirus 5' replication recognition sequence and the alphavirus 3' replication recognition sequence of the replicon.

In one embodiment, this is achieved when the alphavirus 5' replication recognition sequence and the alphavirus 3' replication recognition sequence are native to the alphavirus from which the replicase is derived. Native means that the natural origin of these sequences is the same alphavirus. In one embodiment, CSE 1, CSE 2 and CSE 4 are native to the alphavirus from which the replicase is derived.

In an alternative embodiment, the 5' replication recognition sequence (and/or CSE 1 and/or CSE 2) and/or the alphavirus 3' replication recognition sequence (and/or CSE 4) are not native to the alphavirus from which the replicase is derived, provided that the alphavirus replicase is capable of recognizing both the 5' replication recognition sequence (and/or CSE 1 and/or CSE 2) and the 3' replication recognition sequence (and/or CSE 4) of the replicon. In other words, the replicase is compatible to the 5' replication recognition sequence (and/or CSE 1 and/or CSE 2) and the 3' replication recognition sequence (and/or CSE 4). When a non-native alphavirus replicase is capable of recognizing a respective sequence or sequence element, the replicase is said to be compatible (cross-virus compatibility). Examples of cross-virus compatibility concerning (375') replication recognition sequences and CSEs, respectively, with non-native replicases from different alphaviruses are known in the art (reviewed e.g. by Strauss & Strauss, Microbiol. Rev., 1994, vol. 58, pp. 491-562).

Any combination of (3'/5') replication recognition sequences and CSEs, respectively, with alphavirus replicase is possible as long as cross-virus compatibility exists. Cross-virus compatibility can readily be tested by the skilled person working the present invention by incubating a replicase to be tested together with an RNA, wherein the RNA has 3'- and 5' replication recognition sequences to be tested, at conditions suitable for RNA replication, e.g. in a suitable host cell. If replication occurs, the (3'/5') replication recognition sequences and the replicase are determined to be compatible.

Subgenomic Promoter

In particular embodiments, the RNA replicon according to the present invention comprises an expression control sequence. A typical expression control sequence is or comprises a promoter. In one embodiment, the RNA replicon according to the present invention comprises a subgenomic promoter. Preferably, the subgenomic promoter is an alphavirus subgenomic promoter. The nucleotide sequence of the subgenomic promoter is highly conserved among alphaviruses (Strauss & Strauss, Microbial. Rev., 1994, vol. 58, pp. 491-562).

Preferably, the subgenomic promoter is a promoter for a structural protein of an alphavirus. This means that the subgenomic promoter is one which is native to an alphavirus and which controls transcription of the gene of one or more structural proteins in said alphavirus.

It is preferable that the subgenomic promoter is compatible with the replicase of the replicase construct. Compatible in this context means that the alphavirus replicase is capable of recognizing the subgenomic promoter. Thus, it is preferable that the replicase that is encoded by the replicase construct is an alphavirus replicase that is capable of recognizing the subgenomic promoter of the replicon.

In one embodiment, this is achieved when the subgenomic promoter is native to the alphavirus from which the replicase is derived. Native means that the natural origin of the subgenomic promoter and of the replicase is the same alphavirus.

In an alternative embodiment, the subgenomic promoter is not native to the alphavirus from which the replicase is derived, provided that the alphavirus replicase is capable of recognizing the subgenomic promoter of the replicon. In other words, the replicase is compatible with the subgenomic promoter (cross-virus compatibility). Any combination of subgenomic promoter and replicase is possible as long as cross-virus compatibility exists. Cross-virus compatibility can readily be tested by the skilled person working the present invention by incubating a replicase to be tested together with an RNA, wherein the RNA has a subgenomic promoter to be tested, at conditions suitable for RNA synthesis from the subgenomic promoter. If a subgenomic transcript is prepared, the subgenomic promoter and the replicase are determined to be compatible. Various examples of cross-virus compatibility are known: in some cases, a non-native subgenomic promoter even leads to more efficient transcription than the native subgenomic promoter (reviewed by Strauss & Strauss, Microbiol. Rev., 1994, vol. 58, pp. 491-562).

Preferably, the replicon according to the present invention comprises a conserved sequence element 3 (CSE 3) from an alphavirus. CSE 3 is believed to contribute to efficient transcription of subgenomic RNA. It is known that transcription of the subgenomic RNA occurs very efficiently when CSE 3 is present. Typically, the CSE 3 is a polynucleotide stretch of about 24 nucleotides. In alphavirus genomes, CSE 3 is located in the junction region between the coding sequence for the non-structural and structural proteins. In the trans-replicon of the present invention, the CSE 3 is typically present upstream (5') of an open reading frame (ORF) under control of the subgenomic promoter. In case the replicon according to the present invention contains one ORF under control of the subgenomic promoter, CSE 3 is located 5' of that one ORF. In case the replicon according to the present invention contains more than one ORF under control of a subgenomic promoter, a CSE 3 may be located 5' of each such ORF. In one embodiment, the CSE 3 is native to the alphavirus from which the replicase is derived. In an alternative embodiment, the CSE 3 is not native to the alphavirus from which the replicase is derived, provided that the alphavirus replicase is capable of recognizing the CSE 3 of the replicon.

Optional Further Features of the Replicon

In one embodiment, the RNA replicon according to the present invention comprises a 3' poly(A) sequence. The poly(A) sequence of alphavirus RNA has been described to play a role in the efficiency of translation of viral non-structural proteins and RNA stability, analogous to its role in cellular mRNA (Hardy & Rice, J. Virol., 2005, vol. 79, pp. 4630-4639). In the present invention, a poly(A) sequence is envisaged to play a role in in the efficiency of translation of a gene of interest and in replicon stability. Embodiments and preferred embodiments of the 3' poly(A) sequence of the replicon according to the present invention can be selected among the ones disclosed herein for the 3' poly(A) sequence of the replicase construct. In addition to that, in one embodiment, the poly(A) sequence (if present on the replicon according to the present invention) is preceded by an alphavirus conserved sequence element 4 (CSE 4). Preferably, it is directly adjacent to the CSE 4, so that the most 3' nucleotide of the CSE 4 is directly adjacent to the most 5' A nucleotide of the poly(A) tail.

Figure 1:
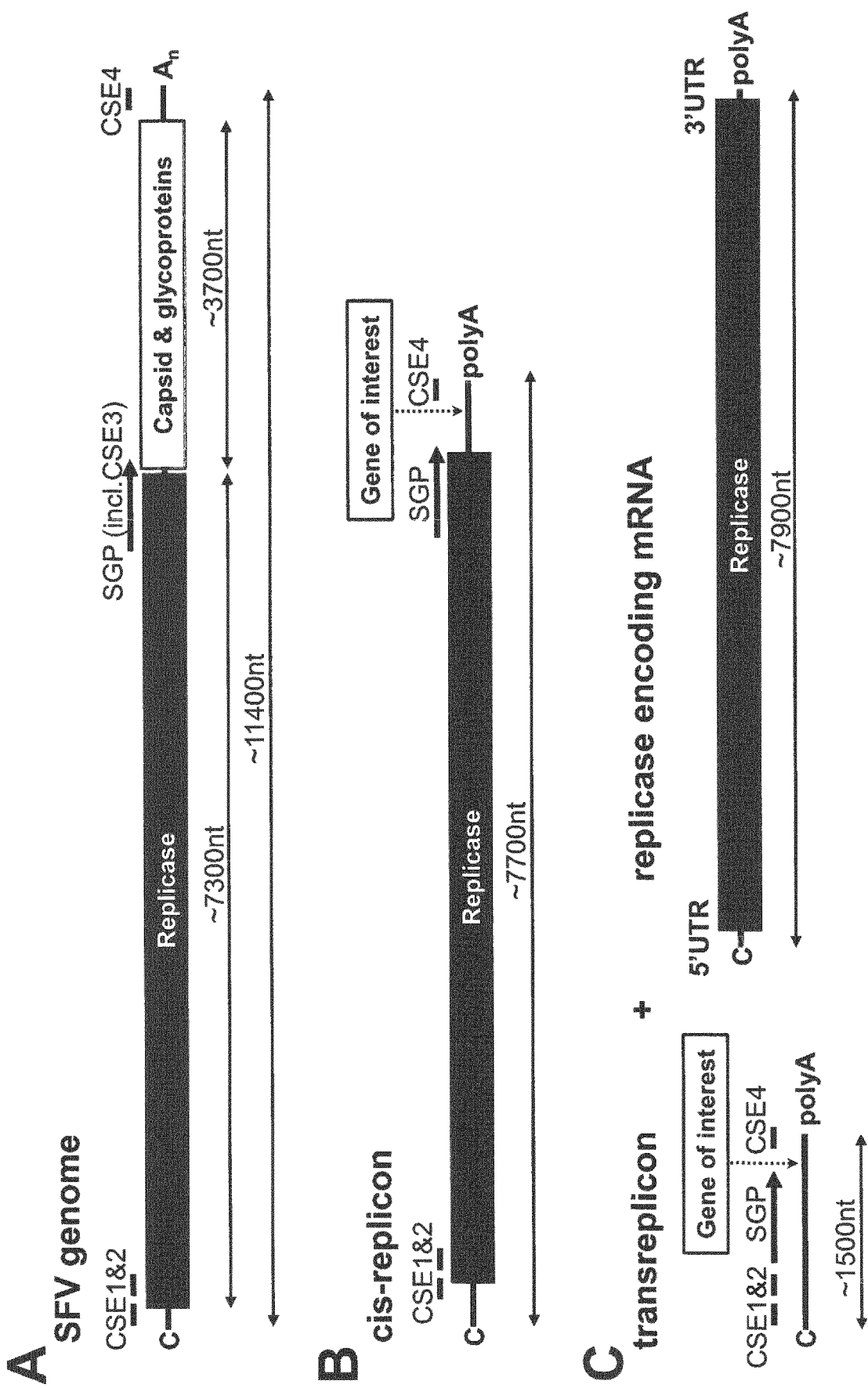
FIG. 1: Alphavirus genome organization and engineered nucleic acid constructs comprising elements derived from an alphavirus genome.

In one embodiment, the RNA replicon according to the present invention comprises a 5'-cap (including a cap analog). For illustration, in FIG. 1, the cap (or cap analog) is symbolized by the letter C. Aspects of the cap (or analog) of the replicon according to the present invention are identical to the aspects described herein for the cap (or analog) of the replicase construct, except that the presence of a cap is not compulsory for the case of the RNA replicon. Thus, in an alternative embodiment, the RNA replicon according to the present invention does not comprise a cap. In that embodiment, it may comprise a free 5' OH terminus, or any suitable 5' modification. That embodiment is equally comprised by the present invention irrespective of the fact that FIG. 1 schematically depicts an alternative embodiment in which the RNA replicon comprises a cap, illustrated by the letter C.

In one embodiment, the coding sequence of the open reading frame(s) present on the replicon according to the present invention (if any) is adapted. Embodiments and preferred embodiments of codon adaptation of the replicon according to the present invention can be selected among the ones disclosed herein for the case of codon adaptation of the replicase construct. The codons of the open reading frame(s) can be adapted for expression in a host cell or host organism.

Heterologous Nucleic Acid Sequence

In one embodiment the replicon additionally comprises at least one nucleic acid sequence that does not originate from a virus, in particular not from an alphavirus. In preferred embodiments, the RNA replicon according to the present invention comprises a heterologous nucleic acid sequence. According to the present invention, the term "heterologous" refers to the situation that a nucleic acid sequence is not naturally functionally linked to an alphavirus nucleic acid sequence, such as an alphavirus expression control sequence, particularly an alphavirus subgenomic promoter. The heterologous nucleic acid sequence is comprised by the nucleic acid sequence of the replicon.

Preferably, the heterologous nucleic acid sequence is under control of a subgenomic promoter, preferably an alphavirus subgenomic promoter. More preferably, the heterologous nucleic acid sequence is localized downstream of the subgenomic promoter. The alphavirus subgenomic promoter is very efficient, and is therefore suitable for heterologous gene expression at high levels (Jose et al., Future Microbiol., 2009, vol. 4, pp. 837-856). Preferably, the subgenomic promoter controls production of subgenomic RNA comprising a transcript of the heterologous nucleic acid sequence or part thereof.

Preferably, the subgenomic promoter is a promoter for a structural protein of an alphavirus. This means that the subgenomic promoter is one which is native to an alphavirus and which controls transcription of the coding sequence of one or more structural proteins in said alphavirus. According to the present invention, the heterologous nucleic acid sequence may partially or completely replace a viral nucleic acid sequence, such as a nucleic acid sequence encoding alphavirus structural proteins. Preferably, the heterologous nucleic acid sequence is not derived from an alphavirus; in particular, it is preferred that the heterologous nucleic acid sequence is not derived from the same alphavirus as the alphavirus from which the subgenomic promoter is derived. In one embodiment, the replicon comprises a CSE 3, and the heterologous nucleic acid sequence is heterologous to the CSE 3.

Protein of Interest

In one embodiment, the RNA replicon according to the present invention comprises an open reading frame encoding a peptide of interest or protein of interest. Preferably, the protein of interest is encoded by heterologous nucleic acid. Preferably, the gene encoding the protein of interest (i.e. the gene of interest) is present together with an expression control sequence. Preferably, the gene of interest is under control of a promoter, preferably under control of the subgenomic promoter as described herein. More preferably the gene of interest is located downstream of a subgenomic promoter.

The gene encoding the protein of interest is synonymously termed "gene of interest" or "transgene". The transgene is present on the replicon according to the present invention preferably under control of the subgenomic promoter, and its localization thus resembles the localization of the structural genes in an alphavirus. Preferably, the location downstream of the subgenomic promoter is such that a subgenomic transcript will comprise a transcript of the gene of interest. Preferably, the gene of interest comprises an open reading frame comprising a start codon (base triplet), typically AUG (in the RNA molecule) or ATG (in a respective DNA molecule).

Preferably, in case the replicon RNA according to the present invention comprises at least one open reading frame (protein coding region), the replicon is an mRNA molecule.

The replicon according to the present invention may encode a single polypeptide or multiple polypeptides. Multiple polypeptides can be encoded as a single polypeptide (fusion polypeptide) or as separate polypeptides. If polypeptides are encoded as separate polypeptides, then one or more of these may be provided with an upstream IRES or an additional viral promoter element. Alternatively, the replicon according to the present invention may comprise more than one open reading frame, each of which under the control of a subgenomic promoter. When such a multiple-ORF replicon is placed in eukaryotic cells, multiple subgenomic transcripts will be prepared, each initiated by its own subgenomic promoter (Strauss & Strauss, Microbiol. Rev., 1994, vol. 58, pp. 491-562). Alternatively, a poly-protein or fusion polypeptide comprises individual polypeptides separated by a autocatalytic protease (e.g. foot-and-mouth disease virus 2A protein), or an intein.

Preferably, the open reading frame encoding a protein of interest is non-native to the alphavirus from which the replicase is derived. Preferably, the open reading frame under control of the subgenomic promoter does not encode any alphaviral protein. In preferred embodiments, the open reading frame under control of the subgenomic promoter does not encode any full-length alphavirus non-structural protein (nsP) or fragment thereof, and/or does not encode any full-length alphavirus structural protein (sP) or fragment thereof. Preferably, the open reading frame encoding a protein of interest under control of the subgenomic promoter does not encode any alphavirus structural protein. In one embodiment, the system of the present invention does not comprise a nucleic acid sequence encoding one or more alphavirus structural proteins. In one embodiment, the system does not comprise a nucleic acid sequence encoding any core nucleocapsid protein C, envelope protein P62 and/or envelope protein E1.

It is an advantage of the system of the present invention that it does not require the presence or administration of helper virus encoding alphavirus structural proteins. This is advantage compared to the prior art (e.g. Bredenbeek et al., J. Virol, 1993, vol. 67, pp. 6439-6446), which describes a trans-replication system capable of packaging replicon vectors that lack the structural protein ORF into viral particles, wherein the structural proteins must be expressed in trans from helper RNA. The replication of these helper RNAs, encoding alphavirus structural proteins, typically depends on replicase expressed from the replicon RNA that encodes the antigen. Helper RNA itself lacks functional replicase and contains only the conserved RNA sequence elements required for replication (Smerdou & Liljeström, 1999, J. Virol., vol. 73, pp. 1092-1098; Ehrengruber & Lundstrom, 1999, Proc. Natl. Acad. Sci. U. S. A, vol. 96, pp. 7041-7046). However, no such helper RNA encoding alphavirus structural proteins is required for achieving the success of the present invention. Thus, preferably, no nucleic acid molecule of the present invention encodes alphavirus structural proteins.

In one embodiment, the open reading frame encodes a reporter protein. In that embodiment, the open reading frame comprises a reporter gene. Certain genes may be chosen as reporters because the characteristics they confer on cells or organisms expressing them may be readily identified and measured, or because they are selectable markers. Reporter genes are often used as an indication of whether a certain gene has been taken up by or expressed in the cell or organism population. Preferably, the expression product of the reporter gene is visually detectable. Common visually detectable reporter proteins typically possess fluorescent or luminescent proteins. Examples of specific reporter genes include the gene that encodes jellyfish green fluorescent protein (GFP), which causes cells that express it to glow green under blue light, the enzyme luciferase, which catalyzes a reaction with luciferin to produce light, and the red fluorescent protein (RFP). Variants of any of these specific reporter genes are possible, as long as the variants possess visually detectable properties. For example, eGFP is a point mutant variant of GFP. The reporter protein embodiment is particularly suitable for testing expression mediated by the trans-replication system of the present invention in vitro and in vivo, see e.g. Examples 2 and 4. For example, in both cases (cis-replication system and trans-replication system, respectively), presence of the reporter protein presupposes that a subgenomic transcript comprising the nucleic acid sequence encoding the reporter protein is prepared. In turn, production of the subgenomic transcript in a cell presupposes that the replicase construct is present in that cell, and that the replicase gene is expressed.

In an alternative embodiment, the open reading frame does not encode a reporter protein. For example, when the system of the present invention is designed for introduction of a pharmaceutically active peptide or protein into a human or animal subject, as shown e.g. in Example 6, it is possible that no fluorescent reporter protein is encoded. For example, a pharmaceutically active protein may be the only protein encoded by the open reading frame under control of the subgenomic promoter.

According to the invention, in one embodiment, RNA of the replicon comprises or consists of pharmaceutically active RNA. A "pharmaceutically active RNA" may be RNA that encodes a pharmaceutically active peptide or protein. Preferably, the RNA replicon according to the present invention encodes a pharmaceutically active peptide or protein. Preferably, the open reading frame encodes a pharmaceutically active peptide or protein. Preferably, the RNA replicon comprises an open reading frame that encodes a pharmaceutically active peptide or protein, preferably under control of the subgenomic promoter.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., the peptide or protein elicits an immune response in a subject which may be therapeutic or partially or fully protective. A pharmaceutically active peptide or protein can also be referred to as therapeutic peptide or protein.

In one embodiment, the pharmaceutically active peptide or protein is or comprises an immunologically active compound or an antigen or an epitope.

According to the invention, the term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. In one embodiment, the immune response involves stimulation of an antibody response (usually including immunoglobulin G (IgG)). Immunologically active compounds possess potent immunostimulating activity including, but not limited to, antiviral and antitumor activity, and can also down-regulate other aspects of the immune response, for example shifting the immune response away from a $TH_2$ immune response, which is useful for treating a wide range of $TH_2$ mediated diseases.

According to the invention, the term "antigen" or "immunogen" covers any substance that will elicit an immune response. In particular, an "antigen" relates to any substance that reacts specifically with antibodies or T-lymphocytes (T-cells). According to the present invention, the term "antigen" comprises any molecule which comprises at least one epitope. Preferably, an antigen in the context of the present invention is a molecule which, optionally after processing, induces an immune reaction, which is preferably specific for the antigen. According to the present invention, any suitable antigen may be used, which is a candidate for an immune reaction, wherein the immune reaction may be both a humoral as well as a cellular immune reaction. In the context of the embodiments of the present invention, the antigen is preferably presented by a cell, preferably by an antigen presenting cell, in the context of MHC molecules, which results in an immune reaction against the antigen. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof. In preferred embodiments, the antigen is a surface polypeptide, i.e. a polypeptide naturally displayed on the surface of a cell, a pathogen, a bacterium, a virus, a fungus, a parasite, an allergen, or a tumor. The antigen may elicit an immune response against a cell, a pathogen, a bacterium, a virus, a fungus, a parasite, an allergen, or a tumor.

The term "pathogen" refers to pathogenic biological material capable of causing disease in an organism, preferably a vertebrate organism. Pathogens include microorganisms such as bacteria, unicellular eukaryotic organisms (protozoa), fungi, as well as viruses.

The terms "epitope", "antigen peptide", "antigen epitope", "immunogenic peptide" and "MHC binding peptide" are used interchangeably herein and refer to an antigenic determinant in a molecule such as an antigen, i.e., to a part in or fragment of an immunologically active compound that is recognized by the immune system, for example, that is recognized by a T cell, in particular when presented in the context of MHC molecules. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. According to the invention an epitope may bind to MHC molecules such as MHC molecules on the surface of a cell and thus, may be a "MHC binding peptide" or "antigen peptide". The term "major histocompatibility complex" and the abbreviation "MHC" include MHC class I and MHC class II molecules and relate to a complex of genes which is present in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self-antigens (peptide fragments from the cell itself) and non-self-antigens (e.g., fragments of invading microorganisms) to a T cell. Preferred such immunogenic portions bind to an MHC class I or class II molecule. As used herein, an immunogenic portion is said to "bind to" an MHC class I or class II molecule if such binding is detectable using any assay known in the art. The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective.

In one embodiment, the protein of interest according to the present invention comprises an epitope suitable for vaccination of a target organism. A person skilled in the art will know that one of the principles of immunobiology and vaccination is based on the fact that an immunoprotective reaction to a disease is produced by immunizing an organism with an antigen, which is immunologically relevant with respect to the disease to be treated. According to the present invention, an antigen is selected from the group comprising a self-antigen and non-self-antigen. A non-self-antigen is preferably a bacterial antigen, a virus antigen, a fungus antigen, an allergen or a parasite antigen. It is preferred that the antigen comprises an epitope that is capable of eliciting an immune response in a target organism. For example, the epitope may elicit an immune response against a bacterium, a virus, a fungus, a parasite, an allergen, or a tumor.

In some embodiments the non self-antigen is a bacterial antigen. In some embodiments, the antigen elicits an immune response against a bacterium which infects animals, including birds, fish and mammals, including domesticated animals. Preferably, the bacterium against which the immune response is elicited is a pathogenic bacterium.

In some embodiments the non-self-antigen is a virus antigen. A virus antigen may for example be a peptide from a virus surface protein, e.g. a capsid polypeptide or a spike polypeptide. In some embodiments, the antigen elicits an immune response against a virus which infects animals, including birds, fish and mammals, including domesticated animals. Preferably, the virus against which the immune response is elicited is a pathogenic virus.

In some embodiments the non-self-antigen is a polypeptide or a protein from a fungus. In some embodiments, the antigen elicits an immune response against a fungus which infects animals, including birds, fish and mammals, including domesticated animals. Preferably, the fungus against which the immune response is elicited is a pathogenic fungus.

In some embodiments the non-self-antigen is a polypeptide or protein from a unicellular eukaryotic parasite. In some embodiments, the antigen elicits an immune response against a unicellular eukaryotic parasite, preferably a pathogenic unicellular eukaryotic parasite. Pathogenic unicellular eukaryotic parasites may be e.g. from the genus *Plasmodium*, e.g. *P. falciparum, P. vivax, P. malariae* or *P. ovale*, from the genus *Leishmania*, or from the genus *Trypanosoma*, e.g. *T. cruzi* or *T. brucei*.

In some embodiments the non-self-antigen is an allergenic polypeptide or an allergenic protein. An allergenic protein or allergenic polypeptide is suitable for allergen immunotherapy, also known as hypo-sensitization.

In some embodiments the antigen is a self-antigen, particularly a tumor antigen. Tumor antigens and their determination are known to the skilled person.

In the context of the present invention, the term "tumor antigen" or "tumor-associated antigen" relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor antigen is identical between the tumor antigen which is expressed in normal tissues and the tumor antigen which is expressed in cancer tissues.

Examples for tumor antigens that may be useful in the present invention are p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT. Particularly preferred tumor antigens include CLAUDIN-18.2 (CLDN18.2) and CLAUDIN-6 (CLDN6).

In some embodiments, it is not required that the pharmaceutically active peptide or protein is an antigen that elicits an immune response. Suitable pharmaceutically active peptides or proteins may be selected from the group consisting of cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like. In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin, e.g. IL-2, IL-7, IL-12, IL-15, or IL-21.

Versatility of the System of the Present Invention

Advantages of the system of the present invention include the independence from nuclear transcription and the presence of key genetic information on two separate RNA molecules, which provides unprecedented design freedom. In view of its versatile elements, which are combinable with each other, the present invention allows to optimize replicase expression for a desired level of RNA amplification, for a desired target organism, for a desired level of production of a protein of interest, etc. The replicon that can be replicated by the replicase in trans can be designed independently.

For example, the following elements may be individually chosen, designed and/or adapted, based on the disclosure herein: capping of the replicase construct (particularly choice of a specific cap); 5'-UTR of the replicase construct; coding sequence of the ORF encoding replicase (codon-optimization); 3'-UTR of the replicase construct; poly(A) tail of the replicase construct; 5'-UTR of the replicon (as long as the replicon comprises a 5' replication recognition sequence for alphaviral replicase); subgenomic promoter sequence; 5'-UTR of the subgenomic transcript generated from the replicon; coding sequence of the ORF encoding a gene of interest (codon-optimization); 3'-UTR of the replicon and/or of the subgenomic transcript generated from the replicon (as long as the replicon comprises a 3' replication recognition sequence for alphaviral replicase); poly(A) tail of the replicon and/or of the subgenomic transcript generated from the replicon.

In addition to that, the present invention allows to co-transfect the optimal amounts of replicon and replicase construct for any given cell type—resting or cycling, in vitro or in vivo.

Safety Features of Embodiments of the Present Invention

The following features are preferred in the present invention, alone or in any suitable combination:

Preferably, the system of the present invention does not comprise any alphavirus structural protein, such as core nucleocapsid protein C, envelope protein P62, and/or envelope protein E1.

Preferably, the system of the present invention is not a particle-forming system. This means that, following inoculation of a host cell by the system of the present invention, the host cell does not produce virus particles, such as next generation virus particles. In one embodiment, the system is completely free of genetic information encoding any alphavirus structural protein, such as core nucleocapsid protein C, envelope protein P62, and/or envelope protein E1. This aspect of the present invention provides an added value in terms of safety over prior art systems wherein structural proteins are encoded on trans-replicating helper RNA (e.g. Bredenbeek et al., J. Virol, 1993, vol. 67, pp. 6439-6446).

Preferably, neither the replicon nor the replicase construct is capable of driving its own replication, i.e. cis-replication. In one embodiment, the replicon does not encode functional alphavirus replicase. In one embodiment, the replicase construct lacks at least one sequence element (preferably at least one CSE) that is required for (−) strand synthesis based on a (+) strand template, and/or for (+) strand synthesis based on a (−) strand template. In one embodiment, the replicase construct does not comprise CSE 1 and/or CSE 4.

Preferably, neither the replicon according to the present invention nor the replicase construct according to the present invention comprises an alphavirus packaging signal. For example, the alphavirus packaging signal comprised in the coding region of nsP2 of SFV (White et al. 1998, J. Virol., vol. 72, pp. 4320-4326) may be removed, e.g. by deletion or mutation. A suitable way of removing the alphavirus packaging signal includes adaptation of the codon usage of the coding region of nsP2. The degeneration of the genetic code may allow to delete the function of the packaging signal without affecting the amino acid sequence of the encoded nsP2.

In one embodiment, the system of the present invention is an isolated system. In that embodiment, the system is not present inside a cell, such as inside a mammalian cell, or is not present inside a virus capsid, such as inside a coat comprising alphavirus structural proteins. In one embodiment, the system of the present invention is present in vitro.

Inhibition of Interferon (IFN) Signaling

It has been reported that viability of cells in which RNA has been introduced for expression is reduced, in particular, if cells are transfected multiple times with RNA. As a solution, co-transfection with IFN inhibiting agents was found to enhance the viability of cells in which RNA is to be expressed by (WO 2014/071963 A1). Any inhibitor of intracellular IFN signaling or of extracellular IFN signaling as described in WO 2014/071963 A1 is suitable in the present invention. Preferably, the inhibitor is an inhibitor of IFN type I signaling.

In one embodiment of the present invention, the system of the present invention can be designed to enhance translation, particularly to inhibit negative influences on translation. This may include to inhibit intracellular interferon (IFN) signaling in the cells and to prevent engagement of IFN receptor by extracellular IFN. Preventing engagement of IFN receptor by extracellular IFN and inhibiting intracellular IFN signaling in the cells allows stable expression of RNA in the cells. Alternatively or additionally, preventing engagement of IFN receptor by extracellular IFN and inhibiting intracellular IFN signaling enhances survival of the cells, in particular, if cells are transfected repetitively with RNA. Without wishing to be bound by theory, it is envisaged that intracellular IFN signalling can result in inhibition of translation and/or RNA degradation. This can be addressed by inhibiting one or more IFN-inducible antivirally active effector proteins. The IFN-inducible antivirally active effector protein can be selected from the group consisting of RNA-dependent protein kinase (PKR), 2',5'-oligoadenylate synthetase (OAS) and RNaseL. Inhibiting intracellular IFN signalling may comprise inhibiting the PKR-dependent pathway and/or the OAS-dependent pathway. Inhibiting the PKR-dependent pathway may comprise inhibiting eIF2-alpha phosphorylation. Inhibiting PKR may comprise treating the cell with at least one PKR inhibitor. The PKR inhibitor may be a viral inhibitor of PKR. The preferred viral inhibitor of PKR is vaccinia virus E3. If a peptide or protein (e.g. E3, K3) is to inhibit intracellular IFN signaling, intracellular expression of the peptide or protein is preferred.

Vaccinia virus E3 is a 25 kDa dsRNA-binding protein (encoded by gene E3L) that binds and sequesters dsRNA to prevent the activation of PKR and OAS. E3 can bind directly to PKR and inhibits its activity, resulting in reduced phosphorylation of eIF2-alpha. Other suitable inhibitors of IFN signaling are Herpes simplex virus ICP34.5, Toscana virus NSs, *Bombyx mori* nucleopolyhedrovirus PK2, and HCV NS34A.

The inhibitor of intracellular IFN signaling may be provided to the cell in the form of a nucleic acid sequence (e.g. RNA) encoding the inhibitor of intracellular IFN signaling.

In one embodiment, the inhibitor of intracellular or extracellular IFN signaling is encoded by an mRNA molecule. That mRNA molecule may comprise a non-polypeptide-sequence modifying modification as described herein, e.g. cap, 5'-UTR, 3'-UTR, poly(A) sequence, adaptation of the codon usage.

In an alternative embodiment, the inhibitor of intracellular or extracellular IFN signaling is encoded by a replicon, preferably a trans-replicon. The replicon comprises nucleic acid sequence elements that allow replication by alphavirus replicase, typically CSE 1, CSE 2 and CSE 4; and preferably also nucleic acid sequence elements that allow production of a subgenomic transcript, i.e. a subgenomic promoter, typically comprising CSE 3. The replicon may additionally comprise one or more non-polypeptide-sequence modifying modifications as described herein, e.g. cap, poly(A) sequence, adaptation of the codon usage.

RNA Construct for Expressing Alphavirus Replicase

In a second aspect, the invention provides a RNA construct for expressing alphavirus replicase (replicase construct) comprising a 5'-cap for driving translation of the replicase. In the second aspect, it is possible that no alphavirus replicon according to the present invention is present. In other words, in the second aspect of the present invention, the replicase construct of the present invention, as described herein, may be provided independently from the replicon of the present invention. In the second aspect, the replicase construct can be independently characterized by any one or more of the features of the replicase construct of the first aspect of the present invention. In one embodiment, the RNA construct for expressing alphavirus replicase is an isolated nucleic acid molecule. This includes the embodiment that it is isolated, i.e. essentially free, from other nucleic acid molecules.

The RNA construct according to the second aspect is suitable for example for combination with a suitable replicon in the form of a system or kit.

DNA According to the Invention

In a third aspect, the invention provides a DNA comprising a nucleic acid sequence encoding the RNA construct for expressing alphavirus replicase (replicase construct) according to the first aspect of the invention, a RNA replicon according to the first aspect of the invention, or both.

In one embodiment, a DNA molecule according to the present invention encodes replicon and replicase construct of the system according to the first aspect of the invention. In an alternative embodiment, a first DNA molecule encodes one RNA element (replicon or replicase construct) of the system according to the first aspect of the invention, and a second DNA molecule encodes the respective other RNA element of the system according to the present invention.

Preferably, the DNA is double-stranded.

In a preferred embodiment, the DNA according to the third aspect of the invention is a plasmid. The term "plasmid", as used herein, generally relates to a construct of extrachromosomal genetic material, usually a circular DNA duplex, which can replicate independently of chromosomal DNA.

The DNA of the present invention may comprise a promoter that can be recognized by a DNA-dependent RNA-polymerase. This allows for transcription of the encoded RNA in vivo or in vitro, e.g. of the RNA of the present invention. IVT vectors may be used in a standardized manner as template for in vitro transcription. Examples of promoters preferred according to the invention are promoters for SP6, T3 or T7 polymerase.

In one embodiment, the DNA of the present invention is an isolated nucleic acid molecule.

Methods of Preparing RNA

Any RNA molecule according to the present invention, be it part of the system of the present invention or not, may be obtainable by in vitro transcription. In vitro-transcribed RNA (IVT-RNA) is of particular interest in the present invention. IVT-RNA is obtainable by transcription from a nucleic acid molecule (particularly a DNA molecule). The DNA molecule(s) of the third aspect of the present invention are suitable for such purposes, particularly if comprising a promoter that can be recognized by a DNA-dependent RNA-polymerase.

RNA according to the present invention can be synthesized in vitro. This allows to add cap-analogs to the in vitro transcription reaction. Typically, the poly(A) tail is encoded by a poly-(dT) sequence on the DNA template. Alternatively, capping and poly(A) tail addition can be achieved enzymatically after transcription.

The in vitro transcription methodology is known to the skilled person. For example, as mentioned in WO 2011/015347 A1, a variety of in vitro transcription kits is commercially available.

Kit

The present invention also provides a kit comprising a system according to the first aspect of the invention or an RNA construct for expressing alphavirus replicase according to the second aspect of the invention.

In one embodiment, the constituents of the kit are present as separate entities. For example, one nucleic acid molecule of the kit may be present in one entity, and the another nucleic acid of the kit may be present in a separate entity. For example, an open or closed container is a suitable entity. A closed container is preferred. The container used should preferably be RNAse-free or essentially RNAse-free.

In one embodiment, the kit of the present invention comprises RNA for inoculation with a cell and/or for administration to a human or animal subject.

The kit according to the present invention optionally comprises a label or other form of information element, e.g. an electronic data carrier. The label or information element preferably comprises instructions, e.g. printed written instructions or instructions in electronic form that are optionally printable. The instructions may refer to at least one suitable possible use of the kit.

Pharmaceutical Composition

The construct for expressing alphavirus replicase and/or the replicon described herein may be present in the form of a pharmaceutical composition. A pharmaceutical composition according to the invention may comprise at least one nucleic acid molecule, preferably RNA, according to the present invention. A pharmaceutical composition according to the invention comprises a pharmaceutically acceptable diluent and/or a pharmaceutically acceptable excipient and/or a pharmaceutically acceptable carrier and/or a pharmaceutically acceptable vehicle. The choice of pharmaceutically acceptable carrier, vehicle, excipient or diluent is not particularly limited. Any suitable pharmaceutically acceptable carrier, vehicle, excipient or diluent known in the art may be used.

In one embodiment of the present invention, a pharmaceutical composition can further comprise a solvent such as an aqueous solvent or any solvent that makes it possible to preserve the integrity of the RNA. In a preferred embodiment, the pharmaceutical composition is an aqueous solution comprising RNA. The aqueous solution may optionally comprise solutes, e.g. salts.

In one embodiment of the present invention, the pharmaceutical composition is in the form of a freeze-dried composition. A freeze-dried composition is obtainable by freeze-drying a respective aqueous composition.

In one embodiment, the pharmaceutical composition comprises at least one cationic entity. In general, cationic lipids, cationic polymers and other substances with positive charges may form complexes with negatively charged nucleic acids. It is possible to stabilize the RNA according to the invention by complexation with cationic compounds, preferably polycationic compounds such as for example a cationic or polycationic peptide or protein. In one embodiment, the pharmaceutical composition according to the present invention comprises at least one cationic molecule selected from the group consisting protamine, polyethylene imine, a poly-L-lysine, a poly-L-arginine, a histone or a cationic lipid.

According to the present invention, a cationic lipid is a cationic amphiphilic molecule, e.g., a molecule which comprises at least one hydrophilic and lipophilic moiety. The cationic lipid can be monocationic or polycationic. Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylammonium propane (DOTMA); dimethyldioctadecylammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Cationic lipids also include lipids with a tertiary amine group, including 1,2-dilinoleyloxy-N,N-dimethyl-3-aminopropane (DLinDMA). Cationic lipids are suitable for formulating RNA in lipid formulations as described herein, such as liposomes, emulsions and lipoplexes. Typically positive charges are contributed by at least one cationic lipid and negative charges are contributed by the RNA. In one embodiment, the pharmaceutical composition comprises at least one helper lipid, in addition to a cationic lipid. The helper lipid may be a neutral or an anionic lipid. The helper lipid may be a natural lipid, such as a phospholipid, or an analogue of a natural lipid, or a fully synthetic lipid, or lipid-like molecule, with no similarities with natural lipids. In the case where a pharmaceutical composition includes both a cationic lipid and a helper lipid, the molar ratio of the cationic lipid to the neutral lipid can be appropriately determined in view of stability of the formulation and the like.

In one embodiment, the pharmaceutical composition according to the present invention comprises protamine. According to the invention, protamine is useful as cationic carrier agent. The term "protamine" refers to any of various strongly basic proteins of relatively low molecular weight that are rich in arginine and are found associated especially with DNA in place of somatic histones in the sperm cells of animals such as fish. In particular, the term "protamine" refers to proteins found in fish sperm that are strongly basic, are soluble in water, are not coagulated by heat, and comprise multiple arginine monomers. According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources.

In some embodiments, the compositions of the invention may comprise one or more adjuvants. Adjuvants may be added to vaccines to stimulate the immune system's response; adjuvants do not typically provide immunity themselves. Exemplary adjuvants include without limitation the following: Inorganic compounds (e.g. alum, aluminum hydroxide, aluminum phosphate, calcium phosphate hydroxide); mineral oil (e.g. paraffin oil), cytokines (e.g. IL-1, IL-2, IL-12); immunostimulatory polynucleotide (such as RNA or DNA; e.g., CpG-containing oligonucleotides); saponins (e.g. plant saponins from Quillaja, Soybean, Polygala senega); oil emulsions or liposomes; polyoxy ethylene ether and poly oxy ethylene ester formulations; polyphosphazene (PCPP); muramyl peptides; imidazoquinolone compounds; thiosemicarbazone compounds; the Flt3 ligand (WO 2010/066418 A1); or any other adjuvant that is known by a person skilled in the art. A preferred adjuvant for administration of RNA according to the present invention is the Flt3 ligand (WO 2010/066418 A1). When Flt3 ligand is administered together with RNA that codes for an antigen, a strong increase in antigen-specific CD8+ T cells may be observed.

The pharmaceutical composition according to the invention can be buffered, (e.g., with an acetate buffer, a citrate buffer, a succinate buffer, a Tris buffer, a phosphate buffer).

RNA-Containing Particles

In some embodiments, owing to the instability of non-protected RNA, it is advantageous to provide the RNA molecules of the present invention in complexed or encapsulated form. Respective pharmaceutical compositions are provided in the present invention. In particular, in some embodiments, the pharmaceutical composition of the present invention comprises nucleic acid-containing particles, preferably RNA-containing particles. Respective pharmaceutical compositions are referred to as particulate formulations. In particulate formulations according to the present invention, a particle comprises nucleic acid according to the invention and a pharmaceutically acceptable carrier or a pharmaceutically acceptable vehicle that is suitable for delivery of the nucleic acid. The nucleic acid-containing particles may be, for example, in the form of proteinaceous particles or in the form of lipid-containing particles. Suitable proteins or lipids are referred to as particle forming agents. Proteinaceous particles and lipid-containing particles have been described previously to be suitable for delivery of alphaviral RNA in particulate form (e.g. Strauss & Strauss, Microbiol. Rev., 1994, vol. 58, pp. 491-562). In particular, alphavirus structural proteins (provided e.g. by a helper virus) are a suitable carrier for delivery of RNA in the form of proteinaceous particles.

When the system according to the present invention is formulated as a particulate formulation, it is possible that each RNA species (e.g. replicon, replicase construct, and optional additional RNA species such as an RNA encoding a protein suitable for inhibiting IFN) is separately formulated as an individual particulate formulation. In that case, each individual particulate formulation will comprise one RNA species. The individual particulate formulations may be present as separate entities, e.g. in separate containers. Such formulations are obtainable by providing each RNA species separately (typically each in the form of an RNA-containing solution) together with a particle-forming agent, thereby allowing the formation of particles. Respective particles will contain exclusively the specific RNA species that is being provided when the particles are formed (individual particulate formulations).

In one embodiment, a pharmaceutical composition according to the invention comprises more than one individual particle formulation. Respective pharmaceutical compositions are referred to as mixed particulate formulations. Mixed particulate formulations according to the invention are obtainable by forming, separately, individual particulate formulations, as described above, followed by a step of mixing of the individual particulate formulations. By the step of mixing, one formulation comprising a mixed population of RNA-containing particles is obtainable (for illustration: e.g. a first population of particles may contain replicon according to the invention, and a second formulation of particles may contain replicase construct according to the invention). Individual particulate populations may be together in one container, comprising a mixed population of individual particulate formulations.

Alternatively, it is possible that all RNA species of the pharmaceutical composition (e.g. replicon, replicase construct, and optional additional species such as RNA encoding a protein suitable for inhibiting IFN) are formulated together as a combined particulate formulation. Such formulations are obtainable by providing a combined formulation (typically combined solution) of all RNA species together with a particle-forming agent, thereby allowing the formation of particles. As opposed to a mixed particulate formulation, a combined particulate formulation will typically comprise particles which comprise more than one RNA species. In a combined particulate composition different RNA species are typically present together in a single particle.

In one embodiment, the particulate formulation of the present invention is a nanoparticulate formulation. In that embodiment, the composition according to the present invention comprises nucleic acid according to the invention in the form of nanoparticles. Nanoparticulate formulations can be obtained by various protocols and with various complexing compounds. Lipids, polymers, oligomers, or amphiphiles are typical constituents of nanoparticulate formulations.

As used herein, the term "nanoparticle" refers to any particle having a diameter making the particle suitable for systemic, in particular parenteral, administration, of, in particular, nucleic acids, typically a diameter of 1000 nanometers (nm) or less. In one embodiment, the nanoparticles have an average diameter in the range of from about 50 nm to about 1000 nm, preferably from about 50 nm to about 400 nm, preferably about 100 nm to about 300 nm such as about 150 nm to about 200 nm. In one embodiment, the nanoparticles have a diameter in the range of about 200 to about 700 nm, about 200 to about 600 nm, preferably about 250 to about 550 nm, in particular about 300 to about 500 nm or about 200 to about 400 nm.

In one embodiment, the polydispersity index (PI) of the nanoparticles described herein, as measured by dynamic light scattering, is 0.5 or less, preferably 0.4 or less or even more preferably 0.3 or less. The "polydispersity index" (PI) is a measurement of homogeneous or heterogeneous size distribution of the individual particles (such as liposomes) in a particle mixture and indicates the breadth of the particle distribution in a mixture. The PI can be determined, for example, as described in WO 2013/143555 A1.

As used herein, the term "nanoparticulate formulation" or similar terms refer to any particulate formulation that contains at least one nanoparticle. In some embodiments, a nanoparticulate composition is a uniform collection of nanoparticles. In some embodiments, a nanoparticulate composition is a lipid-containing pharmaceutical formulation, such as a liposome formulation or an emulsion.

Lipid-Containing Pharmaceutical Compositions

In one embodiment, the pharmaceutical composition of the present invention comprises at least one lipid. Preferably, at least one lipid is a cationic lipid. Said lipid-containing pharmaceutical composition comprises nucleic acid according to the present invention. In one embodiment, the pharmaceutical composition according to the invention comprises RNA encapsulated in a vesicle, e.g. in a liposome. In one embodiment, the pharmaceutical composition according to the invention comprises RNA in the form of an emulsion. In one embodiment, the pharmaceutical composition according to the invention comprises RNA in a complex with a cationic compound, thereby forming e.g. so-called lipoplexes or polyplexes. Encapsulation of RNA within vesicles such as liposomes is distinct from, for instance, lipid/RNA complexes. Lipid/RNA complexes are obtainable e.g. when RNA is e.g. mixed with pre-formed liposomes.

In one embodiment, the pharmaceutical composition according to the invention comprises RNA encapsulated in a vesicle. Such formulation is a particular particulate formulation according to the invention. A vesicle is a lipid bilayer rolled up into a spherical shell, enclosing a small space and separating that space from the space outside the vesicle. Typically, the space inside the vesicle is an aqueous space, i.e. comprises water. Typically, the space outside the vesicle is an aqueous space, i.e. comprises water. The lipid bilayer is formed by one or more lipids (vesicle-forming lipids). The membrane enclosing the vesicle is a lamellar phase, similar to that of the plasma membrane. The vesicle according to the present invention may be a multilamellar vesicle, a unilamellar vesicle, or a mixture thereof. When encapsulated in a vesicle, the RNA is typically separated from any external medium. Thus it is present in protected form, functionally equivalent to the protected form in a natural alphavirus. Suitable vesicles are particles, particularly nanoparticles, as described herein.

For example, RNA may be encapsulated in a liposome. In that embodiment, the pharmaceutical composition is or comprises a liposome formulation. Encapsulation within a liposome will typically protect RNA from RNase digestion. It is possible that the liposomes include some external RNA (e.g. on their surface), but at least half of the RNA (and ideally all of it) is encapsulated within the core of the liposome.

Liposomes are microscopic lipidic vesicles often having one or more bilayers of a vesicle-forming lipid, such as a phospholipid, and are capable of encapsulating a drug, e.g. RNA. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. Such phases may be present in nanoparticulate RNA formulations of the present invention.

Liposomes may be formed using standard methods known to the skilled person. Respective methods include the reverse evaporation method, the ethanol injection method, the dehydration-rehydration method, sonication or other suitable methods. Following liposome formation, the liposomes can be sized to obtain a population of liposomes having a substantially homogeneous size range.

In a preferred embodiment of the present invention, the RNA is present in a liposome which includes at least one cationic lipid. Respective liposomes can be formed from a single lipid or from a mixture of lipids, provided that at least one cationic lipid is used. Preferred cationic lipids have a nitrogen atom which is capable of being protonated; preferably, such cationic lipids are lipids with a tertiary amine group. A particularly suitable lipid with a tertiary amine group is 1,2-dilinoleyloxy-N,N-dimethyl-3-aminopropane (DLinDMA). In one embodiment, the RNA according to the present invention is present in a liposome formulation as described in WO 2012/006378 A1: a liposome having a lipid bilayer encapsulating an aqueous core including RNA, wherein the lipid bilayer comprises a lipid with a pKa in the range of 5.0 to 7.6, which preferably has a tertiary amine group. Preferred cationic lipids with a tertiary amine group include DLinDMA (pKa 5.8) and are generally described in WO 2012/031046 A2. According to WO 2012/031046 A2, liposomes comprising a respective compound are particularly suitable for encapsulation of RNA and thus liposomal delivery of RNA. In one embodiment, the RNA according to the present invention is present in a liposome formulation, wherein the liposome includes at least one cationic lipid whose head group includes at least one nitrogen atom (N) which is capable of being protonated, wherein the liposome and the RNA have a N:P ratio of between 1:1 and 20:1. According to the present invention, "N:P ratio" refers to the molar ratio of nitrogen atoms (N) in the cationic lipid to phosphate atoms (P) in the RNA comprised in a lipid containing particle (e.g. liposome), as described in WO 2013/006825 A1.

The N:P ratio of between 1:1 and 20:1 is implicated in the net charge of the liposome and in efficiency of delivery of RNA to a vertebrate cell.

In one embodiment, the RNA according to the present invention is present in a liposome formulation that comprises at least one lipid which includes a polyethylene glycol (PEG) moiety, wherein RNA is encapsulated within a PEGylated liposome such that the PEG moiety is present on the liposome's exterior, as described in WO 2012/031043 A1 and WO 2013/033563 A1.

In one embodiment, the RNA according to the present invention is present in a liposome formulation, wherein the liposome has a diameter in the range of 60-180 nm, as described in WO 2012/030901 A1.

In one embodiment, the RNA according to the present invention is present in a liposome formulation, wherein the RNA-containing liposomes have a net charge close to zero or negative, as disclosed in WO 2013/143555 A1.

In other embodiments, the RNA according to the present invention is present in the form of an emulsion. Emulsions have been previously described to be used for delivery of nucleic acid molecules, such as RNA molecules, to cells. Preferred herein are oil-in-water emulsions. The respective emulsion particles comprise an oil core and a cationic lipid. More preferred are cationic oil-in-water emulsions in which the RNA according to the present invention is complexed to the emulsion particles. The emulsion particles comprise an oil core and a cationic lipid. The cationic lipid can interact with the negatively charged RNA, thereby anchoring the RNA to the emulsion particles. In an oil-in-water emulsion, emulsion particles are dispersed in an aqueous continuous phase. For example, the average diameter of the emulsion particles may typically be from about 80 nm to 180 nm. In one embodiment, the pharmaceutical composition of the present invention is a cationic oil-in-water emulsion, wherein the emulsion particles comprise an oil core and a cationic lipid, as described in WO 2012/006380 A2. The RNA according to the present invention may be present in the form of an emulsion comprising a cationic lipid wherein the N:P ratio of the emulsion is at least 4:1, as described in WO 2013/006834 A1. The RNA according to the present invention may be present in the form of a cationic lipid emulsion, as described in WO 2013/006837 A1. In particular, the composition may comprise RNA complexed with a particle of a cationic oil-in-water emulsion, wherein the ratio of oil/lipid is at least about 8:1 (mole:mole).

In other embodiments, the pharmaceutical composition according to the invention comprises RNA in the format of a lipoplex. The term, "lipoplex" or "RNA lipoplex" refers to a complex of lipids and nucleic acids such as RNA. Lipoplexes can be formed of cationic (positively charged) liposomes and the anionic (negatively charged) nucleic acid. The cationic liposomes can also include a neutral "helper" lipid. In the simplest case, the lipoplexes form spontaneously by mixing the nucleic acid with the liposomes with a certain mixing protocol, however various other protocols may be applied. It is understood that electrostatic interactions between positively charged liposomes and negatively charged nucleic acid are the driving force for the lipoplex formation (WO 2013/143555 A1). In one embodiment of the present invention, the net charge of the RNA lipoplex particles is close to zero or negative. It is known that electro-neutral or negatively charged lipoplexes of RNA and liposomes lead to substantial RNA expression in spleen dendritic cells (DCs) after systemic administration and are not associated with the elevated toxicity that has been reported for positively charged liposomes and lipoplexes (cf. WO 2013/143555 A1). Therefore, in one embodiment of the present invention, the pharmaceutical composition according to the invention comprises RNA in the format of nanoparticles, preferably lipoplex nanoparticles, in which (i) the number of positive charges in the nanoparticles does not exceed the number of negative charges in the nanoparticles and/or (ii) the nanoparticles have a neutral or net negative charge and/or (iii) the charge ratio of positive charges to negative charges in the nanoparticles is 1.4:1 or less and/or (iv) the zeta potential of the nanoparticles is 0 or less. As described in WO 2013/143555 A1, zeta potential is a scientific term for electrokinetic potential in colloidal systems. In the present invention, (a) the zeta potential and (b) the charge ratio of the cationic lipid to the RNA in the nanoparticles can both be calculated as disclosed in WO 2013/143555 A1. In summary, pharmaceutical compositions which are nanoparticulate lipoplex formulations with a defined particle size, wherein the net charge of the particles is close to zero or negative, as disclosed in WO 2013/143555 A1, are preferred pharmaceutical compositions in the context of the present invention.

Methods for Producing a Protein

In a fourth aspect, the invention provides a method for producing a protein in a cell comprising the steps of:
  (a) obtaining an RNA construct for expressing alphavirus replicase,
  (b) obtaining an RNA replicon that can be replicated by the replicase in trans and comprises an open reading frame encoding the protein, and
  (c) co-inoculating the RNA construct for expressing alphavirus replicase and the RNA replicon into the cell, wherein the RNA construct for expressing alphavirus replicase comprises a 5'-cap for driving translation of the replicase.

The RNA construct for expressing alphavirus replicase according to (a) may be characterized by any one or more of the features of the replicase construct comprised in the system according to the first aspect of the present invention.

The RNA replicon according to (b) may be characterized by any one or more of the features of the replicon comprised in the system according to the first aspect of the present invention.

In one embodiment, the RNA construct for expressing alphavirus replicase according to (a) and the RNA replicon according to (b) used in the method for producing a protein in a cell are constituents of the system according to the present invention.

The cell into which one or more nucleic molecule can be inoculated can be referred to as "host cell". According to the invention, the term "host cell" refers to any cell which can be transformed or transfected with an exogenous nucleic acid molecule. The term "cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. The term "host cell" comprises, according to the invention, prokaryotic (e.g. *E. coli*) or eukaryotic cells (e.g. human and animal cells, and insect cells). Particular preference is given to mammalian cells such as cells from humans, mice, hamsters, pigs, domesticated animals including horses, cows, sheep and goats, as well as primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, in particular a dendritic cell, a monocyte or a macrophage. A nucleic acid may be present in the host cell in a single or in several copies and, in one embodiment is expressed in the host cell.

The cell may be a prokaryotic cell or a eukaryotic cell. Prokaryotic cells are suitable herein e.g. for propagation of DNA according to the invention, and eukaryotic cells are suitable herein e.g. for expression of the open reading frame of the replicon.

In the method of the present invention, any of the system according to the invention, or the kit according to the invention, or the pharmaceutical composition according to the invention, can be used. RNA can be used in the form of a pharmaceutical composition, or as naked RNA e.g. for electroporation. Inoculation of compositions comprising RNA into cells as well as electroporation of naked RNA into cells has been previously described (see references cited herein in the section describing pharmaceutical compositions according to the present invention).

According to the method of the present invention, efficient expression of a gene of interest in a host cell can be achieved (see e.g. Examples 1 and 2).

In the method for producing a protein in a cell according to the present invention, the different RNA molecules according to the first aspect (replicon and replicase construct) can either be inoculated at the same point in time, or they may alternatively be inoculated at different points in time. In the second case, the replicase construct is typically inoculated at a first point in time, and the replicon is typically inoculated at a second, later, point in time. In that case, it is envisaged that the replicon will be immediately replicated since replicase will already have been translated in the cell. The second point in time is typically shortly after the first point in time, e.g. 1 minute to 24 hours after the first point in time.

In one embodiment, an additional RNA molecule, preferably an mRNA molecule, may be inoculated with the cell. Optionally, the additional RNA molecule encodes a protein suitable for inhibiting IFN, such as E3, as described herein. Optionally, the additional RNA molecule may be inoculated prior to inoculation of the replicon or of the replicase construct or of the system according to the invention.

In the method for producing a protein in a cell according to the present invention, the cell may be an antigen presenting cell, and the method may be used for expressing the RNA encoding the antigen. To this end, the invention may involve introduction of RNA encoding antigen into antigen presenting cells such as dendritic cells. For transfection of antigen presenting cells such as dendritic cells a pharmaceutical composition comprising RNA encoding the antigen may be used.

In one embodiment, the method for producing a protein in a cell is an in vitro method. In one embodiment, the method for production of a protein in a cell does not comprise the removal of a cell from a human or animal subject by surgery or therapy.

In this embodiment, the cell inoculated according to the fourth aspect of the invention may be administered to a subject so as to produce the protein in the subject and to provide the subject with the protein. The cell may be autologous, syngenic, allogenic or heterologous with respect to the subject.

In another embodiment, the cell in the method for producing a protein in a cell may be present in a subject, such as a patient. In this embodiment, the method for producing a protein in a cell is an in vivo method which comprises administration of RNA molecules to the subject.

In this respect, the invention also provides a method for producing a protein in a subject comprising the steps of:
(a) obtaining an RNA construct for expressing alphavirus replicase,
(b) obtaining an RNA replicon that can be replicated by the replicase in trans and comprises an open reading frame encoding the protein, and
(c) administering the RNA construct for expressing alphavirus replicase and the RNA replicon to the subject, wherein the RNA construct for expressing alphavirus replicase comprises a 5'-cap for driving translation of the replicase.

The RNA construct for expressing alphavirus replicase according to (a) may be characterized by any one or more of the features of the replicase construct comprised in the system according to the first aspect of the present invention. The RNA construct according to (a) may be obtained e.g. as described herein.

The RNA replicon according to (b) may be characterized by any one or more of the features of the replicon comprised in the system according to the first aspect of the present invention. Preferably, the replicon according to (b) encodes a pharmaceutically active peptide or protein as a protein of interest. In one embodiment, the pharmaceutically active peptide or protein is an immunologically active compound or an antigen. The RNA replicon according to (b) may be obtained e.g. as described herein. The method for producing a protein in a subject according to the present invention is particularly suitable for prophylactic as well as in therapeutic applications. Preferably, in the method for producing a protein in a subject, the RNA replicon encodes, as gene of interest, a pharmaceutically active protein or polypeptide.

In the method for producing a protein in a subject, the RNA replicase construct according to (a) and the replicon according to (b) can either be administered at the same point in time, or may alternatively be administered at different points in time. In the second case, the replicase construct according to (a) is typically administered at a first point in time, and the replicon according to (b) is typically administered at a second, later, point in time. In that case, it is envisaged that the replicon will be immediately replicated since replicase will already have been translated in the cell. The second point in time is typically shortly after the first point in time, e.g. 1 minute to 24 hours after the first point in time. Preferably the administration of the replicon is performed at the same site and via the same route of administration as the administration of the replicase construct, in order to increase the prospects that the replicon and the replicase construct reach the same target tissue or cell. "Site" refers to the position of a subject's body. Suitable sites are for example, the left arm, right arm, etc.

In one embodiment, an additional RNA molecule, preferably an mRNA molecule, may be administered to the subject. Optionally, the additional RNA molecule encodes a protein suitable for inhibiting IFN, such as E3, as described herein. Optionally, the additional RNA molecule may be administered prior to administration of the replicon or of the replicase construct or of the system according to the invention.

Any of the system according to the invention, or the kit according to the invention, or the pharmaceutical composition according to the invention can be used in the method for producing a protein in a subject according to the invention. For example, in the method of the invention, RNA can be used in the format of a pharmaceutical composition, e.g. as described herein, or as naked RNA. The administration of pharmaceutical compositions comprising RNA has been previously described, see e.g. references cited herein in the section describing pharmaceutical compositions according to the present invention.

In view of the capacity to be administered to a subject, each of the system according to the invention, or the kit according to the invention, or the pharmaceutical composition according to the invention, may be referred to as "medicament", or the like. The present invention foresees that the system, the kit, and/or the pharmaceutical composition, of the present invention are provided for use as a medicament. The medicament can be used to treat a subject. By "treat" is meant to administer a compound or composition or other entity as described herein to a subject. The term includes methods for treatment of the human or animal body by therapy.

The above-described medicament does typically not comprise a DNA, and is thus associated with additional safety features compared to DNA vaccines described in the prior art (e.g. WO 2008/119827 A1).

An alternative medical use according to the present invention comprises a method for producing a protein in a cell according to the fourth aspect of the present invention, wherein the cell may be an antigen presenting cell such as a dendritic cell, followed by the introduction of said cell to a subject. For example, a system comprising a replicon encoding a pharmaceutically active protein, such as an antigen, may be introduced (transfected) into antigen-presenting cells ex vivo, e.g. antigen-presenting cells taken from a subject, and the antigen-presenting cells, optionally clonally propagated ex vivo, may be reintroduced into the same or a different subject. Transfected cells may be reintroduced into the subject using any means known in the art.

The medicament according to the present invention may be administered to a subject in need thereof. The medicament of the present invention can be used in prophylactic as well as in therapeutic methods of treatment of a subject.

The medicament according to the invention is administered in an effective amount. An "effective amount" concerns an amount that is sufficient, alone or together with other doses, to cause a reaction or a desired effect. In the case of treatment of a certain disease or a certain condition in a subject, the desired effect is the inhibition of disease progression. This includes the deceleration of disease progression, in particular the interruption of disease progression.

The desired effect in the treatment of a disease or a condition can also be a delay of disease outbreak or the inhibition of disease outbreak.

The effective amount will depend on the condition being treated, the severity of the disease, the individual parameters of the patient, including age, physiological condition, size and weight, duration of the treatment, type of accompanying therapy (if any), the specific mode of administration and other factors.

Vaccination

The term "immunization" or "vaccination" generally refers to a process of treating a subject for therapeutic or prophylactic reasons. A treatment, particularly a prophylactic treatment, is or comprises preferably a treatment aiming to induce or enhance an immune response of a subject, e.g. against one or more antigens. If, according to the present invention, it is desired to induce or enhance an immune response by using RNA as described herein, the immune response may be triggered or enhanced by the RNA. In one embodiment, the invention provides a prophylactic treatment which is or comprises preferably the vaccination of a subject. An embodiment of the present invention wherein the replicon encodes, as a protein of interest, a pharmaceutically active peptide or protein which is an immunologically active compound or an antigen is particularly useful for vaccination.

RNA has been previously described for vaccination against foreign agents including pathogens or cancer (reviewed recently by Ulmer et al., 2012, Vaccine, vol. 30, pp. 4414-4418). In contrast to common approaches in the prior art, the replicon according to the present invention is a particularly suitable element for efficient vaccination because of the ability to be replicated in trans by the replicase encoded by the replicase construct of the present invention. The vaccination according to the present invention can be used for example for induction of an immune response to weakly immunogenic proteins. In the case of the RNA vaccines according to the invention, the protein antigen is never exposed to serum antibodies, but is produced by transfected cells themselves after translation of the RNA. Therefore anaphylaxis should not be a problem. The invention therefore permits the repeated immunization of a patient without risk of allergic reactions.

Example 5 of the present invention makes plausible that the transgene-containing replicon reaches high copy numbers in vaccinated animals, as evident from very strong expression of recombinant protein. Example 6 evidences that vaccination according to the present invention, wherein the replicon encodes a therapeutic protein, is very efficient. Thus, the present invention enables the efficient vaccination with an alphavirus-based trans-replication RNA system.

In methods involving vaccination according to the present invention, the medicament of the present invention is administered to a subject, in particular if treating a subject having a disease involving the antigen or at risk of falling ill with the disease involving the antigen is desired.

In methods involving vaccination according to the present invention, the protein of interest encoded by the replicon according to the present invention codes for example for a bacterial antigen, against which an immune response is to be directed, or for a viral antigen, against which an immune response is to be directed, or for a cancer antigen, against which an immune response is to be directed, or for an antigen of a unicellular organism, against which an immune response is to be directed. The efficacy of vaccination can be assessed by known standard methods such as by measurement of antigen-specific IgG antibodies from the organism.

In methods involving allergen-specific immunotherapy according to the present invention, the protein of interest encoded by the replicon according to the present invention codes for an antigen relevant to an allergy. Allergen-specific immunotherapy (also known as hypo-sensitization) is defined as the administration of preferably increasing doses of an allergen vaccine to an organism with one or more allergies, in order to achieve a state in which the symptoms that are associated with a subsequent exposure to the causative allergen are alleviated. The efficacy of an allergen-specific immunotherapy can be assessed by known standard methods such as by measurement of allergen-specific IgG and IgE antibodies from the organism.

The medicament of the present invention can be administered to a subject, e.g. for treatment of the subject, including vaccination of the subject.

The term "subject" relates to vertebrates, particularly mammals. For example, mammals in the context of the present invention are humans, non-human primates, domesticated mammals such as dogs, cats, sheep, cattle, goats, pigs, horses etc., laboratory animals such as mice, rats, rabbits, guinea pigs, etc. as well as animals in captivity such as animals of zoos. The term "subject" also relates to non-mammalian vertebrates such as birds (particularly domesticated birds such as chicken, ducks, geese, turkeys) and to fish (particularly farmed fish, e.g. salmon or catfish). The term "animal" as used herein also includes humans.

The administration to domesticated animals such as dogs, cats, rabbits, guinea pigs, hamsters, sheep, cattle, goats, pigs, horses, camels, chicken, ducks, geese, turkeys, or wild animals, e.g. foxes, deers, roe deers, wild boars, is preferred in some embodiments. For example, a prophylactic vaccination according to the present invention may be suitable to vaccinate an animal population, e.g. in the farming industry, or a wild animal population. Other animal populations in captivity, such as pets, or animals of zoos, may be vaccinated.

When administered to a subject, the replicon and/or the replicase construct used as a medicament do preferably not comprise sequences from a type of alphavirus that is infectious to the species or genus to which the treated subject belongs. Preferably, in that case, the replicon and/or the replicase construct do not comprise any nucleotide sequence from an alphavirus that can infect the respective species or genus. This embodiment bears the advantage that no recombination with infectious (e.g. fully functional or wild-type) alphavirus is possible, even if the subject to which the RNA is administered is (e.g. accidentally) affected by infectious alphavirus. As an illustrative example, for treatment of pigs, the replicon and/or the replicase construct used do not comprise any nucleotide sequence from an alphavirus that can infect pigs.

Mode of Administration

The medicament according to the present invention can be applied to a subject in any suitable route.

For example, the medicament may be administered systemically, for example intravenously (i.v.), subcutaneously (s.c.), intradermally (i.d.) or by inhalation.

In one embodiment, the medicament according to the present invention is administered to muscle tissue, such as skeletal muscle, or skin, e.g. subcutaneously. It is generally understood that transfer of RNA into the skin or muscles leads to high and sustained local expression, paralleled by a strong induction of humoral and cellular immune responses (Johansson et al. 2012, PLoS. One., 7, e29732; Geall et al., 2012, Proc. Natl. Acad. Sci. U.S.A, vol. 109, pp. 14604-14609).

Alternatives to administration to muscle tissue or skin include, but are not limited to: intradermal, intranasal, intraocular, intraperitoneal, intravenous, interstitial, buccal, transdermal, or sublingual administration. Intradermal and intramuscular administration are two preferred routes.

Administration can be achieved in various ways. In one embodiment, the medicament according to the present invention is administered by injection. In a preferred embodiment, injection is via a needle. Needle-free injection may be used as an alternative.

The present invention is described in detail and is illustrated by the figures and examples, which are used only for illustration purposes and are not meant to be limiting. Owing to the description and the examples, further embodiments which are likewise included in the invention are accessible to the skilled worker.

EXAMPLES

Material and Methods

The following materials and methods were used in the examples that are described below.

DNA Encoding Replicon, Replicase Construct and E3L; and In Vitro Transcription (1) DNA encoding a cis-replicon used in the examples was prepared as follows: a DNA plasmid suitable for in vitro transcription of an RNA replicon that is capable of being replicated by Semliki Forest virus (SFV) replicase was prepared: A reference Semliki Forest virus replicon plasmid (pSFV-gen-GFP) was kindly provided by K. Lundstrom (Lundstrom et al., 2001, Histochem. Cell Biol., vol. 115, pp. 83-91; Ehrengruber & Lundstrom, 1999, Proc. Natl. Acad. Sci. U.S.A, vol. 96, pp. 7041-7046). The pSFV-gen-GFP-encoded poly(A) cassette was elongated from 62 adenylate residues in the original vector to 120 adenylate residues, and a SapI restriction site was placed immediately downstream of the poly(A) cassette. This poly(A) design was described to enhance expression of synthetic mRNA (Holtkamp et al., 2006, Blood, vol. 108, pp. 4009-4017). Finally the phage-polymerase promoter was changed from SP6 to T7.

(2) DNA encoding trans-replicons were engineered from above described cis-replicon by deleting major parts of the open reading frame encoding alphavirus replicase (nucleotides 222-6321 of the replicase ORF) while keeping the vector backbone.

(1a, 2a) We independently cloned the reporter genes firefly luciferase, secretable NanoLuc, (both commercialized by Promega, Madison, Wis., USA), Influenza virus A/Puerto Rico/08/1934 hemagglutinin (HA) and enhanced green fluorescent protein (eGFP, in the figures either "GFP" or "eGFP") 3' to the subgenomic promoter of cis- and trans-replicons.

(3) To create a replicase construct, an open reading frame encoding the SFV replicase was cloned into a pST1 plasmid characterized by a tandem copy of the human beta-globin 3'UTR, a poly($A_{120}$) tail and a SapI restriction site immediately downstream of the poly(A) tail (Holtkamp et al., 2006, Blood, vol. 108, pp. 4009-4017).

(4) An open reading frame encoding vaccinia virus E3L was cloned into a pST1 plasmid characterized by a tandem copy of the human beta-globin 3'UTR, a poly($A_{120}$) tail and a SapI restriction site immediately downstream of the poly (A) tail (Holtkamp et al., 2006, Blood, vol. 108, pp. 4009-4017).

In vitro transcription from pST1-derived and pSFV-gen-GFP derived plasmids [(1a), (2a), (3) and (4)] and purification of RNA was performed as previously described with the exception that beta-S-ARCA(D2) cap analog was used instead of ARCA (Holtkamp et al., supra; Kuhn et al., 2010, Gene Ther., vol. 17, pp. 961-971). Quality of purified RNA was assessed by spectrophotometry, and analysis on the 2100 BioAnalyzer (Agilent, Santa Clara, USA). The RNA used in the examples is purified IVT-RNA.

RNA Transfer into Cells:

For electroporation, RNA was electroporated into cells at room temperature using a square-wave electroporation device (BTX ECM 830, Harvard Apparatus, Holliston, Mass., USA) using the following settings: 750 V/cm, 1 pulse of 16 milliseconds (ms)). For electroporation, RNA was resuspended in a final volume of 62.5 µl/mm cuvette gap size.

RNA lipofections were performed using Lipofectamine RNAiMAX following the manufacturer's instructions (Life Technologies, Darmstadt, Germany). Cells were plated at approximately 20,000 cells/cm$^2$ growth area and transfected with a total amount of 260 ng/cm$^2$ RNA and 1 µl/cm$^2$ RNAiMAX. RNA species were mixed in RNAse-free Eppendorf tubes and kept on ice until used for transfection.

Cell culture: All growth media, fetal calf serum (FCS), antibiotics and other supplements were supplied by Life Technologies/Gibco, except when stated otherwise. Human foreskin fibroblasts obtained from System Bioscience (HFF, neonatal) or ATCC (CCD-1079Sk) were cultivated in minimum essential media (MEM) containing 15% FCS, 1 units/ml penicillin, 1 µg/ml streptomycin, 1% non-essential amino acids, 1 mM sodium pyruvate at 37° C. Cells were grown at 37° C. in humidified atmosphere equilibrated to 5% CO2. BHK21 cells (ATCC; CCL10) were grown in Eagle's Minimum Essential medium supplemented with 10% FCS.

Flow cytometry: Unless indicated otherwise, transfected cells were harvested 16 h after transfection to measure efficiencies of productive transfections and transgene (eGFP) expression by flow cytometry (FACS). The measurement was performed by flow cytometry using a FACS Canto II flow cytometer (BD Bioscience, Heidelberg, Germany), and acquired data were analyzed by the corresponding Diva software or FlowJo software (Tree Star Inc., Ashland, Oreg., USA).

Luciferase Assays: To assess the expression of luciferase in transfected cells, transfected cells were plated in 96-well white microplates (Nunc, Langenselbold, Germany). The detection of firefly luciferase was performed with the Bright-Glo Luciferase Assay System; NanoLuc was detected using the NanoGlo kit (both Promega, Madison, Wis., USA) according to the manufacturer's instructions. Bioluminescence was measured using a microplate luminescence reader Infinite M200 (Tecan Group, Männedorf, Switzerland). Data are represented in relative luciferase units [RLU], Luciferase-negative cells were used to subtract the background signal.

Animals: Balb/c mice, 6-8 weeks of age, were purchased from Janvier LABS (Saint Berthevin Cedex, France) and housed under normal laboratory conditions with circadian light/dark cycles and free access to standard mouse chow and tap water. All experiments were approved by the Regional Council's Ethics Committee for Animal Experimentation (Koblenz/Rhineland-Palatinate, Germany, G 13-8-063).

Influenza virus production and titer determination. For infection, Madin-Darby canine kidney II (MDCK-II) cells were cultivated in MEM containing 0.2% bovine serum albumin (30% especially IgG-free BSA; Sigma) instead of FCS (infection medium). Mouse-adapted Influenza virus A/Puerto Rico/08/1934 was propagated in MDCK-II cells in infection medium containing 1 µg/ml tosylsulfonyl phenylalanyl chloromethyl ketone (TPCK)-trypsin (Sigma). Cell supernatants were cleared by low-speed centrifugation and stored at −80° C. Viral titers (plaque-forming units (PFU) per ml) were determined with plaque assay using MDCK-II cell monolayers of 70-80% confluence(12-well plate). Cells were inoculated with 200 µl of a serial 10 fold dilution of virus preparations ($10^{-2}$ to $10^{-8}$). Virus was allowed to adsorb for 1 h at 37° C., before cells were overlaid with low-viscosity medium Avicel to reduce viral diffusion and allow plaque formation. 2,4% Avicel solution was diluted with 2×MEM/1 µg/ml TPCK-Trypsin to reach a final Avicel-concentration of 1,2%. Three days later overlays were removed and cells were stained using an aqueous 1 crystal violet solution containing 10% formaldehyde (10 min at RT). Stained cells were washed with water, plaques per well were counted and PFU/ml was calculated.

Hemagglutination titer (HA titer): Hemagglutination units (HAU) were determined using chicken red blood cells (RBC; Fitzgerald, USA) according to the recommendations published by the WHO in 2011 in the "Manual for the laboratory diagnosis and virological surveillance of influenza". Briefly, a serial dilution of virus preparations (2-fold) was performed in V-shaped 96-well plates and then incubated with 50 µl of 0.5% chicken RBC ("standardized RBC") for 30 min at 25° C. Hemagglutination was considered to be complete, when RBC were still in suspension after the incubation with the virus preparation whereas non-agglutinated RBCs settled at the bottom of the wells. The HA titer was recorded as the inverse of the lowest dilution that showed complete agglutination and defined as one Hemagglutination unit (HAU) per 50 µl, the amount of virus that is necessary to agglutinate an equal volume of standardized RBC.

Hemagglutination inhibition (HAI) Assay. To determine the serum level of anti-HA antibodies that inhibit hemagglutination in immunized mice, sera were collected and treated over night with receptor destroying enzyme II "Seiken" in a 1:5 ratio (RDE (II), Denka Seiken Co. Ltd., Japan) followed by heat inactivation for 30 min at 56° C. Sera were used in duplicates and serial dilutions (1:2) were performed before adding of 25 µl PR8 virus dilution (4 HAU/50 µl). After 15 min incubation at room temperature, 50 µl of 0.5% RBC was added and the mixture incubated for 30 minutes before evaluation of agglutination. The HAI titer was recorded as the inverse of the lowest dilution that inhibited agglutination (HAI/50 µl).

Virus neutralization titer (VNT) determination: To determine the titer of virus neutralizing antibodies in the serum of vaccinated mice we assayed the ability of serum antibodies to prevent the infection of and thus the de novo virus release from Madin-Darby canine kidney (MDCK) cells. To this aim serial 1:2 dilutions of heat-inactivated sera (56° C. for 30 min) from vaccinated and control mice were incubated with a fixed concentration of infectious influenza virus (2 $TCID_{50}$/µl) (tissue-culture infectious dose(50)). Controls include a no serum and a no virus control on each microtiter plate, as well as a back-titration of the virus preparation in absence of serum to confirm the titer of the virus preparation. All preparations (serum-virus mixtures and control samples) were incubated 2 h at 37° C. in presence of 1 µg/ml tosylsulfonyl phenylalanyl chloromethyl ketone (TPCK)-trypsin before exposing MDCK cells for 3 days at 37° C. to the preparation. After 3 days the cell culture supernatants were harvested from MDCK cells and subjected to a HA titer determination as described above.

Intradermal immunizations, viral challenge infections and evaluation of animals: Female BALB/c mice aged 8-10 weeks were used for immunization experiments. Mice were anesthetized by isoflurane inhalation, the dorsal area was shaved, and HA-Replicon RNA in combination with replicase and E3 mRNA, dissolved in 20 µl RNAse-free PBS, were injected intradermally on day 0 and 21. Blood was taken under isoflurane anesthesia by orbital venous plexus bleeding on days 20, 35 and 55 after the first immunization. Cellular debris was pelleted from the blood by centrifugation, and serum samples were directly used for hemagglutinin (HAI) assay. To evaluate protection against infection with Influenza virus, immunized mice were challenged intranasally with a 10-fold $LD_{50}$ of mouse-adapted Influenza virus A/Puerto Rico/08/1934 (PR8) while anesthetized with ketamine/Xylazin. Mice were weighed daily and euthanized 14 days after challenge or when the termination criterion (25% weight loss) was fulfilled.

Example 1: Efficiency of Transgene Expression is Dependent on the Type of RNA Molecule that Encodes the Replicase RNA cis-replicon encoding replicase and encoding luciferase downstream of the SGP ("cis-replicon RNA") or synthetic mRNA encoding replicase ("mRNA"), each together with RNA trans-replicon encoding eGFP downstream of the SGP were introduced by electroporation into BHK21 cells (FIG. 3). The expression of the trans-replicon was determined by measuring fluorescence of eGFP by FACS, the expression of luciferase from the cis-replicon was not of interest. In particular, the success of the experiment was quantified by determining the transfection rate, which is reflected by the percentage of eGFP positive cells (bars in FIG. 3); and by determining the expression level of eGFP, which is reflected by the mean fluorescence intensity (MFI) of the eGFP positive cells (rhombi in FIG. 3). As shown in FIG. 3, the trans-replication system (wherein the replicase is provided in trans in the form of mRNA) yielded both a higher percentage of eGFP positive cells as well as a higher mean fluorescence intensity of eGFP-positive cells compared to replicase expressed from a replicon capable of cis-replication ("cis-replicon RNA"). Thus, the replicase expressed from a replicon capable of cis-replication is less potent to amplify the subgenomic transcript of a trans-replicon, resulting in lower level of transgene expression. Additionally, a system comprising replicase mRNA and trans-replicon RNA, co-delivered into BHK21 cells, is more likely to productively replicate the trans-replicon, as deduced from the percentage of eGFP positive cells (bars in FIG. 3).

In summary, it was concluded that expression of the gene of interest in a trans-replication system is more efficient when using mRNA to deliver replicase.

Example 2: The Trans-Replication System Composed of Replicase Encoded by mRNA and a Trans-Replicon Encoding the Transgene Provides High Level of Transgene Expression Also in Primary Cells, and Results in Higher Expression Compared to a Cis-Replicon Encoding the Transgene RNA replicon capable of cis-replication ("eGFP-replicon RNA"); or mRNA encoding replicase ("Replicase mRNA") together with RNA trans-replicon ("eGFP transreplicon RNA") were transfected into primary human foreskin fibroblasts (FIG. 4). In order to reduce activity of protein kinase R, mRNA encoding Vaccinia virus protein E3 was added to each RNA sample. The transfection was performed by combining RNA or mixtures of RNA with RNAiMAX transfection reagent and adding this formulation to the medium of cells (thus presumably a co-delivery of RNAs in the same liposomes).

The expression of the gene of interest was determined by measuring fluorescence of eGFP, i.e. by determining the percentage of eGFP positive cells (bars in FIG. 4); and by determining the mean fluorescence intensity (MFI) of the eGFP positive cells (rhombi in FIG. 4). The trans-replication system ("eGFP transreplicon RNA" together with "Replicase mRNA") yielded both a higher percentage of eGFP positive cells as well as a higher mean fluorescence intensity of eGFP-positive cells than the cis-replication system ("eGFP-replicon RNA"). Thus, in the case of the trans-replication system, the probability is higher that productive replication of the transgene-encoding RNA will occur. In both systems the probability to establish productive replication is dose-dependent, but 50 ng trans-replicon RNA is approximately as potent as 625 ng reference replicon (cis-replicon); and 10 ng trans-replicon is as potent as 500 ng reference replicon. In addition, the trans-replication system yields higher transgene expression levels per cell (reflected by the MFI) than the reference replicon (rhombi in FIG. 4).

Example 3: Production of the Protein of Interest is Dependent on the Dose of Replicase RNA encoding replicase ("Replicase mRNA") together with RNA trans-replicon ("Transreplicon") and E3 mRNA were lipofected into primary human foreskin fibroblasts, as indicated in FIG. 5A. The RNA trans-replicon encodes the secretable reporter protein NanoLuc luciferase as gene of interest. The efficiency of protein production can be modulated by the amount of replicase RNA in a dose dependent manner, as demonstrated by the measurement of secreted NanoLuc (FIG. 5A).

Example 4: Modifying the Codon Usage of the Replicase Construct is a Disadvantageous Non-Polypeptide-Sequence Modifying Modification In this example, a trans-replication system was used wherein the replicase construct encodes a myc-tagged nsP3. The myc-tag was inserted into the variable region of nsP3 to allow detection of the levels of nsP3 (reflecting total replicase amounts) by Western Blot with anti-myc antibodies. Insertions into the nsP3 variable region do not affect the activity of the replicase polyprotein (Spuul et al., 2010, J. Virol, vol. 85, pp. 7543-7557). The codon usage of the myc-tagged replicase ("Replicase wt codon usage") was optionally adapted to Homo sapiens codon usage (to yield "Replicase hs codon usage"). A trans-replicon encoding eGFP as gene of interest was co-lipofected into BHK21 cells together with different amounts of replicase RNA, as indicated (FIG. 5B).

The expression of the gene of interest was determined by measuring fluorescence of eGFP, i.e. by determining the percentage of eGFP positive cells (bars in FIG. 5B); and by determining the mean fluorescence intensity (MFI) of the eGFP positive cells (rhombi in FIG. 5B).

Modification of the codon usage leads to increased replicase levels (levels of myc-tagged nsP3) but this is not advantageous for the expression of the gene of interest from a eGFP-encoding trans-replicon: the much higher replicase-expression from codon-optimized RNA compared to non-codon optimized replicase RNA is not reflected by higher eGFP expression (rhombi in FIG. 5B), and the probability to establish productive replication of trans-replicon is decreased, as shown by percentage of eGFP positive cells (bars in FIG. 5B).

Example 5: Efficient Expression of a Transgene Encoded by a Replicon According to the Present Invention can be Achieved In Vivo IVT RNA encoding replicase together with RNA trans-replicon and with mRNA encoding Vaccinia virus protein E3 were resuspended in phosphate buffered saline (PBS) and co-injected into mice, intradermally or into the tibialis anterior (intramuscular). The open reading frame of the trans-replicon encodes the reporter protein luciferase as protein of interest.

Two groups with 3 animals per group were used. Each animal was injected at two positions. In vivo luciferase expression was measured as described (Kuhn et al., 2010, Gene Ther., vol. 17, pp. 961-971). The expression lasts for at least 9 days, as shown by bioluminescence imaging (BLI) of mice after intramuscular (i.m.) and intradermal (i.d.), respectively, co-injection of the RNAs. Results are shown in FIG. 6.

Example 6: Vaccination with a Trans-Replication System Comprising a Replicon According to the Present Invention Encoding Influenza HA as Protein of Interest Provides Protection from Lethal Virus Infections Balb/C mice were vaccinated intradermally twice (prime-boost) within 3 weeks with RNA replicon encoding hemagglutinin (HA) as gene of interest (in FIG. 7: "R-HA"); or with RNA encoding replicase (in FIG. 7: "Replicase") and with trans-replicon RNA encoding hemagglutinin (HA) as gene of interest (in FIG. 7: "TR-HA"), as indicated in FIG. 7. To enhance translation, Vaccinia virus E3 encoding mRNA was co-transfected, where indicated. Control animals were either vaccinated with inactivated virus (IAV) or received solvent (PBS).

The day before challenge infections with lethal doses of Influenza virus, sera of all animals were collected and used to determine the virus neutralization titer (VNT). In the reference replicon group all animals show a VNT approaching titers of IAV treated animals. In the trans-replicon group, the VNT increased the more replicase mRNA was co-transferred. With a 14-fold excess of replicase mRNA with respect to the trans-replicon, a VNT as high as in the Replicon controls was achieved, which means that only 20% of antigen coding RNA (1 μg TR-HA vs. 5 μg R-HA) resulted in comparable VNT titers (FIG. 7A).

Mouse sera were also subjected to a hemagglutinin inhibition (HAI) assay. All RNA vaccinated animals showed comparable HAI titers (FIG. 7B).

Survival of the mice following challenge infections was monitored. Buffer treated mice died within 5 days. All vaccinated mice survived, with one exception in the group vaccinated with TR-HA and 15 μg E3 (FIG. 7C).

In summary, it was concluded that vaccination with the trans-replicon encoding HA provides protection from lethal virus infection and allows reduction of the amount of antigen coding RNA.

Example 7: Influence of the Cap

BHK21 cells were electroporated with transreplicon RNA encoding eGFP and secNLuc (secretable luciferase) separated by the self-cleaving peptide P2A (porcine teschovirus-1 2A) together with either beta-S-ARCA(D2) capped replicase mRNA or uncapped mRNA with IRES(EMCV) (internal ribosomal entry site from encephalomyocarditis virus) upstream of the replicase ORF. 24 h after electroporation cells were analysed by FACS for eGFP expression (FIG. 8A), supernatants were analysed for secretion levels of secNLuc by Nano-Glo® Luciferase Assay System (Promega) (FIG. 8B) and the replicase expression was analysed by Western blot (FIG. 8C).

As demonstrated in FIG. 8A, capped replicase mRNA leads to a higher probability to establish transreplicon replication as measured by the percentage of eGFP positive (bars) and to higher eGFP expression levels in positive cells (rhombi).

To quantify the difference, the activity of secreted luciferase was measured and revealed that both replicase mRNAs are functional (the assay background is ~10 RLU) but the described transreplicating system is 37 fold more potent when capped mRNA is used as demonstrated in FIG. 8B.

As demonstrated in FIG. 8C, the reason for the above observation is the higher replicase protein concentration when expression is driven by a cap (left lane) compared to an IRES (right lane) as shown by probing the samples with an anti myc antibody (upper blot). Probing the samples with an anti eGFP antibody (middle blot) confirmed higher eGFP expression as already shown in FIG. 8A. Equal loading of the gel is confirmed by the detection of cellular protein α-Tubulin with a corresponding antibody (lower blot).

The invention claimed is:

1. A system comprising:
   (a) an intron-free mRNA construct for expressing alphavirus replicase comprising
      (i) a non-viral 5' UTR,
      (ii) an open reading frame encoding the replicase, and
      (iii) a non-viral 3' UTR, and
   wherein the mRNA construct for expressing alphavirus replicase does not comprise an internal ribosomal entry site (IRES) element for driving translation of the replicase; and
   (b) a RNA replicon that can be replicated by the replicase in trans,
   wherein the mRNA construct of (a) for expressing alphavirus replicase comprises a 5'-cap for driving translation of the replicase.

2. The system according to claim 1, wherein the 5'-cap is a natural 5'-cap or a 5'-cap analog.

3. The system according to claim 1, wherein the open reading frame encoding the alphavirus replicase comprises the coding region(s) for non-structural proteins required for RNA replication.

4. The system according to claim 1, wherein the mRNA construct for expressing alphavirus replicase comprises a 3' poly(A) sequence.

5. The system according to claim 1, wherein the mRNA construct for expressing alphavirus replicase cannot be replicated by the replicase.

6. The system according to claim 1, wherein the RNA replicon comprises:
   (1) an alphavirus 5' replication recognition sequence, and
   (2) an alphavirus 3' replication recognition sequence.

7. The system according to claim 6, wherein the alphavirus 5' replication recognition sequence and the alphavirus 3' replication recognition sequence direct replication of the RNA replicon in the presence of the replicase, and/or wherein the alphavirus 5' replication recognition sequence and the alphavirus 3' replication recognition sequence are native to the alphavirus from which the replicase is derived.

8. The system according to claim 1, wherein the RNA replicon comprises a heterologous nucleic acid.

9. The system according to claim 1, wherein the RNA replicon comprises an open reading frame encoding a protein of interest.

10. The system according to claim 9, wherein the open reading frame encoding a protein of interest is non-native to the alphavirus from which the replicase is derived, and/or wherein expression of the open reading frame encoding a protein of interest is under the control of a subgenomic promoter.

11. The system according to claim 10, wherein the subgenomic promoter is native to the alphavirus from which the replicase is derived, and/or wherein the subgenomic promoter is a promoter for a structural protein of an alphavirus.

12. The system according to claim 1, wherein the RNA replicon comprises a 3' poly(A) sequence, and/or a 5'-cap.

13. The system according to claim 1, wherein the mRNA construct for expressing alphavirus replicase and/or the RNA replicon does not comprise an open reading frame encoding an intact alphavirus structural protein.

14. The system according to claim 1, wherein the alphavirus is Semliki Forest virus or Venezuelan equine encephalitis virus or Sindbis virus or Chikungunya Virus.

15. The system according to claim 1, wherein the mRNA is (+) strand mRNA.

16. The system according to claim 1, wherein the mRNA is in vitro transcribed mRNA.

17. The system according to claim 16, wherein the 5'-cap is a 5'-cap analog.

18. The system according to claim 1, wherein the mRNA is not fully codon-optimized.

19. The system according to claim 1, wherein the mRNA is comprised in a pharmaceutical composition comprising nanoparticles.

* * * * *